(12) United States Patent
Liang et al.

(10) Patent No.: US 11,091,510 B2
(45) Date of Patent: Aug. 17, 2021

(54) CRYSTAL CHARACTERISTICS, PREPARATION PROCESSES AND ANTICANCER APPLICATIONS OF 17BETA-NERIIFOLIN CRYSTAL FORMS

(71) Applicants: EnKang Pharmaceuticals (Guangzhou), Ltd., Guangzhou (CN); ENZHI (GUANGZHOU) PHARMACEUTICALS LIMITED, Guangzhou (CN); ENZYNOMICS (H.K.) LIMITED, Hong Kong (CN); FOSHAN INTELGEN PHARMACEUTICAL CO. LTD., Foshan (CN)

(72) Inventors: Chun Liang, Guangzhou (CN); Haibin Liu, Guangzhou (CN); Zeming Zhang, Guangzhou (CN); Guoqiang Song, Guangzhou (CN); Yushan Li, Guangzhou (CN); Weiqiang Zhang, Guangzhou (CN)

(73) Assignees: ENKANG PHARMACEUTICALS (GUANGZHOU), LTD., Guangzhou (CN); ENZHI (GUANGZHOU) PHARMACEUTICALS LIMITED, Guangzhou (CN); ENZYNOMICS (H.K.) LIMITED, Hong Kong (CN); FOSHAN INTELGEN PHARMACEUTICAL CO. LTD., Foshan (CN)

( * ) Notice: Subject to any disclaimer, the term of this patent is extended or adjusted under 35 U.S.C. 154(b) by 0 days.

(21) Appl. No.: 16/688,169

(22) Filed: Nov. 19, 2019

(65) Prior Publication Data

US 2020/0157139 A1 May 21, 2020

Related U.S. Application Data

(63) Continuation-in-part of application No. PCT/CN2018/087031, filed on May 16, 2018.

(30) Foreign Application Priority Data

May 19, 2017 (CN) .......................... 201710358086.9

(51) Int. Cl.
C07J 19/00 (2006.01)
(52) U.S. Cl.
CPC ......... *C07J 19/005* (2013.01); *C07B 2200/13* (2013.01)

(58) Field of Classification Search
None
See application file for complete search history.

(56) References Cited

FOREIGN PATENT DOCUMENTS

CN 104736157 A 6/2015
WO 2013169989 A1 11/2013

OTHER PUBLICATIONS

Rangaswami, J. Sci. Industr. Res., vol. 16B, May 1957. (Year: 1957).*
El-Shazly, Ann. Appl. Biol. (2000), 136:153-157. (Year: 2000).*
Fun, et al."Absolute Configuration of 14β-hydroxy-3β-O-(L-thevetosyl)-5β-card-20(22)-enolide Chloroform Disolvate", Acta Crystallographica Section E, vol. E59, 201, ISSN:1600-5368, p. 694-1696, Figure 1.
Fun, et al., ."Single Crystal X-ray Structural Determination: a Powerful Technique for Natural Products Research and Drug Discovery", Advanced Materials Research, Switzerland, vol. 545, 2012, ISSN:1022-6680, pp. 6-7, Figure 4.
Jeffrey, et al., "Structure and Specificity of the Anti-digoxin Antibody 40-50", Journal of Molecular Biology, vol. 284, No. 2, 1995, ISSN:0022-2836, pp. 334-360, Table 1.
Lang, et al., "Studies on the Cardiac Glycosides of Thevetia Peruviana (Merr. Syn. Thevetia Neriifolia Juss., II. Isolation and Identification of Cerberin, Ruvoside, and a New Cardiac Glycoside—Perusitin" Yaoxue Xuebao, vol. 11, No. 7, 1964, ISSN: 0513-4870, pp. 468-469.
Prasad, et al. "A Review on Management of Common Oleander and Yellow Oleander Poisoning", World Journal of Pharmacy and Pharmaceutical Sciences, Vol .5, No. 12, 2003,ISSN: 2278-4357. pp. 493-503.
International Search Report and the Written Opinion of the International Searching Authority for PCT/CN2018/087031, dated Aug. 20, 2018, ISA,CN, Beijing, China.

* cited by examiner

*Primary Examiner* — Layla D Berry
(74) *Attorney, Agent, or Firm* — Bayramoglu Law Offices LLC

(57) ABSTRACT

The present invention provides the preparation processes for several crystal forms of the compound 17beta-Neriifolin (17bNF) and use thereof in anti-tumor applications. The present invention provides preparation processes for four kinds of non-solvated crystal forms, amorphous powders and eleven kinds of solvated crystalline solids, including ethanol-solvated ones, of 17bNF that are not present in nature, and the identification and characterization of these crystal forms by crystallographic research methods such as X-ray powder diffraction. In addition, through vivo antitumor experiments with five of the crystal forms in nude mice, we provide anti-tumor and anti-cancer applications of the crystal forms of 17bNF.

8 Claims, 55 Drawing Sheets

Figure 1:
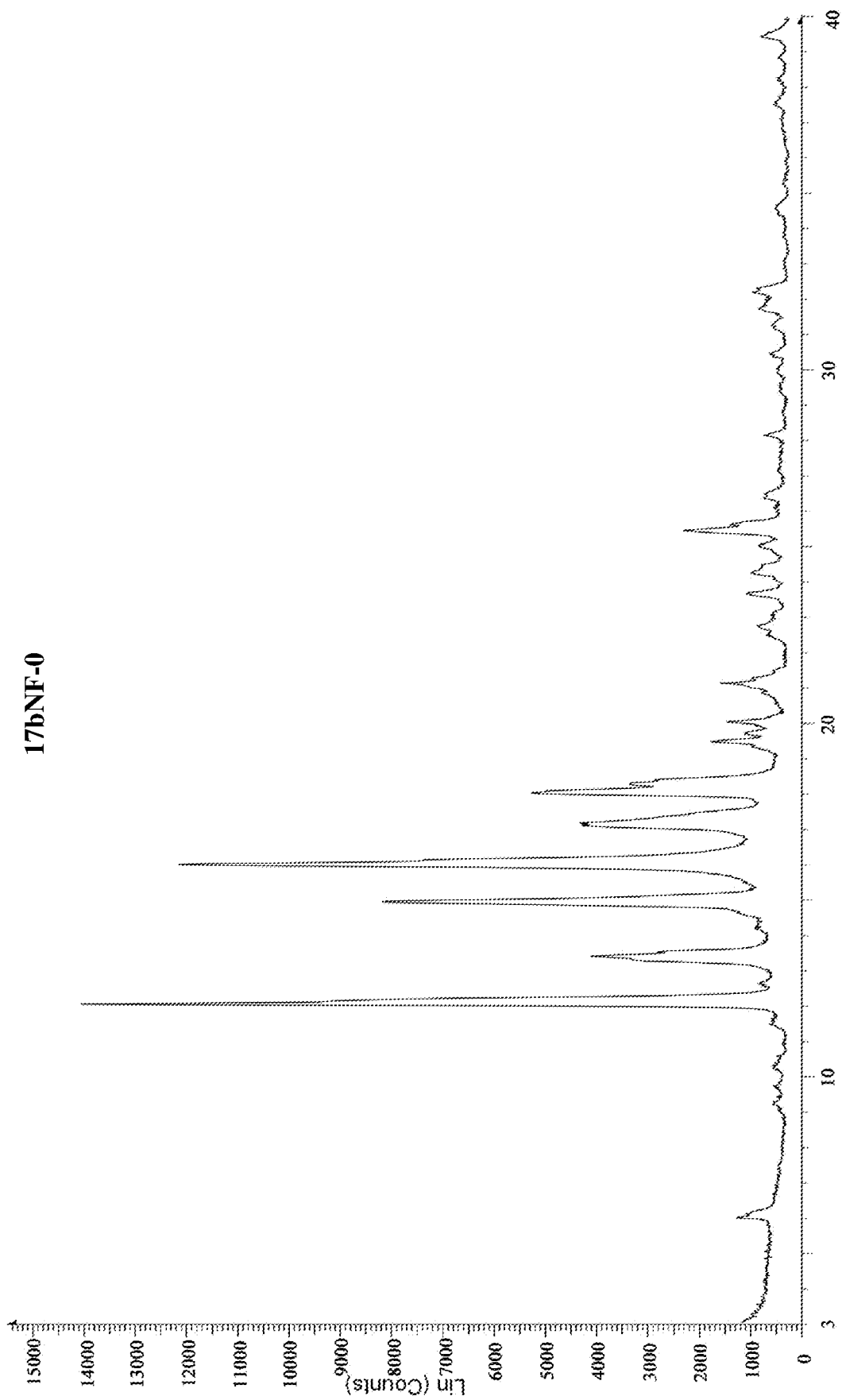
Figure 2:
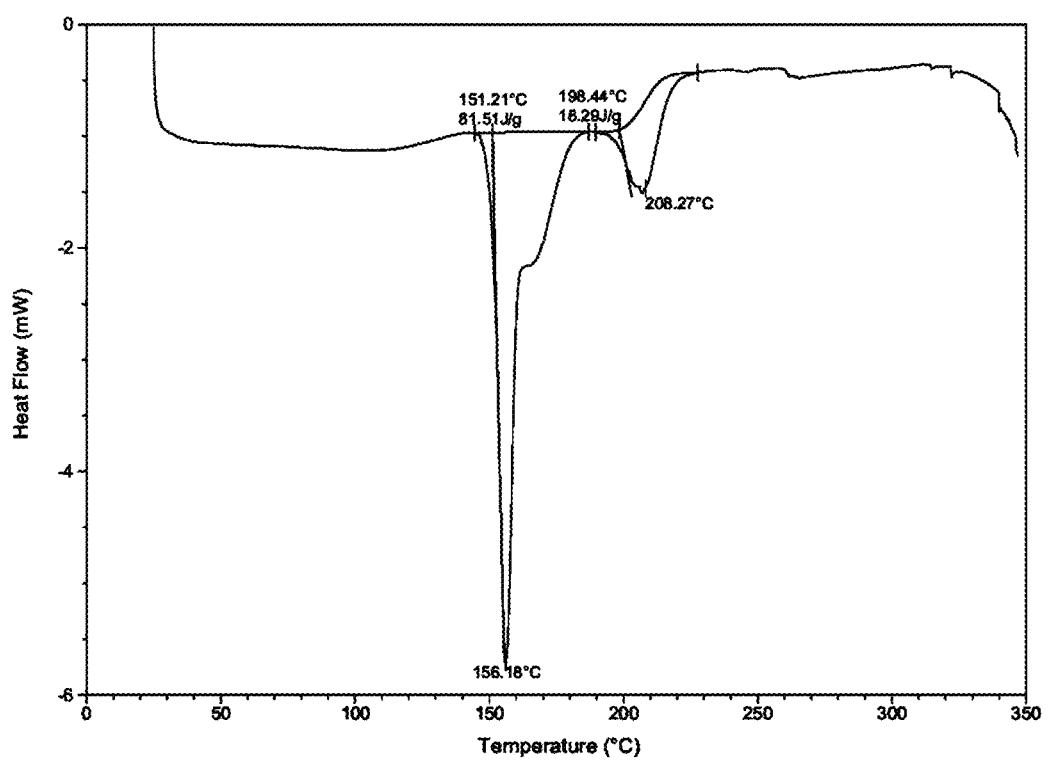
Figure 3:
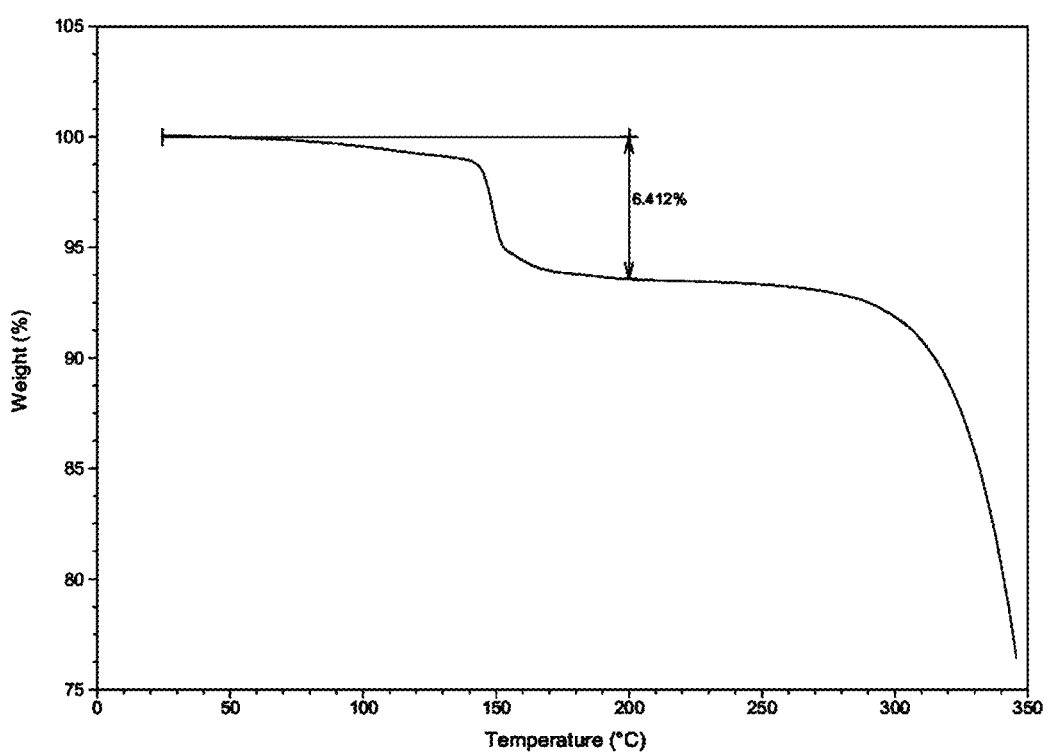

CRYSTAL CHARACTERISTICS, PREPARATION PROCESSES AND ANTICANCER APPLICATIONS OF 17BETA-NERIIFOLIN CRYSTAL FORMS

CROSS-REFERENCE TO RELATED APPLICATIONS

This application is a continuation-in-part of International Application No. PCT/CN2018/087031 filed on May 16, 2018, which claims priority from Chinese patent application No. 201710358086.9 filed May 19, 2017. The contents of the above-referenced applications are hereby incorporated by reference.

FIELD OF THE INVENTION

The present invention relates to a variety of solid-state forms of 17beta-Neriifolin (17bNF) do not exist in nature, including various crystal forms and amorphous materials, and the characteristics, preparation processes and anti-tumor and anti-cancer application methods of these new forms.

BACKGROUND OF THE INVENTION

Cancer cells are mutated cells that can proliferate indefinitely invade surrounding healthy tissue cells, metastasize and spread. At present, conventional drugs for treating cancer will cause serious damage to healthy tissue cells while killing cancer cells. CN 104736157A patent describes an active drug that can destroy tumor cells without causing significant damage to normal cells and tissues, and is named as 17β-neriifolin, which is 17bNF described in this invention.

The chemical name of 17bNF is (3β, 5β)-3-[(6-deoxy-3-O-methyl-α-L-glucopyranosyl) oxy]-14-hydroxycard-20 (22)-enolide. The structure of 17bNF is as follows:

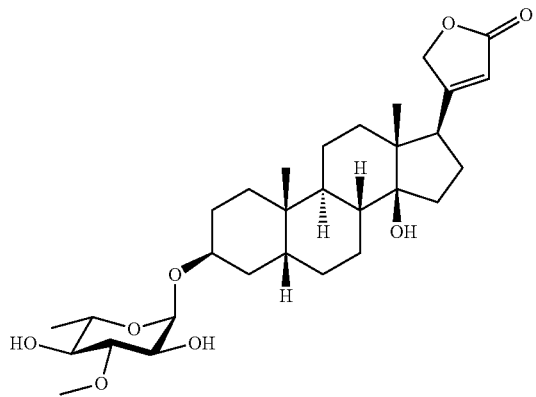

Due to different molecular conformations of different 17bNF crystal forms, the physical properties of the crystals will be different, and the stability, solubility, dissolution rate, and activity of the drugs will also be affected in the preparation of related drugs.

Formulation experts can select and design different excipients and pharmaceutical dosage forms according to the characteristics of different crystal forms. During the preparation, the formation of different crystal forms can also be affected by the amount of solution and environmental conditions.

In the laboratory, different crystal forms can be distinguished by thermal behaviors of these crystal forms and X-ray powder diffraction, and thermal behaviors can be measured by techniques such as thermogravimetric analysis (TGA) and differential scanning calorimetry (DSC).

The present invention provides four kinds of non-solvated crystal forms of 17bNF that do not exist in nature, which are named as Crystal Form I (17bNF-I), Crystal Form II (17bNF-II), Crystal Form III (17bNF-III), and Crystal Form IV (17bNF-IV), respectively. The present invention also provides eleven kinds of solvated crystal forms of 17bNF, that do not exist in nature, which are named as Crystal Form 0 (17bNF-0), Crystal Form V, Crystal Form VI, Crystal Form VII, Crystal Form VII, Crystal Form IX, Crystal Form X, Crystal Form XI, Crystal Form XII, Crystal Form XIII, Crystal Form XIV, respectively. The present invention also provides amorphous 17bNF. Furthermore, the present invention also provides preparation processes, characteristics data, and application methods for the crystal forms described above.

SUMMARY OF THE INVENTION

The present invention in one aspect provides a 17bNF new crystal form that is characterized by some or all of the following data: the 2θ values of the powder X-ray diffraction characteristic peaks are mainly of 6.0°±0.2°, 12.0°±0.2°, 13.4°±0.2°, 14.9°±0.2°, 16.0°±0.2°, 17.1°±0.2°, 18.1°±0.2°, 19.6°±0.2°, 20.0°±0.2°, 21.1°±0.2°, and 25.5°±0.2°; the differential scanning calorimetry spectrum has endothermic peaks at ~156° C. and 208° C.; the thermogravimetric analysis spectrum has a weight loss of ~6.4% before 200° C., and the crystal form is an ethanol-solvated compound. The crystalline solid above is named as Crystal Form 0 of 17bNF (17bNF-0). The crystal form will be changed into Crystal Form I of 17bNF (17bNF-I) after being heated to lose the ethanol solvent at 180-200° C.

In another aspect, the present invention provides a preparation process for 17bNF that has at least one of the characteristics (such as XRPD peaks, DSC peaks and/or TGA data) of 17bNF Crystal Form 0 (17bNF-0). The preparation process comprises the following steps: heating 17bNF solids to reflux and dissolve in ethanol aqueous solution of 50%-95%; statically crystallizing the sample above at room temperature; filtering, collecting and drying the solids.

In another aspect, the present invention provides a new crystal form of 17bNF that is characterized by the following data: the 2θ values of the powder X-ray diffraction characteristic peaks are mainly of 6.1°±0.2°, 11.2°±0.2°, 11.4°±0.2°, 12.2°±0.2°, 15.5°±0.2°, 16.4°±0.2°, 17.5°±0.2°, 19.7°±0.2°, and 20.4°±0.2°; the differential scanning calorimetry spectrum has an endothermic peak at ~228° C.; and the thermogravimetric analysis spectrum has a weight loss of ~0.6% before 250° C. The crystalline solid above is named as Crystal Form I of 17bNF (17bNF-I).

In another aspect, the present invention provides a preparation process for 17bNF that has at least one of the characteristics of Crystal Form I (17bNF-I). The preparation process comprises the following steps: dissolving or suspending 17bNF powder or crystal solids including 17bNF-0 in methanol, ethanol, tetrahydrofuran, acetone, isobutyl alcohol, isopropyl acetate, 2-butanone, isopropyl alcohol, ethyl acetate, acetonitrile, toluene, methyl tert-butyl ether, water and other solvents; separately filtering the solutions or suspensions above, and then taking the filtrates; taking 17bNF methanol solution, or mixing 17bNF methanol solution with the filtrate of 17bNF isopropyl alcohol suspension, 17bNF tetrahydrofuran solution, 17bNF acetone solution, 17bNF isobutyl alcohol solution, 17bNF isopropyl acetate solution, the filtrate of 17bNF ethyl acetate suspension, the filtrate of 17bNF toluene suspension, or the filtrate of 17bNF methyl tert-butyl ether suspension, at 30%:70% to 70%:30% ratios, or better at ratios of 40%:60% to 60%:40%, or even better at a ratio of 50%:50%; or taking 17bNF ethanol solution, or mixing 17bNF ethanol solution with 17bNF tetrahydrofuran solution, 17bNF acetone solution, 17bNF isobutyl alcohol solution, 17bNF isopropyl acetate solution, 17bNF 2-butanone solution, the filtrate of 17bNF isopropyl alcohol suspension, the filtrate of 17bNF ethyl acetate suspension, the filtrate of 17bNF toluene suspension, or the filtrate of 17bNF methyl tert-butyl ether suspension, at 30%:70% to 70%:30% ratios, or better at ratios of 40%:60% to 60%:40%, or even better at a ratio of 50%:50%; or mixing the filtrate of 17bNF isopropyl alcohol suspension with 17bNF tetrahydrofuran solution, 17bNF acetone solution, 17bNF isobutyl alcohol solution, 17bNF isopropyl acetate solution, 17bNF 2-butanone solution, the filtrate of 17bNF isopropyl alcohol suspension, the filtrate of 17bNF ethyl acetate suspension, the filtrate of 17bNF acetonitrile suspension, or the filtrate of 17bNF toluene suspension, at 30%:70% to 70%:30% ratios, or better at ratios of 40%:60% to 60%:40%, or even better at a ratio of 50%:50%; or taking 17bNF tetrahydrofuran solution, or mixing 17bNF tetrahydrofuran solution with 17bNF acetone solution, 17bNF isobutyl alcohol solution, 17bNF isopropyl acetate solution, 17bNF 2-butanone solution, the filtrate of 17bNF ethyl acetate suspension, the filtrate of 17bNF acetonitrile suspension, the filtrate of 17bNF toluene suspension, or the filtrate of 17bNF methyl tert-butyl ether suspension, at 30%:70% to 70%:30% ratios, or better at ratios of 40%:60% to 60%:40%, or even better at a ratio of 50%:50%; or taking 17bNF ethyl acetate suspension, or mixing 17bNF ethyl acetate suspension with 17bNF acetone solution, 17bNF 2-butanone solution, or the filtrate of 17bNF acetonitrile suspension, at 30%:70% to 70%:30% ratios, or better at ratios of 40%:60% to 60%:40%, or even better at a ratio of 50%:50%; or taking 17bNF acetone solution, or mixing 17bNF acetone solution with 17bNF isobutyl alcohol solution, 17bNF isopropyl acetate solution, 17bNF 2-butanone solution, or the filtrate of 17bNF toluene suspension, at 30%:70% to 70%:30% ratios, or better at ratios of 40%:60% to 60%:40%, or even better at a ratio of 50%:50%; or taking 17bNF isobutyl alcohol solution, or mixing 17bNF isobutyl alcohol solution with 17bNF isopropyl acetate solution, the filtrate of 17bNF acetonitrile suspension, 17bNF 2-butanone solution, the filtrate of 17bNF toluene suspension, the filtrate of 17bNF water suspension or the filtrate of 17bNF methyl tert-butyl ether suspension, at 30%:70% to 70%:30% ratios, or better at ratios of 40%:60% to 60%:40%, or even better at a ratio of 50%:50%; or mixing 17bNF isopropyl acetate solution with 17bNF 2-butanone solution, at 30%:70% to 70%:30% ratios, or better at ratios of 40%:60% to 60%:40%, or even better at a ratio of 50%:50%; or mixing the filtrate of the 17bNF acetonitrile suspension with 17bNF 2-butanone solution, or the filtrate of 17bNF methyl tert-butyl ether suspension, at 30%:70% to 70%:30% ratios, or better at ratios of 40%:60% to 60%:40%, or even better at a ratio of 50%:50%; or taking 17bNF 2-butanone solution, or mixing 17bNF 2-butanone solution with the filtrate of 17bNF toluene suspension, the filtrate of 17bNF water suspension or the filtrate of 17bNF methyl tert-butyl ether suspension, at 30%:70% to 70%:30% ratios, or better at ratios of 40%:60% to 60%:40%, or even better at a ratio of 50%:50%;

The above solutions of 17bNF or the filtrates of 17bNF suspension in a single solvent, or the solutions of 17bNF or the mixed filtrates of 17bNF suspensions in two solvents are volatilized in natural environment or under similar conditions.

In another aspect, the present invention provides another preparation process for Crystal Form I of 17bNF (17bNF-I) which has at least one of its characteristics. The preparation process comprises the following steps: suspending 17bNF-0 solid in ethyl ether, and keeping stirring; filtering the suspension, collecting and drying the solid, and obtaining the non-solvated Crystal Form I of 17bNF (17bNF-I).

In another aspect, the present invention provides a new crystal form of 17bNF that is characterized by the following data: the 2θ values of the powder X-ray diffraction characteristic peaks are mainly of 6.4°±0.2°, 10.1°±0.2°, 12.6°±0.2°, 12.8°±0.2°, 13.3°±0.2°, 14.8°±0.2°, 15.5°±0.2°, 16.5°±0.2°, 17.8°±0.2°, 18.1°±0.2°, 18.4°±0.2°, 18.7°±0.2°, 19.3°±0.2°, 20.2°±0.2°, 21.9°±0.2°, 22.4°±0.2°, 23.4°±0.2°, 24.3°±0.2°, 25.8°±0.2°, 26.4°±0.2°, 27.0°±0.2° and 27.5°±0.2°; the differential scanning calorimetry (DSC) spectrum has endothermic peaks at ~82-92° C., ~145-155° C. and ≤225-235° C., and has exothermic peak at ~144-164° C. The thermogravimetric analysis (TGA) spectrum has a weight loss of ~2.9% before 100° C. The solid crystal form described above is named as Crystal Form II of 17bNF (17bNF-II). The crystal form will be changed into Crystal Form III of 17bNF (17bNF-III) after being heated at 160° C.

In another aspect, the present invention provides a preparation process for Crystal Form II of 17bNF (17bNF-II) which has at least one of its characteristics. The preparation process comprises the following steps: suspending 17bNF-0 solid in water, and keeping stirring; filtering the suspension, collecting and drying the solid, and obtaining the non-solvated Crystal Form II of 17bNF (17bNF-II).

In another aspect, the present invention provides a new crystal form of 17bNF that is characterized by the following data: the 2θ values of the powder X-ray diffraction characteristic peaks are mainly of 6.1±0.2°, 6.4±0.2°, 9.7±0.2°, 11.4±0.2°, 12.2±0.2°, 12.8±0.2°, 15.3±0.2°, 15.6±0.2°, 16.3±0.2°, 16.6±0.2°, 16.8±0.2°, 17.4±0.2°, 19.5±0.2° and 20.3±0.2°; the differential scanning calorimetry (DSC) spectrum has endothermic peaks at ~219-239° C., and the crystal form is a non-solvated. The solid crystal form described above is named as Crystal Form III of 17bNF (17bNF-III).

In another aspect, the present invention provides a preparation process for Crystal Form III of 17bNF (17bNF-III) which has at least one of its characteristics. The preparation process comprises the following steps: suspending 17bNF-0 solid in acetonitrile, and keeping stirring; filtering the suspension, collecting and drying the solid, and obtaining the acetonitrile-solvated compound; heating the solvated compound at 150-170° C. to lose solvent and change it into the non-solvated Crystal Form III of 17bNF (17bNF-III).

In another aspect, the present invention provides a new crystal form of 17bNF that is characterized by the following data: the 2θ values of the powder X-ray diffraction characteristic peaks are mainly of 5.6°±0.2°, 12.6°±0.2°, 13.5°±0.2°, 14.2°±0.2°, 14.5°±0.2°, 15.3°±0.2°, 16.5°±0.2°, 18.1°±0.2°, 18.8°±0.2°, 19.6°±0.2°, 19.9°±0.2°, 20.6°±0.2°, 22.0°±0.2°, 24.2°±0.2°, 24.9°±0.2° and 25.4°±0.2°, the differential scanning calorimetry (DSC) spectrum has endothermic peaks at ~180-200° C. and ~222-242° C., and the crystal form is non-solvated. The solid crystal form described above is named as Crystal Form IV of 17bNF (17bNF-IV). It will be changed into 17bNF Crystal Form I (17bNF-I) after being heated at 180-200° C.

In another aspect, the present invention provides a preparation process for Crystal Form IV of 17bNF that has at least one of its characteristics. The preparation process comprises the following steps: suspending 17bNF-0 solid in methyl tert-butyl ether to produce a suspension; stirring and beating the suspension, and it is better to add some seed crystal (17bNF-IV); filtering the suspension, collecting and drying the solid, and obtaining the non-solvated Crystal Form IV of 17bNF (17bNF-IV).

In another aspect, the present invention provides a new crystal form of 17bNF that is characterized by the following data: the 2θ values of the powder X-ray diffraction characteristic peaks are mainly of 5.3±0.2°, 10.6±0.2°, 11.8±0.2°, 12.1±0.2°, 13.3±0.2°, 14.3±0.2°, 14.9±0.2°, 15.9±0.2°, 17.2±0.2°, 17.4±0.2°, 17.7±0.2°, 18.0±0.2°, 18.3±0.2° and 25.6±0.2°; the differential scanning calorimetry (DSC) spectrum having the endothermic peaks at 98-118° C., ~144-164° C. and ~217-237° C.; and the thermogravimetric analysis (TGA) spectrum having a weight loss of ~5.6% at 140° C. and ~6.8% at 190° C. The crystal form is a solvate and is named as Crystal Form V of 17bNF. The crystal form will be changed into Crystal Form VI of 17bNF (17bNF-VI) after being heated at 180-200° C. by TGA.

In another aspect, the present invention provides a preparation process for Crystal Form V of 17bNF that has at least one of the characteristics. The preparation process comprises the following steps: suspending 17bNF-0 solid in isopropyl alcohol, and keeping stirring; filtering the suspension, collecting and drying the solid, and obtaining the crystal form V of 17bNF.

In another aspect, the present invention provides a new crystal form of 17bNF that is characterized by the following data: the 2θ values of the powder X-ray diffraction characteristic peaks are mainly of 6.1°±0.2°, 6.3°±0.2°, 11.1°±0.2°, 12.2°±0.2°, 12.7°±0.2°, 15.4°±0.2°, 16.3°±0.2°, 17.4°±0.2°, 19.6°±0.2°, 20.4°±0.2° and 20.7°±0.2°; The crystal form is a solvate; the thermogravimetric analysis (TGA) spectrum has a weight loss of ~2.8% at 200° C. This crystalline solid is named as Crystal Form VI of 17bNF. The crystal form will be changed into Crystal Form I of 17bNF after being heated to lose solvent by TGA.

In another aspect, the present invention provides a preparation process for Crystal Form VI of 17bNF that has at least one of its characteristics. The preparation process comprises the following steps: dissolving 17bNF powder or crystalline solids including 17bNF-0 in methanol and 2-butanone, separately; filtering the solutions, and then taking the filtrates, separately; mixing 17bNF methanol solution with 17bNF 2-butanone solution at ratios of 30%:70% to 70%:30%, or better at ratios of 40%:60% to 60%:40%, or even better at a ratio of 50%:50%; drying the above mixture in natural environment or under similar conditions.

In another aspect, the present invention provides a 17bNF new crystal form that is characterized by the following data: the 2θ values of the powder X-ray diffraction characteristic peaks are mainly of 11.8°±0.2°, 12.1°±0.2°, 12.6°±0.2°, 14.9°±0.2°, 17.1°±0.2°, 17.3°±0.2°, 18.2°±0.2°, 18.8°±0.2°, 19.5°±0.2°, 22.8°±0.2° and 25.5°±0.2°; the differential scanning calorimetry (DSC) spectrum having the endothermic peaks at ~119-139° C., ~131-151° C. and ~221-241° C., and the thermogravimetric analysis (TGA) spectrum has a weight loss of ~7.0% at 160° C. The crystal form is a solvate and is named as Crystal Form VII of 17bNF. The crystal form will be changed into Crystal Form I of 17bNF after being heated to lose solvent by TGA.

In another aspect, this invention provides the preparation process for the Crystal Form VII of 17bNF that has at least one of its characteristics. The preparation process comprises the following steps: suspending or dissolving 17bNF powder or crystal solids including 17bNF-0 in ethyl acetate and isopropyl acetate separately; mixing the filtrate of 17bNF ethyl acetate suspension with the 17bNF isopropyl acetate solution, at 30%:70% to 70%:30% ratios, or better at ratios of 40%:60% to 60%:40%, or even better at a ratio of 50%:50%; drying the above mixture in natural environment or under similar conditions.

In another aspect, this invention provides another preparation process for the Crystal Form VII of 17bNF that has at least one of its characteristics. The preparation process comprises the following steps: suspending the Crystal Form 0 of 17bNF solids in ethyl acetate and keeping stirring; filtering the suspension, collecting and drying the solids, and obtaining the Crystal Form VII of 17bNF.

In another aspect, this invention provides another preparation process for the Crystal Form VII of 17bNF that has at least one of its characteristics. The preparation process comprises the following steps: dissolving 17bNF powder or crystalline solids including 17bNF-0 in tetrahydrofuran and obtaining a solution; adding ethyl ether to the above-mentioned solution and keeping stirring to precipitate the sample; filtering and collecting the precipitates, and obtaining the Crystal Form VII.

In another aspect, the present invention provides a new crystal form of 17bNF that is characterized by the following data: it is the solvated compounds; the 2θ values of the powder X-ray diffraction characteristic peaks are mainly of 8.8°±0.2°, 10.3°±0.2°, 11.1°±0.2°, 11.5°±0.2°, 14.5°±0.2°, 15.4°±0.2°, 16.9°±0.2°, 17.7°±0.2°, 17.9°±0.2°, 20.0°±0.2°, 20.2°±0.2°, and 20.7°±0.2°; the differential scanning calorimetry (DSC) spectrum has endothermic peaks at ~98-118° C., ~121-141° C. and ~223-243° C., and exothermic peaks at ~143-163° C.; and the thermogravimetric analysis (TGA) spectrum has a weight loss of ~4.5% at ~100° C. The solid crystal form is named as the Crystal Form VIII of 17bNF. It will be desolvented and changed into 17bNF Crystal Form III when it is heated at 150-170° C. by TGA.

In another aspect, this invention provides the preparation process for the Crystal Form VIII of 17bNF that has at least one of its characteristics. The preparation process comprises the following steps: suspending 17bNF-0 solids in acetonitrile and keeping stirring; filtering the suspension, collecting and drying the solids, and obtaining the Crystal Form VIII of 17bNF.

In another aspect, the present invention provides a new crystal form of 17bNF that is characterized by the following data: it is the solvated compounds; the 2θ values of the powder X-ray diffraction characteristic peaks are mainly of 10.6°±0.2°, 12.1°±0.2°, 12.9°±0.2°, 13.4°±0.2°, 14.3°±0.2°, 14.9°±0.2°, 16.0°±0.2°, 16.5°±0.2°, 17.3°±0.2°, 17.8°±0.2°, 18.1°±0.2°, 18.7°±0.2°, 19.4°±0.2°, and 25.8°±0.2°; the differential scanning calorimetry (DSC) spectrum has endothermic peaks at ~73-83° C., ~151-161° C. and ~225-235° C., and the thermogravimetric analysis (TGA) spectrum has a weight loss of ~2.1% at ~70° C. and ~2.7% at ~190° C. The solid crystal form is named as the Crystal Form IX of 17bNF It will be desolvented and changed into 17bNF Crystal Form I when it is heated at 190-210° C. by TGA.

In another aspect, this invention provides the preparation process for the Crystal Form IX of 17bNF that has at least one of its characteristic comprises. The preparation process comprises the following steps: suspending 17bNF-0 solids in toluene and keeping stirring; filtering the suspension, collecting and drying the solids, and obtaining the Crystal Form IX of 17bNF.

In another aspect, the present invention provides a new crystal form of 17bNF that is characterized by the following data: the crystal form is a solvate; the 2θ values of the powder X-ray diffraction characteristic peaks are mainly of 6.1°±0.2°, 11.1°±0.2°, 11.4°±0.2°, 11.6°±0.2°, 12.2°±0.2°, 15.4°±0.2°, 16.3°±0.2°, 17.4°±0.200, 18.6°±0.2°, 19.6°±0.2° and 20.4°±0.2°, and the thermogravimetric analysis (TGA) spectrum with a weight loss of ~1.6% at 155° C. The crystalline solid described above is named as the Crystal Form X of 17bNF. The crystal form will be changed into Crystal Form I of 17bNF after being heated at 150-170° C. by TGA.

In another aspect, the present invention provides a preparation process for 17bNF that has at least one of the characteristics of 17bNF Crystal Form X. The preparation process comprises the following steps: suspending or dissolving 17bNF powder or crystalline solids including 17bNF-0 in ethyl acetate and isobutanol separately; filtering the solutions or suspensions separately, and then taking the filtrates; mixing the filtrate of the 17bNF ethyl acetate suspension with 17bNF isobutanol solution, at ratios of 30%:70% to 70%:30%, or better at ratios of 40%:60% to 60%:40%, or even better at a ratio of 50%:50%; volatilizing the mixture above in the natural environment or under similar conditions.

In another aspect, the present invention provides a new crystal form of 17bNF that is characterized by the following data: the crystal form is a solvate; the 2θ values of the powder X-ray diffraction characteristic peaks are mainly of 5.9°±0.2°, 6.1°±0.2°, 11.8°±0.2°, 12.2°±0.2°, 13.4°±0.2°, 14.8°±0.2°, 16.1°±0.2°, 17.0°±0.2°, 17.3°±0.2°, 17.9°±0.2°, 18.5°±0.2°, 25.7°±0.2° and 26.2°±0.2°, and the thermogravimetric analysis (TGA) spectrum with a weight loss of ~1.5% at ~185° C. The crystalline solid described above is named as the Crystal Form XI of 17bNF. The crystal form will be changed into Crystal Form I of 17bNF after being heated at 180-200° C. by TGA.

In another aspect, the present invention provides a preparation process for 17bNF that has at least one of the characteristics of 17bNF Crystal Form XI, the preparation process comprises the following steps: suspending 17bNF powder or crystalline solids including 17bNF-0 in ethyl acetate and methyl tert-butyl ether separately to obtain suspensions; filtering the suspensions separately, and then taking the filtrates; mixing the filtrate of the 17bNF ethyl acetate suspension with the filtrate of the 17bNF methyl tert-butyl ether suspension, at ratios of 30%:70% to 70%:30%, or better at ratios of 40%:60% to 60%:40%, or even better at a ratio of 50%:50%; volatilizing the mixture above in natural environment or under similar conditions.

In another aspect, the present invention provides a new crystal form of 17bNF that is characterized by the following data: the crystal form is a solvate; the 2θ values of the powder X-ray diffraction characteristic peaks are mainly of 6.1°±0.2°, 11.1°±0.2°, 12.0°±0.2°, 12.2°±0.2°, 12.7°±0.2°, 15.4°±0.2°, 16.3°±0.2°, 17.4°±0.2°, 19.6°±0.2°, 20.5°±0.2°, 20.7°±0.2° and 30.8°±0.2°, and the thermogravimetric analysis (TGA) spectrum with a weight loss of ~1.5% at ~158° C. The crystalline solid described above is named as the Crystal Form XII of 17bNF. The crystal form will be changed into Crystal Form I of 17bNF after being heated at 170-190° C. by TGA.

In another aspect, the present invention provides a preparation process for Crystal Form XII of 17bNF that has at least one of the characteristics. The preparation process comprises the following steps: suspending or dissolving 17bNF powder or crystalline solids including 17bNF-0 in acetone and methyl tert-butyl ether separately; filtering the solutions or suspensions separately, and then taking the filtrates; mixing the acetone solution of 17bNF with the filtrate of 17bNF methyl tert-butyl ether suspension, at ratios of 30%:70% to 70%:30%, or better at ratios of 40%:60% to 60%:40%, or even better at a ratio of 50%:50%; volatilizing the mixture above in natural environment or under similar conditions.

In another aspect, the present invention provides a new crystal form of 17bNF that is characterized by the following data: the crystal form is a solvated compound, the 2θ values of the powder X-ray diffraction characteristic peaks are of mainly of 6.1°±0.2°, 11.1°±0.2°, 12.2°±0.2°, 12.8°±0.2°, 15.4°±0.2°, 16.3°±0.2°, 17.4°±0.2°, 19.6°±0.2°, 20.4°±0.2°, 20.6°±0.2°, 26.4°±0.2°, and 30.8°±0.2∪, and the thermogravimetric analysis (TGA) spectrum with a weight loss of ~1.3% at ~185° C. The solid crystal form described above is named as the Crystal Form XIII of 17bNF The crystal form will be changed into Crystal Form I of 17bNF after being heated at 180-200° C. by TGA.

In another aspect, the present invention provides a preparation process for Crystal Form XIII of 17bNF that has at least one of its characteristics. The preparation process comprises the following steps: dissolving 17bNF powder or crystalline solids including 17bNF-0 in isopropyl acetate and obtain a solution; filtering the solution in Step a, and then taking the filtrate; volatilizing the mixture above under the natural environment or similar conditions and obtaining the solid for the Crystal Form XIII of 17bNF.

In another aspect, the present invention provides a new crystal form of 17bNF that is characterized by the following data: it is a solvated compound; the 2θ values of the powder X-ray diffraction characteristic peaks are mainly of 11.9°±0.2°, 12.7°±0.2°, 13.2°±0.2°, 14.4°±0.2°, 14.9°±0.2°, 15.5°±0.2°, 16.9°±0.2°, 17.1°±0.2°, 17.4°±0.2°, 18.0°±0.2°, 18.8°±0.2° and 25.6°±0.2°; the differential scanning calorimetry (DSC) spectrum has endothermic peaks at ~139-149° C., ~222-232° C. and ~229-239° C.; and the thermogravimetric analysis (TGA) spectrum has a weight loss of ~5.1% at ~160'C. The solid crystal form is named as the Crystal Form XIV of 17bNF. The Crystal Form X IV of 17bNF will be changed into Crystal Form VI of 17bNF when it is heated to lose solvent by DSC.

In another aspect, the present invention provides a preparation process for 17bNF that has at least one of the characteristics of 17bNF Crystal Form XIV. The preparation process comprises the following steps: dissolving 17bNF powder or crystalline solids including 17bNF-0 in acetone and obtain solutions; adding ethyl ether or cyclohexane to the above solution and keeping stirring to precipitate the sample; filtering and collecting the precipitated precipitation and obtaining the Crystal Form XIV.

In another aspect, the present invention provides a preparation process for an amorphous form compound 17bNF. The preparation process comprises the following steps: suspending 17bNF powder or crystalline solids including 17bNF-0 in acetonitrile and toluene separately; filtering the suspensions separately, and then taking the filtrates; mixing the filtrate of 17bNF acetonitrile suspension with the filtrate of 17bNF toluene suspension, at ratios of 30%:70% to 70%:30%, or better at ratios of 40%:60% to 60%:40%, or even better at a ratio of 50%:50%; volatilizing the mixture above in natural environment or under similar conditions.

In another aspect, it can be deduced from the well-known methods in the field that it is also possible to prepare amorphous solid of 17bNF or new crystal forms at the prompt of the present invention by choosing more than two of the solvents described above, or single or multiple other solvents similar to the solvents described above.

In another aspect, the present invention provides anti-tumor and anti-cancer application methods for the crystal forms of 17bNF. The experimental results from the nude mouse models of human cancer cells show that various 17bNF crystal forms in the present invention have high anticancer activities in vivo. The application methods of the present invention comprise: select the crystal forms of 17bNF described in this patent application as antitumor and anticancer drugs, or give effective doses of pharmaceutical preparations containing the various crystal forms of 17bNF-to tumor and cancer patients.

BRIEF DESCRIPTION OF THE DRAWINGS

FIG. 1 shows the powder X-ray diffraction characteristic peaks of 17bNF Crystal Form 0.

FIG. 2 shows the differential scanning calorimetry (DSC) spectrum of 17bNF Crystal Form 0.

FIG. 3 shows the thermogravimetric analysis (TGA) spectrum of 17bNF Crystal Form 0.

FIG. 4 shows the powder X-ray diffraction characteristic peaks of 17bNF Crystal Form I.

FIG. 5 shows the differential scanning calorimetry (DSC) spectrum of 17bNF Crystal Form I.

FIG. 6 shows the thermogravimetric analysis (TGA) spectrum of 17bNF Crystal Form I.

FIG. 7 shows the powder X-ray diffraction characteristic peaks of 17bNF Crystal Form II.

FIG. 8 shows the differential scanning calorimetry (DSC) spectrum of 17bNF Crystal Form II.

FIG. 9 shows the thermogravimetric analysis (TGA) spectrum of 17bNF Crystal Form II.

FIG. 10 shows the differential scanning calorimetry (DSC) spectrum of 17bNF Crystal Form III.

FIG. 11 shows the thermogravimetric analysis (TGA) spectrum of 17bNF Crystal Form III.

FIG. 12 shows the powder X-ray diffraction characteristic peaks of 17bNF Crystal Form III.

FIG. 13 shows the powder X-ray diffraction characteristic peaks of 17bNF Crystal Form IV.

FIG. 14 shows the differential scanning calorimetry (DSC) spectrum of 17bNF Crystal Form IV.

FIG. 15 shows the thermogravimetric analysis (TGA) spectrum of 17bNF Crystal Form IV.

FIG. 16 shows the powder X-ray diffraction characteristic peaks of 17bNF Crystal Form V.

FIG. 17 shows the thermogravimetric analysis (TGA) spectrum of 17bNF Crystal Form V.

FIG. 18 shows the differential scanning calorimetry (DSC) spectrum of 17bNF Crystal Form V.

FIG. 19 shows the thermogravimetric analysis (TGA) spectrum of 17bNF Crystal Form VI.

FIG. 20 shows the powder X-ray diffraction characteristic peaks of 17bNF Crystal Form VI.

FIG. 21 shows the powder X-ray diffraction characteristic peaks of 17bNF Crystal Form VII.

FIG. 22 shows the thermogravimetric analysis (TGA) spectrum of 17bNF Crystal Form VII.

FIG. 23 shows the differential scanning calorimetry (DSC) spectrum of 17bNF Crystal Form VII.

FIG. 24 shows the powder X-ray diffraction characteristic peaks of 17bNF Crystal Form VIII.

FIG. 25 shows the thermogravimetric analysis (TGA) spectrum of 17bNF Crystal Form VIII.

FIG. 26 shows the differential scanning calorimetry (DSC) spectrum of 17bNF Crystal Form VIII.

FIG. 27 shows the powder X-ray diffraction characteristic peaks of 17bNF Crystal Form IX.

FIG. 28 shows the thermogravimetric analysis (TGA) spectrum of 17bNF Crystal Form IX.

FIG. 29 shows the differential scanning calorimetry (DSC) spectrum of 17bNF Crystal Form IX.

FIG. 30 shows the powder X-ray diffraction characteristic peaks of 17bNF Crystal Form X.

FIG. 31 shows the thermogravimetric analysis (TGA) spectrum of 17bNF Crystal Form X.

FIG. 32 shows the powder X-ray diffraction characteristic peaks of 17bNF Crystal Form XI.

FIG. 33 shows the thermogravimetric analysis (TGA) spectrum of 17bNF Crystal Form XI.

FIG. 34 shows the powder X-ray diffraction characteristic peaks of 17bNF Crystal Form XII.

FIG. 35 shows the thermogravimetric analysis (TGA) spectrum of 17bNF Crystal Form XII.

FIG. 36 shows the powder X-ray diffraction characteristic peaks of 17bNF Crystal Form XIII.

FIG. 37 shows the thermogravimetric analysis (TGA) spectrum of 17bNF Crystal Form XIII.

FIG. 38 shows the powder X-ray diffraction characteristic peaks of 17bNF Crystal Form XIV.

FIG. 39 shows the thermogravimetric analysis (TGA) spectrum of 17bNF Crystal Form XIV.

FIG. 40 shows the differential scanning calorimetry (DSC) spectrum of 17bNF Crystal Form XIV.

FIG. 41 shows the powder X-ray diffraction characteristic peaks of 17bNF in the amorphous form.

FIG. 42A-C show the in vivo anticancer efficacy test results of 17bNF Crystal Form 0 and 17bNF Crystal Form II.

FIG. 43 shows the in vivo anticancer efficacy test-1 results of 17bNF Crystal Form 0 to 17bNF Crystal Form IV (17bNF-0 to 17bNF-IV).

FIG. 44 shows the in vivo anticancer efficacy test-2 results of 17bNF Crystal Form 0 to 17bNF Crystal Form IV (17bNF-0 to 17bNF-IV).

FIG. 45 shows the superimposed XRPD spectra of crystal form I in stability testing.

FIG. 46 shows the superimposed XRPD spectra of crystal form III in stability testing.

FIG. 47 shows the superimposed XRPD spectra of crystal form IV in stability testing.

FIG. 48 shows the XRPD spectra of samples of crystal form II in stress testing.

FIG. 49 shows the XRPD spectra of samples of crystal form II in accelerating testing.

FIGS. 50A and 50B show XRPD spectra of samples of crystal form II in long-term testing.

FIG. 51 shows the superimposed spectra of suspended crystal transformation in tests 1 and 2.

FIG. 52 shows the superimposed spectra of suspended crystal transformation in tests 3 to 5.

DETAILED DESCRIPTION OF THE EMBODIMENTS

Instrument

X-Ray Powder Diffraction (XRPD)

The methods used for determining the X-ray diffraction patterns of the crystalline forms are known in the art. We used Bruker D8 advance X-ray powder diffraction instrument equipped with the LynxEye detector. The scanning range was from 3° to 400 2θ with the scanning step of 0.02°. The power supply setting was 40 kV and 40 mA. The sample tray used for sample measurement was a zero background tray.

Thermogravimetric Analysis (TGA)

Thermogravimetric analysis instrument TA TGA Q500 was used to analyze the samples in aluminum sample trays at a heating rate of 10° C./min. The weight of the samples ranged from 2 mg to 3 mg, the protective gas was $N_2$, and the flow rates of $N_2$ to the balance chamber and sample chamber were 40 mL/min and 60 mL/min, respectively.

The Differential Scanning Calorimetry (DSC)

TA QSC Q200 differential scanning calorimeter was used to analyze the samples at a heating rate of 10° C./min. The standard sample used for calibration was Indium. The weight of the samples ranged from 2 mg to 3 mg, the protective gas was $N_2$, and the flow rate of $N_2$ was 50 mL/min.

The following examples further illustrate this invention:

EXAMPLES

Example 1—Preparation of the Crystal Form 0 of 17bNF (17bNF-0)

17bNF powder or solids were completely dissolved in ethanol solution under heating and refluxing conditions, followed by cooling statically at room temperature until crystallisation. The solids were filtered, collected and dried to obtain the Crystal Form 0 of 17bNF (17bNF-0).

Example 2—Preparation of the Crystal Form I of 17bNF (17bNF-I)

17bNF-0 powder or crystalline solids were dissolved or suspended in solvents to produce solutions or suspensions as stated in Table 1.

TABLE 1

The mass and volume of materials used for the liquid sample preparation

| Number | Solvent | Volume (mL) | 17bNF Mass (mg) |
|---|---|---|---|
| 1 | Methanol | 3 | 59.8 |
| 2 | Ethanol | 3 | 60.0 |
| 3 | Isopropyl alcohol | 3 | 60.3 |
| 4 | Tetrahydrofuran | 3 | 60.2 |
| 5 | Ethyl acetate | 3 | 59.8 |
| 6 | Acetone | 3 | 59.8 |
| 7 | Isobutyl alcohol | 3 | 59.9 |
| 8 | isopropyl acetate | 3 | 60.2 |
| 9 | Acetonitrile | 3 | 60.1 |
| 10 | 2-Butanone | 3 | 60.3 |
| 11 | Toluene | 3 | 60.1 |
| 12 | Water | 3 | 60.1 |
| 13 | Methyl tert-butyl ether | 3 | 60.2 |

The solutions or suspensions were filtrated separately to obtain filtrates. 100 μl of the 17bNF methanol solution were mixed with 100 μl of the 17bNF methanol solution, filtrate of the 17bNF tetrahydrofuran solution, 17bNF acetone solution, 17bNF isobutyl alcohol solution, 17bNF isopropyl acetate solution, 17bNF isopropyl alcohol suspension, the filtrate of the 17bNF ethyl acetate suspension, the filtrate of the 17bNF toluene suspension, or the filtrate of the 17bNF methyl tert-butyl ether suspension, separately.

100 μl of the 17bNF ethanol solution were mixed with 100 μl of the filtrate of the 17bNF ethanol solution, 17bNF isopropyl alcohol suspension, 17bNF tetrahydrofuran solution, 17bNF ethyl acetate suspension, 17bNF acetone solution, 17bNF isobutyl alcohol solution, 17bNF isopropyl acetate solution, 17bNF 2-butanone solution, the filtrate of the 17bNF toluene suspension or the filtrate of the 17bNF methyl tert-butyl ether suspension separately.

100 μl of the 17bNF isopropyl alcohol suspension were mixed with 100 μl of the filtrate of the 17bNF ethanol solution, 17bNF tetrahydrofuran solution, 17bNF acetone solution, 17bNF isobutyl alcohol solution, 17bNF isopropyl acetate solution, 17bNF 2-butanone solution, 17bNF isopropyl alcohol suspension, the filtrate of the 17bNF ethyl acetate suspension, the filtrate of the 17bNF toluene suspension, or the filtrate of the 17bNF methyl tert-butyl ether suspension 100 μl separately.

100 μl of the filtrate of the 17bNF isopropyl alcohol suspension were mixed with 100 μl of the 17bNF tetrahydrofuran solution, 17bNF acetone solution, 17bNF isobutyl alcohol solution, 17bNF isopropyl acetate solution, 17bNF 2-butanone solution, the filtrate of the 17bNF isopropyl alcohol suspension, the filtrate of the 17bNF ethyl acetate suspension, the filtrate of the 17bNF acetonitrile suspension, or the filtrate of the 17bNF toluene suspension, separately.

100 μl of the filtrate of the 17bNF tetrahydrofuran solution were mixed with 100 μl of the filtrate of the 17bNF tetrahydrofuran solution, 17bNF acetone solution, 17bNF isobutyl alcohol solution, 17bNF isopropyl acetate solution, 17bNF 2-butanone solution, the filtrate of the 17bNF ethyl acetate suspension, the filtrate of the 17bNF acetonitrile suspension, the filtrate of the 17bNF toluene suspension, or the filtrate of the 17bNF methyl tert-butyl ether suspension, separately.

100 μl of the filtrate the 17bNF ethyl acetate suspension were mixed with 100 μl of the filtrate of the 17bNF ethyl acetate suspension, 17bNF acetone solution, 17bNF 2-butanone solution, or the filtrate of the 17bNF acetonitrile suspension, separately.

100 μl of the filtrate of the 17bNF acetone solution were mixed with 100 μl of the 17bNF acetone solution, 17bNF isobutyl alcohol solution, 17bNF isopropyl acetate solution, 17bNF 2-butanone solution, or the filtrate of the 17bNF toluene suspension, separately.

100 μl of the filtrate of the 17bNF isobutyl alcohol solution were mixed with 100 μl of the 17bNF isobutyl alcohol solution, 17bNF isopropyl acetate solution, 17bNF isopropyl acetate solution, the filtrate of the 17bNF acetonitrile suspension, 17bNF 2-butanone solution, the filtrate of the 17bNF toluene suspension, the filtrate of the 17bNF water suspension, or the filtrate of the 17bNF methyl tert-butyl ether suspension, separately.

100 μl of the filtrate of the 17bNF isopropyl acetate solution were mixed with 100 μl of the 17bNF 2-butanone solution.

100 μl of the filtrate of the 17bNF acetonitrile suspension were mixed with 100 μl of the 17bNF 2-butanone solution, or the filtrate of the 17bNF methyl tert-butyl ether suspension, separately.

100 μl of the filtrate of the 17bNF 2-butanone solution were mixed with 100 μl of the 17bNF 2-butanone solution, the filtrate of the 17bNF toluene suspension, the filtrate of the 17bNF water suspension, or the filtrate of the 17bNF methyl tert-butyl ether suspension, separately.

Each mixed solution or suspension was put into a 96-well plate and the 96-well plate was sealed with a sealing membrane with some small pinholes on it. The plate was then placed in a fume hood under atmospheric conditions to evaporate to obtain the Crystal Form I of 17bNF (17bNF-I).

Example 3—Preparation of 17bNF Crystal Form I (17bNF-I)

As described in Table 1, 0.5 mL of filtrates of the solutions of 17bNF in methanol, ethanol, tetrahydrofuran, ethyl acetate, acetone or 2-butanone, separately, was placed into test tubes, and the test tubes were placed in a fume hood to dry the filtrates at room temperature and obtain 17bNF Crystal Form I (17bNF-I).

Example 4—Preparation of 17bNF Crystal Form I (17bNF-I)

As described in Table 1, 1 mL of suspension of 17bNF-0 in diethyl ether was stirred and beat for 3 days at room temperature. The suspension was then filtered, and the solids were dried to obtain 17bNF Crystal Form I (17bNF-I).

Example 5—Preparation of 17bNF Crystal Form II (17bNF-II)

As described in Table 1, 1 mL of 17bNF-0 suspension in water was stirred and beat for 3 days at room temperature. The suspension was then filtered, and the solids were dried to obtain 17bNF Crystal Form II (17bNF-II).

Example 6—Preparation of 17bNF Crystal Form III (17bNF-III)

As described in Table 1, 1 mL of 17bNF-0 suspension in acetonitrile was stirred and beat for 3 days at room temperature. The suspension was then filtered, and the solids were dried to obtain 17bNF Crystal Form VIII. 17bNF Crystal Form VIII was heated to 160° C. by DSC to lose solvent and obtain 17bNF Crystal Form III (17bNF-III).

Example 7—Preparation of 17bNF Crystal Form IV (17bNF-IV)

As described in Table 1, a suspension of 17bNF-0 (180 mg) in methyl tertiary butyl ether (3 mL) was prepared, 3 mg of 17bNF Crystal Form IV as seed crystal were added, and the suspension was stirred at room temperature. After 2 days, the suspension was then filtered to collect the solids and obtain 17bNF Crystal Form IV (17bNF-IV).

Example 8—Preparation of 17bNF Crystal Form V

As described in Table 1, 1 mL of 17bNF-0 suspension in isopropanol was stirred and beat for 3 days at room temperature. The suspension was then filtered to obtain solids which were then, dried to obtain 17bNF Crystal Form V.

Example 9—Preparation of 17bNF Crystal Form VI

As described in Table 1, solutions were mixed and filtered to obtain filtrates. 100 μl of the filtrate of 17bNF-0 methanol solution were mixed with 100 μl of the filtrate of 17bNF 2-butanone solution, and the mixture was placed into a 96-well plate. The 96-well plate was sealed by a sealing film with some small pinholes on it and placed in a fume hood to dry the filtrates in natural environment and obtain 17bNF Crystal Form VI.

Example 10—Preparation of 17bNF Crystal Form VII

As described in Table 1, 1 mL of suspension of 17bNF-0 in ethyl acetate was stirred and beat for 3 days at room temperature. The suspension was filtered, and the solids were, dried to obtain 17bNF Crystal Form VII.

Example 11—Preparation of 17bNF Crystal Form VII 20.3 mg of 17bNF-0 were dissolved in 0.1 mL of tetrahydrofuran, and some anti-solvent (0.4 mL of diethyl ether) was added. The mixture was stirred to obtain precipitates which were then filtered to obtain 17bNF Crystal Form VII.

Example 12—Preparation of 17bNF Crystal Form VII

As described in Table 1, solutions were mixed and filtered to obtain filtrates. 100 μl of the filtrates of 17bNF ethyl acetate solution were mixed with 100 μl of the filtrates of 17bNF isopropyl acetate solution. The mixture was placed into a 96-well plate which was then sealed by sealing film with small pinholes on it, and the 96-well plate was placed in a fume hood to dry the filtrates in natural environment and obtain 17bNF Crystal Form VII.

Example 13—Preparation of 17bNF Crystal Form VIII

As described in Table 1, 1 mL of suspension of 17bNF-0 in acetonitrile was stirred and beat for 3 days at room temperature and then filtered to obtain solids which were then dried to obtain 17bNF Crystal Form VIII.

Example 14—Preparation of 17bNF Crystal Form IX

As described in Table 1, 1 mL of the suspension of 17bNF-0 in methyl benzene was stirred and beat for 3 days at room temperature and then filtered to obtain solids which were then dried to obtain 17bNF Crystal Form IX.

Example 15—Preparation of 17bNF Crystal Form X

As described in Table 1, solutions were mixed and filtered to obtain filtrates. 100 μl of the filtrates of 17bNF ethyl acetate solution were mixed with 100 μl of the filtrates of 17bNF isobutanol solution. The mixture was placed into a 96-well plate which was then sealed by sealing film with small pinholes on it. The 96-well plate was then placed in a fume hood to dry the filtrates in natural environment and obtain 17bNF Crystal Form X.

Example 16—Preparation of 17bNF Crystal Form XI

As described in Table 1, solutions were mixed and filtered to obtain filtrates. 100 μl of the filtrates of 17bNF ethyl acetate solution were mixed with 100 μl of filtrates of 17bNF methyl tertiary butyl ether solution. The mixture was placed into a 96-well plate which was then sealed by sealing film with small pinholes on it. The 96-well plate was then place in a fume hood to dry the filtrates in natural environment and obtain 17bNF Crystal Form XI.

Example 17—Preparation of 17bNF Crystal Form XII

As described in Table 1, solutions were mixed and filtered to obtain filtrates. 100 μl of the filtrates of 17bNF acetone solution were mixed with 100 μl of the filtrates of 17bNF methyl tertiary butyl ether solution. The mixture was placed into a 96-well plate which was then sealed by sealing film with small pinholes on it. The 96-well plate was then place in a fume hood to dry the filtrates in natural environment and obtain 17bNF Crystal Form XII.

Example 18—Preparation of 17bNF Crystal Form XIII

As described in Table 1, 0.5 ml of the filtrate of the 17bNF solution in isopropyl acetate was placed into a test tube which was then put in a fume hood to dry the filtrate at room temperature and obtain 17bNF Crystal Form XIII.

Example 19—Preparation of 17bNF Crystal Form XIV

Some 20.8 mg of 17bNF were dissolved in 0.3 mL of acetone, and an anti-solvent (1.54 mL of diethyl ether) was then added. The mixture was stirred to obtain precipitates which were then filtered to obtain 17bNF Crystal Form XIV.

Example 20—Preparation of Amorphous 17bNF

As described in Table 1, solutions were mixed and filtered to obtain filtrates. 100 μl of the filtrates of 17bNF acetonitrile solution were mixed with 100 μl of the filtrates of 17bNF methyl benzene solution. The mixture was placed into a 96-well plate which was then sealed by a sealing film with small pinholes on it. The 96-well plate was then placed in a fume hood to dry the filtrates in natural environment and obtain amorphous 17bNF.

Example 21—In Vivo Efficacy Test of 17bNF Crystal Form 0 and Form II (17bNF-0 and 17bNF-II)

Figure 42A:
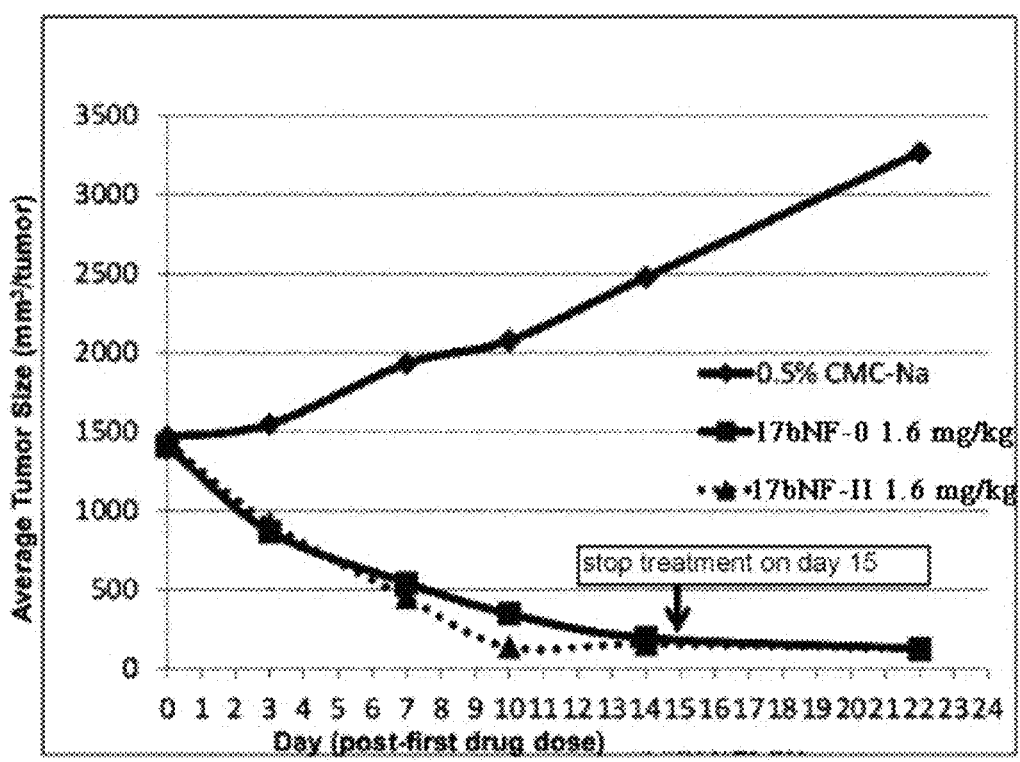
Figure 42B:
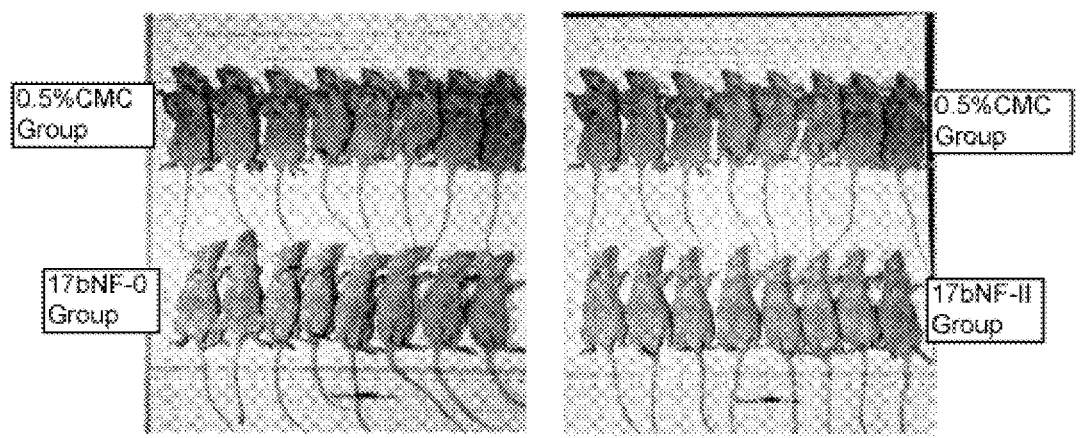
Figure 42C:
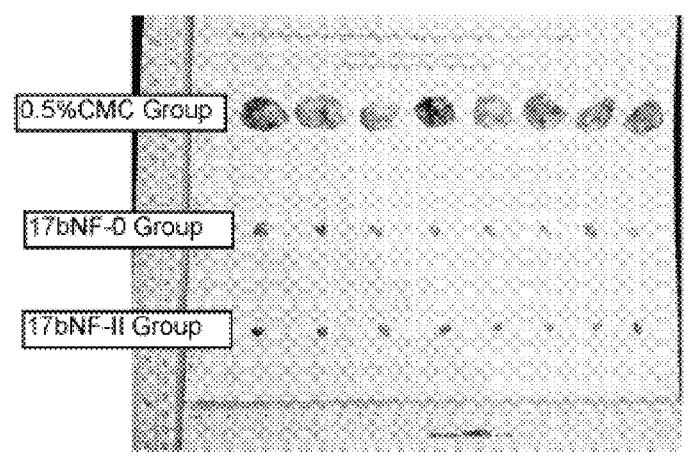

Human gastric cancer cells MGC-803 were subcutaneously planted into the armpit of nude mice. The test drugs 17bNF-0 and 17bNF-II were separately administered orally when the average tumor volume reached 1450 mm$^3$. Drugs were given once a day, six times every week until the 15th day. CMC (drug-carrier; 0.5%) was used as the blank control. Tumor volumes were measured once about every three days (FIG. 42A), and the nude mice were photographed on the 22th day (FIG. 42B), and the nude mice were sacrificed on the 22th day. The tumors were dissected out from the nude mice and photographed (FIG. 42C). The results show that 17bNF-0 and 17bNF-II have very high anticancer activities in nude mice.

Example 22—In Vivo Efficacy Test-1 of 17bNF Crystal Form 0 to Form IV (17bNF-0 to 17bNF-IV)

Figure 43:
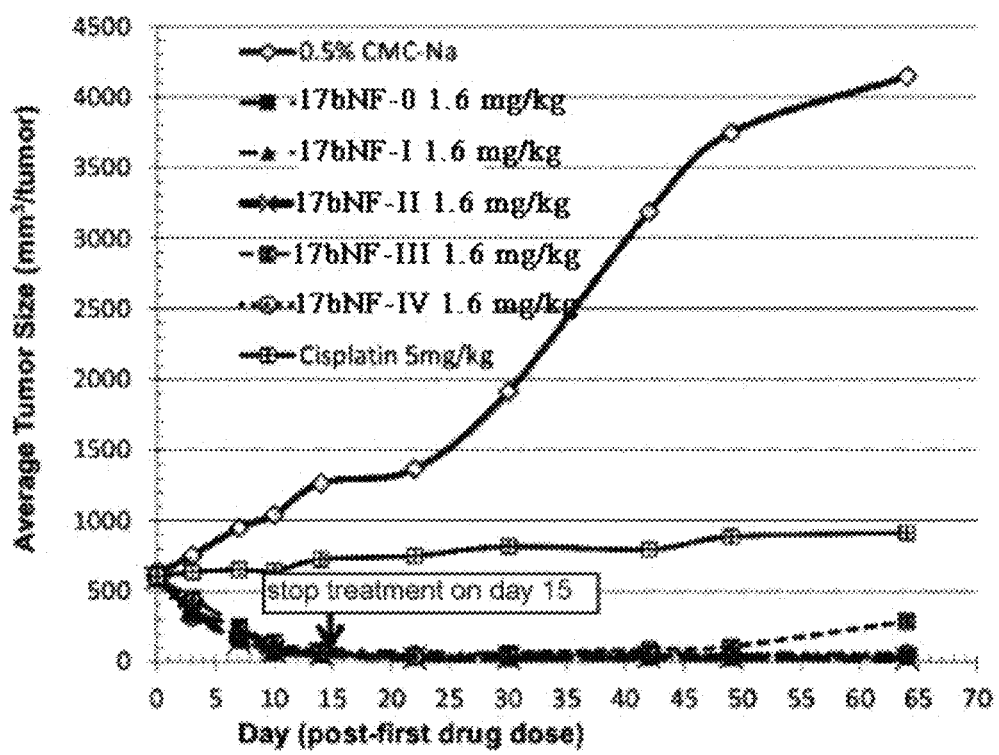
Figure 44:
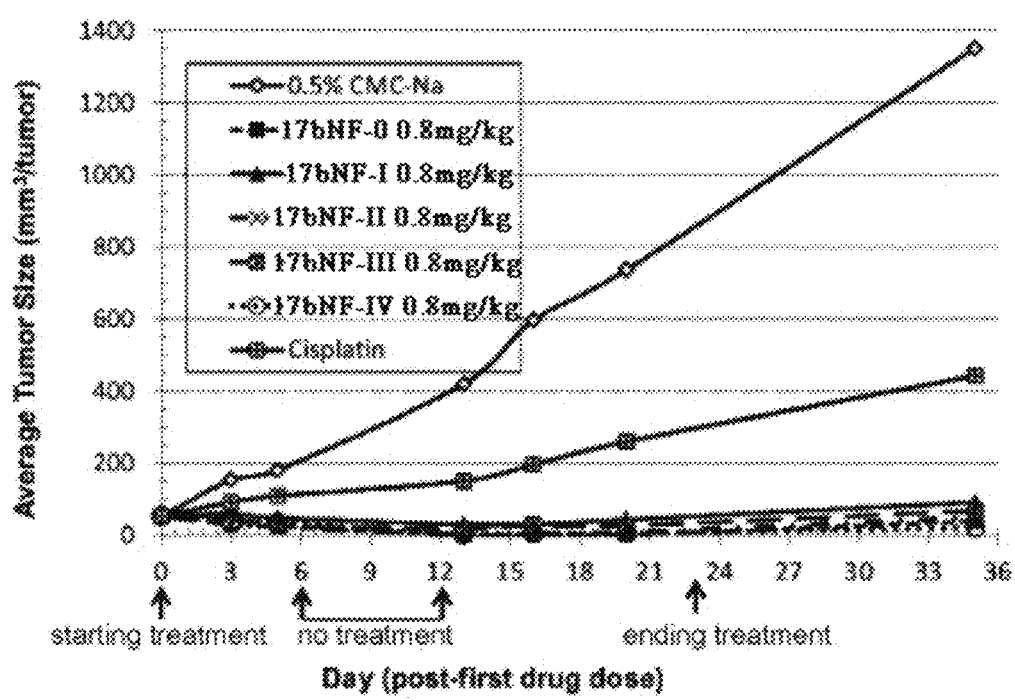

Human gastric cancer cells MGC-803 were subcutaneously planted into the armpit of nude mice. The test drugs 17bNF-0 to 17bNF-IV were separately administered orally when the average tumor volume reached ~600 mm$^3$. Drugs were given once a day, six times every week until the 15th day. Nude mice injected intraperitoneally with 5 mg/kg Cisplatin once every five days were as positive control. CMC (drug-carrier; 0.5%) was used as the blank control. Tumor volumes were measured once about every three days (FIG. 43). The results show that 17bNF-0 to 17bNF-IV have very high anticancer activities in nude mice.

Example 23—In Vivo Efficacy Test-2 of 17bNF Crystal Form 0 to Form IV (17bNF-0 to 17bNF-IV)

Human gastric cancer cells MGC-803 were subcutaneously planted into the armpit of nude mice. The test drugs 17bNF-0 to 17bNF-IV were separately administered orally when the tumor average volume reach ~100 mm$^3$. Drugs were given once a day, six times every week until the 15th day. Nude mice injected intraperitoneally with 5 mg/kg Cisplatin once every five days were as positive control. CMC (drug-carrier; 0.5%) was used as the blank control. Tumor volumes were measured once about every three days (FIG. 43). The results show that 17bNF-0 to 17bNF-IV have very high anticancer activities in nude mice.

Example 24—the Result of Stability Testing of Different Crystal Forms

Figure 45:
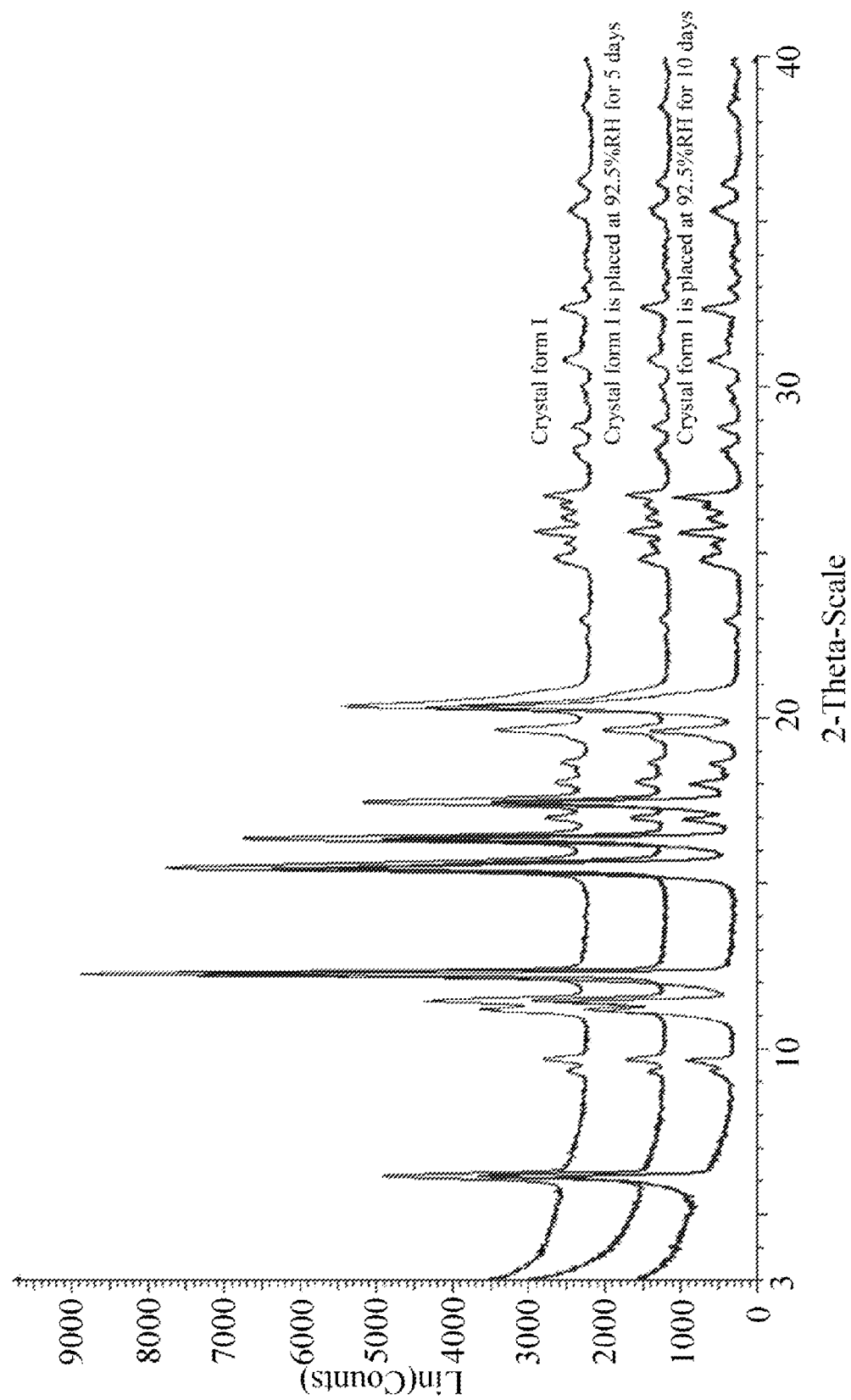
Figure 46:
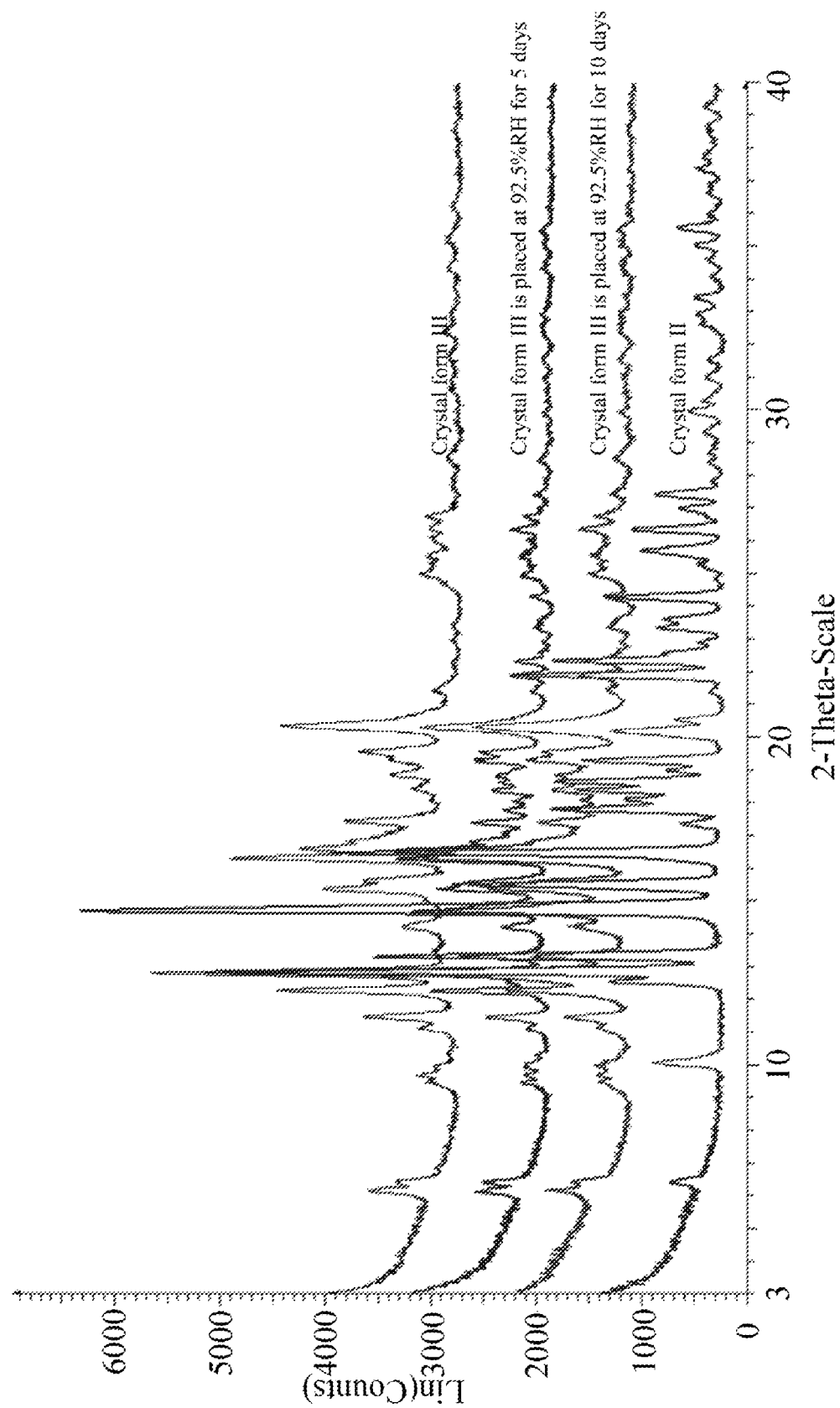
Figure 47:
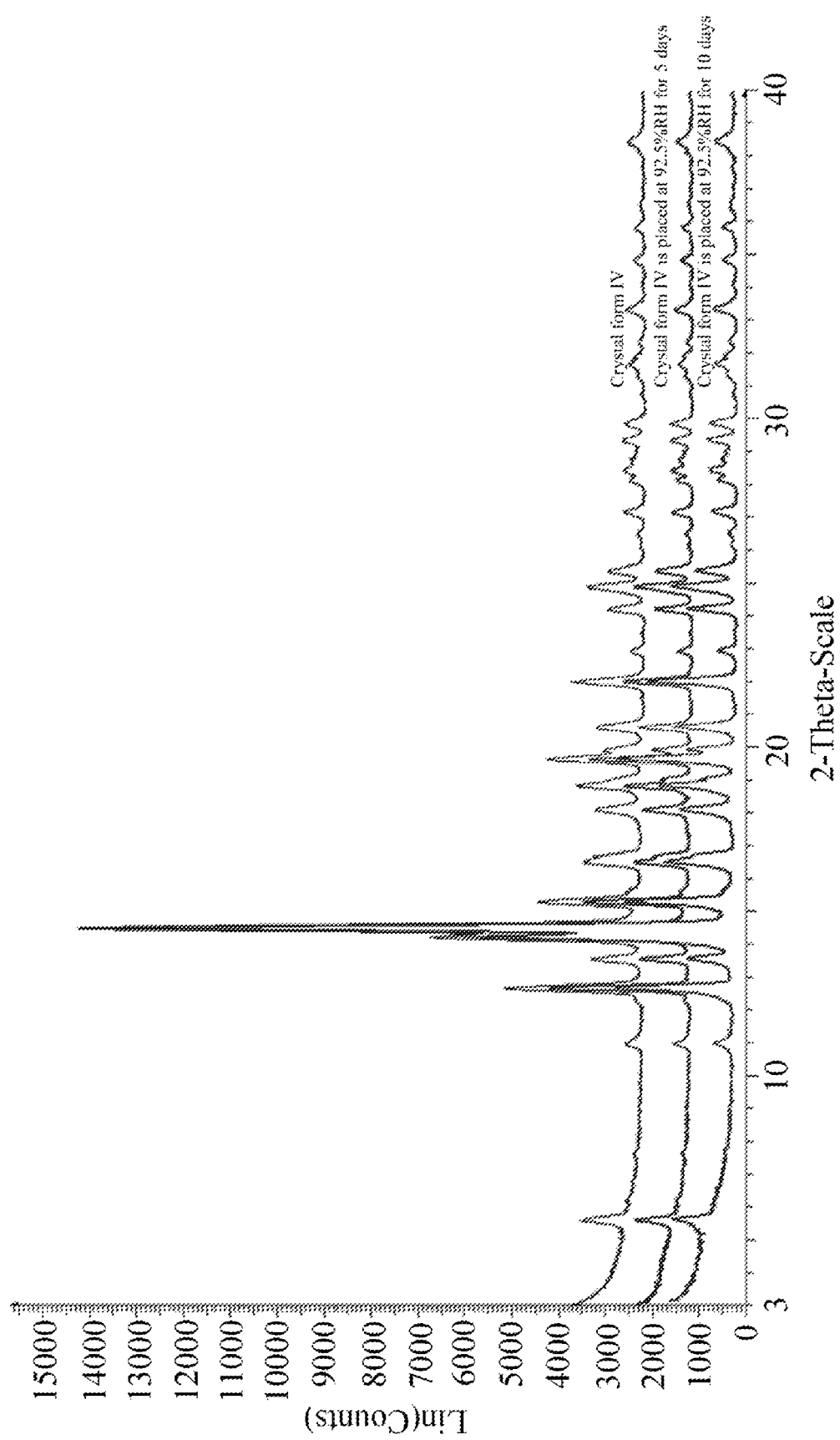

Samples of crystal forms I, III and IV were placed in an environment of 92.5% RH for 5 and 10 days, respectively, and tested with XRPD. The XRPD results show that crystal forms I and IV are stable and do not change, while some of the samples of crystal form III transform to crystal form II. The results are shown in FIGS. 45-47.

Example 25—the Data for Stability Testing of Crystal Form II

1. Stress Testing

Six samples of crystal form II (17bNF-II) (batch number: 20161203) were tested under three separate stress conditions: at a temperature of 60° C., at a humidity of 90%, and at a light intensity of 6500Lx; each condition tested over both 5 and 10 days (6 samples total). These samples were tested by X-ray powder diffraction (XRPD) in accordance with the Chinese Pharmacopeia 2015 edition.

Figure 48:
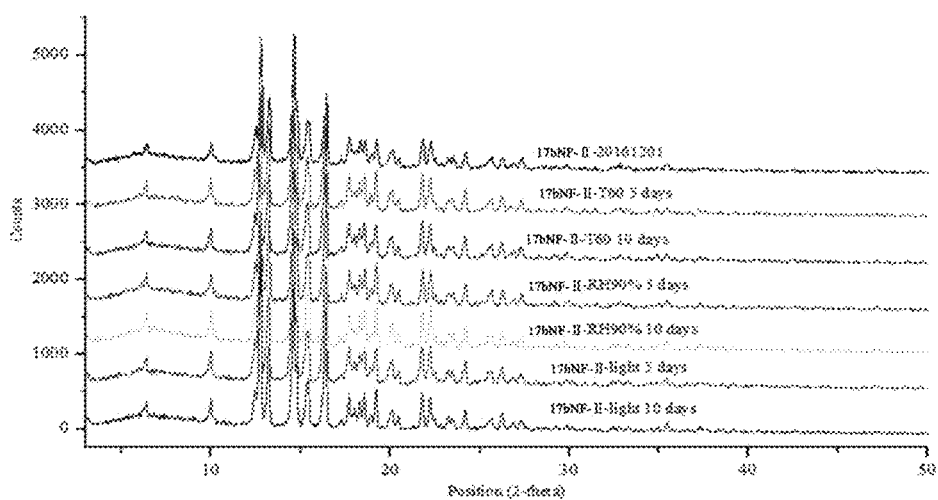

The results are shown in FIG. 48. The results show that the positions of diffraction peaks (2θ value), relative intensities and the total number of peaks in the XRPD spectra remain the same throughout stress testing, indicating that crystal form II (17bNF-II) is still stable at high temperature, high humidity and high light intensity.

2. Accelerated Testing

Samples of crystal form II (17bNF-II) (batch numbers: 20161201, 20161202, 20161203) were taken and placed at a temperature of 40° C. and humidity of 75% for 1, 2, 3 and 6 months, respectively. These samples were tested by X-ray powder diffraction (XRPD) in accordance with the Chinese Pharmacopeia of 2015 edition.

Figure 49:
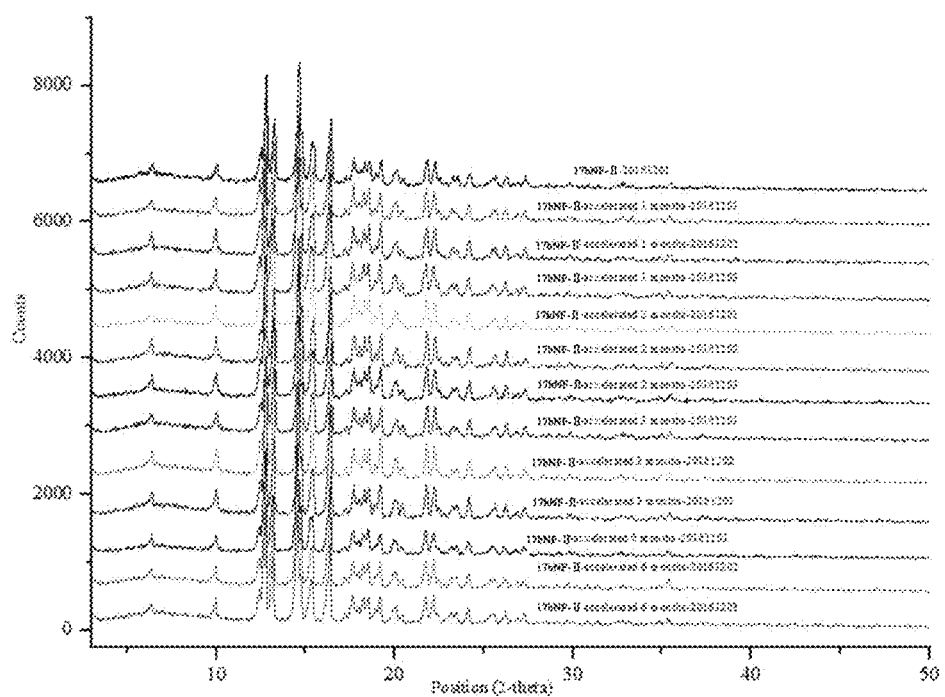

The results are shown in FIG. 49. The results show that the positions of diffraction peaks (2θ value), relative intensities, and the total number of peaks in the XRPD spectra remain the same throughout accelerated testing, indicating that crystal form II (17bNF-II) is stable at high temperature, high humidity and high light intensity.

3. Long-Term Testing

Samples of crystal form II (17bNF-II) (batch number: 20161201, 20161202, 20161203) were taken and placed at a temperature of 25° C. and humidity of 60% for 3, 6, 9, 12, 18, and 24 months, respectively. These samples were tested by X-ray powder diffraction (XRPD) in accordance with the Chinese Pharmacopeia 2015 edition.

Figure 50A:
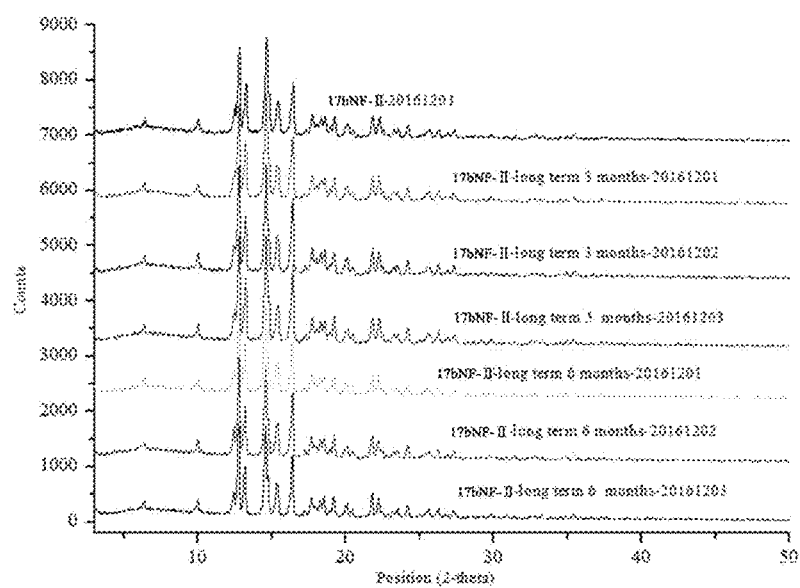
Figure 50B:
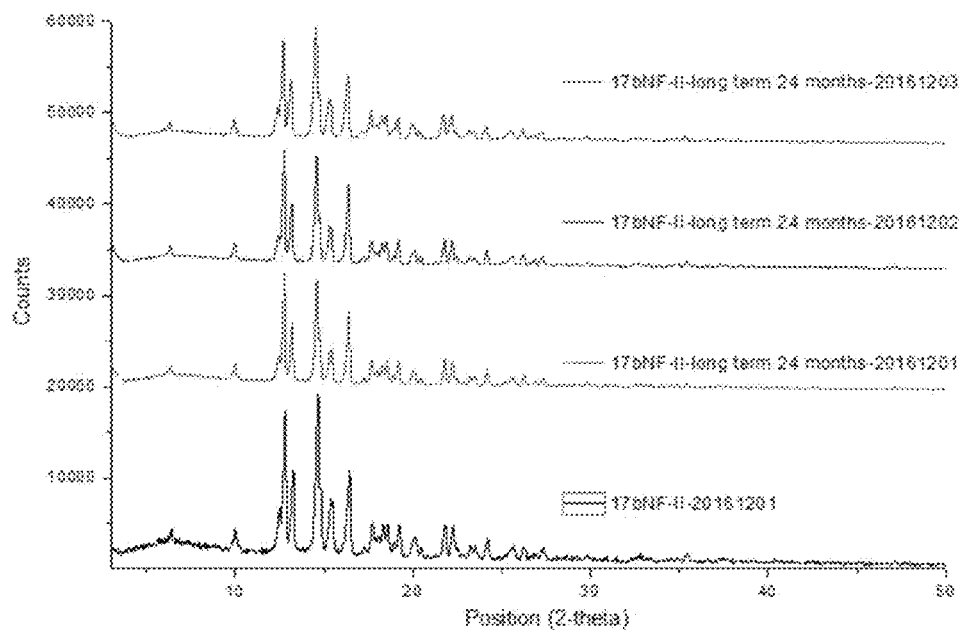

The results are shown in FIGS. 50A and 50B. The results show that the positions of diffraction peaks (2θ value), relative intensities, and the total number of peaks in XRPD spectra remain the same throughout long-term testing, indicating that crystal form 17bNF-II is stable at high temperature, high humidity and high light intensity.

After 24 months of long-term testing, the results show that crystal form II(17bNF-II) is still stable at high temperature, high humidity and high light intensity.

Example 26—Suspended Crystal Transformation Testing

Figure 51:
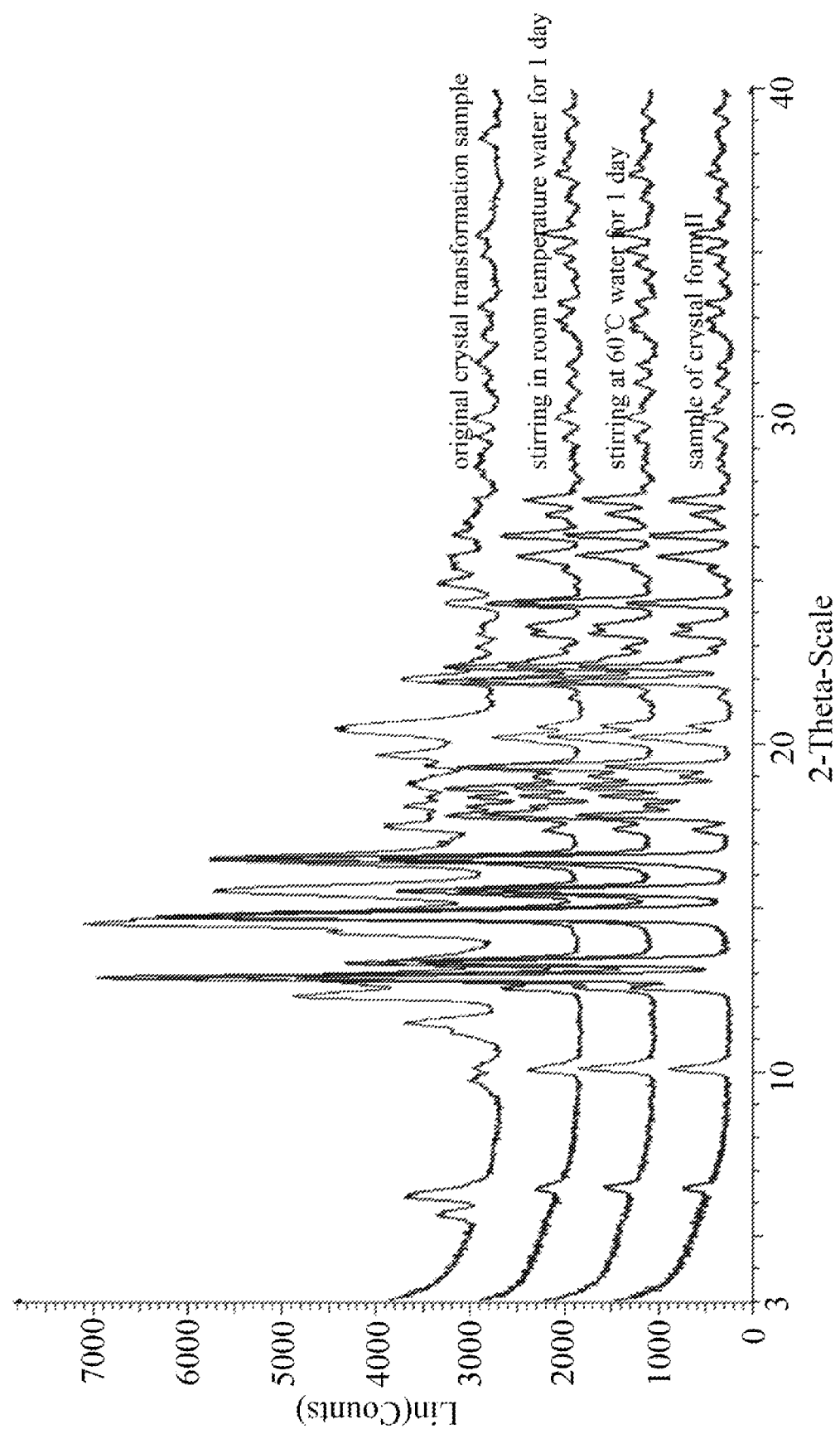
Figure 52:
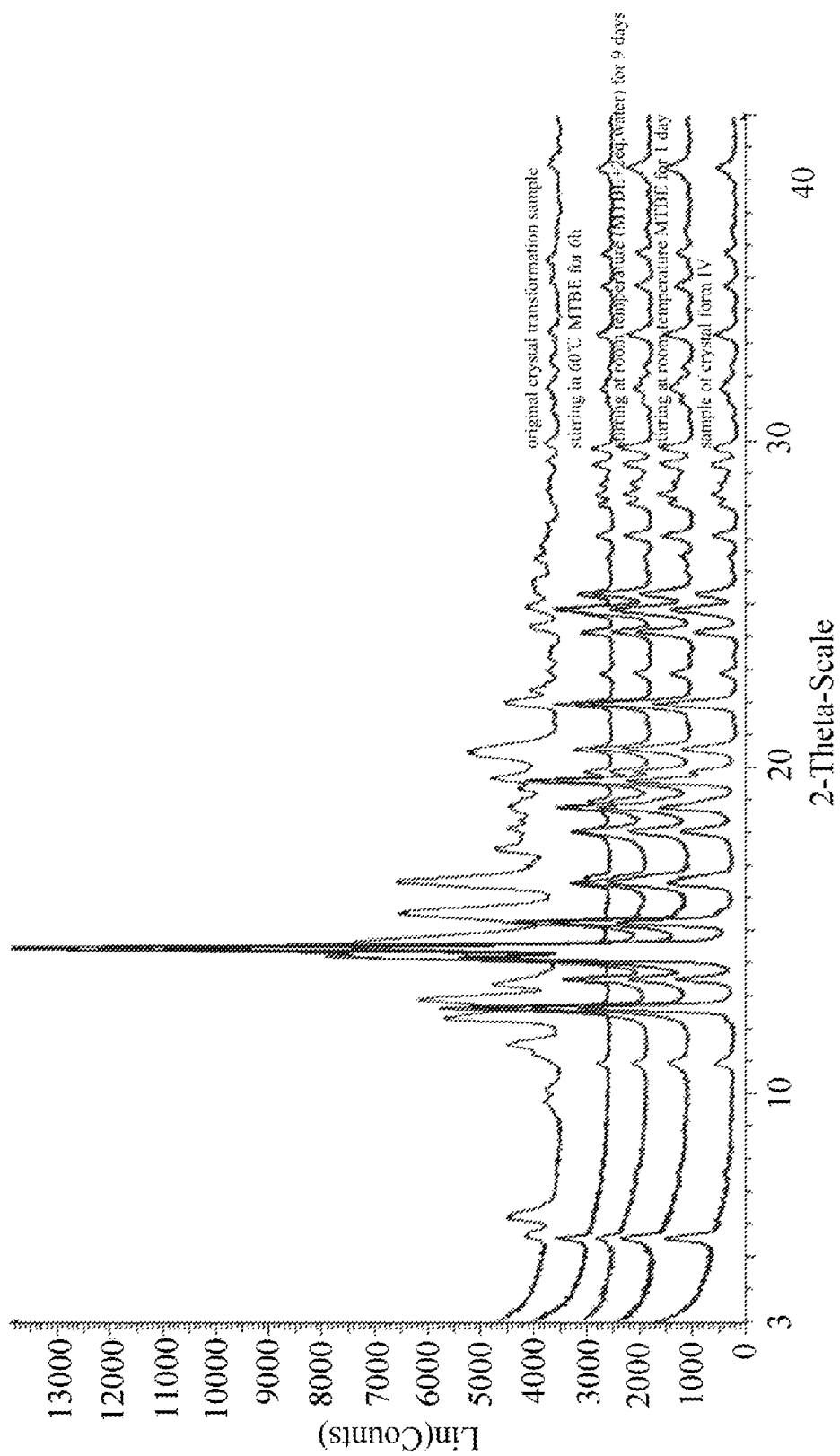

The four different crystal forms (17bNF-I to 17bNF-IV) were mixed in equal proportion and stirred under different conditions and times. The samples were filtered and the solids were collected for XRPD testing, the results of crystal transformation testing are shown in Table 2 and FIGS. 51-52.

TABLE 2

The results of suspended crystal transformation testing

| Testing number | Solvent | Temperature | Stirring time | Crystal Transformation |
|---|---|---|---|---|
| 1 | 1 ml of water | Room temperature | 1 day | Crystal form II |
| 2 | 1 ml of water | 60° C. | 1 day | Crystal form II |
| 3 | 1 ml of MTBE + 2 μl of water | Room temperature | 9 days | Crystal form IV |
| 4 | 1 ml of MTBE | 60° C. | 6 hours | Crystal form IV |
| 5 | 1 ml of MTBE | Room temperature | 1 day | Crystal form IV |

TABLE 3

Purity and content data for different crystal forms

| Crystal form | Content (%) | Purity (%) |
|---|---|---|
| 17bNF-O | 98.72 | 98.95 |
| 17bNF-I | 97.09 | 98.83 |
| 17bNF-II | 95.91 | 98.96 |
| 17bNF-III | 95.51 | 95.45 |
| 17bNF-IV | 98.54 | 98.69 |

What is claimed is:

1. Crystal Form of 17bNF is 17β-neriifolin, comprising:
    i) a non-solvated Crystal Form 17bNF-I which has a powder X-ray diffraction pattern comprising characteristic peaks with 2θ values of 6.1°±0.2°, 11.2°±0.2°, 11.4°±0.2°, 12.2°±0.2°, 15.5°±0.2°, 16.4°±0.2°, 17.5°±0.2°, 19.7°±0.2°, and 20.4°±0.2°;
    ii) a non-solvated Crystal Form 17bNF-II which has a powder X-ray diffraction pattern comprising characteristic peaks with 2θ values of 6.4°±0.2°, 10.1°±0.2°, 12.6°±0.2°, 12.8°±0.2°, 13.3°±0.2°, 14.8°±0.2°, 15.5°±0.2°, 16.5°±0.2°, 17.8°±0.2°, 18.1°±0.2°, 18.4°±0.2°, 18.7°±0.2°, 19.3°±0.2°, 20.2°±0.2°, 21.9°±0.2°, 22.4°±0.2°, 23.4°±0.2°, 24.3°±0.2°, 25.8°±0.2°, 26.4°±0.2°, 27.0°±0.2° and 27.5°±0.2°; or
    iii) a non-solvated Crystal Form 17bNF-IV which has a powder X-ray diffraction pattern comprising characteristic peaks with 2θ values of 5.6°±0.2°, 12.6°±0.2°, 13.5°±0.2°, 14.2°±0.2°, 14.5°±0.2°, 15.3°±0.2°, 16.5°±0.2°, 18.1°±0.2°, 18.8°±0.2°, 19.6°±0.2°, 19.9°±0.2°, 20.6°±0.2°, 22.0°±0.2°, 24.2°±0.2°, 24.9°±0.2° and 25.4°±0.2°.

Figure 4:
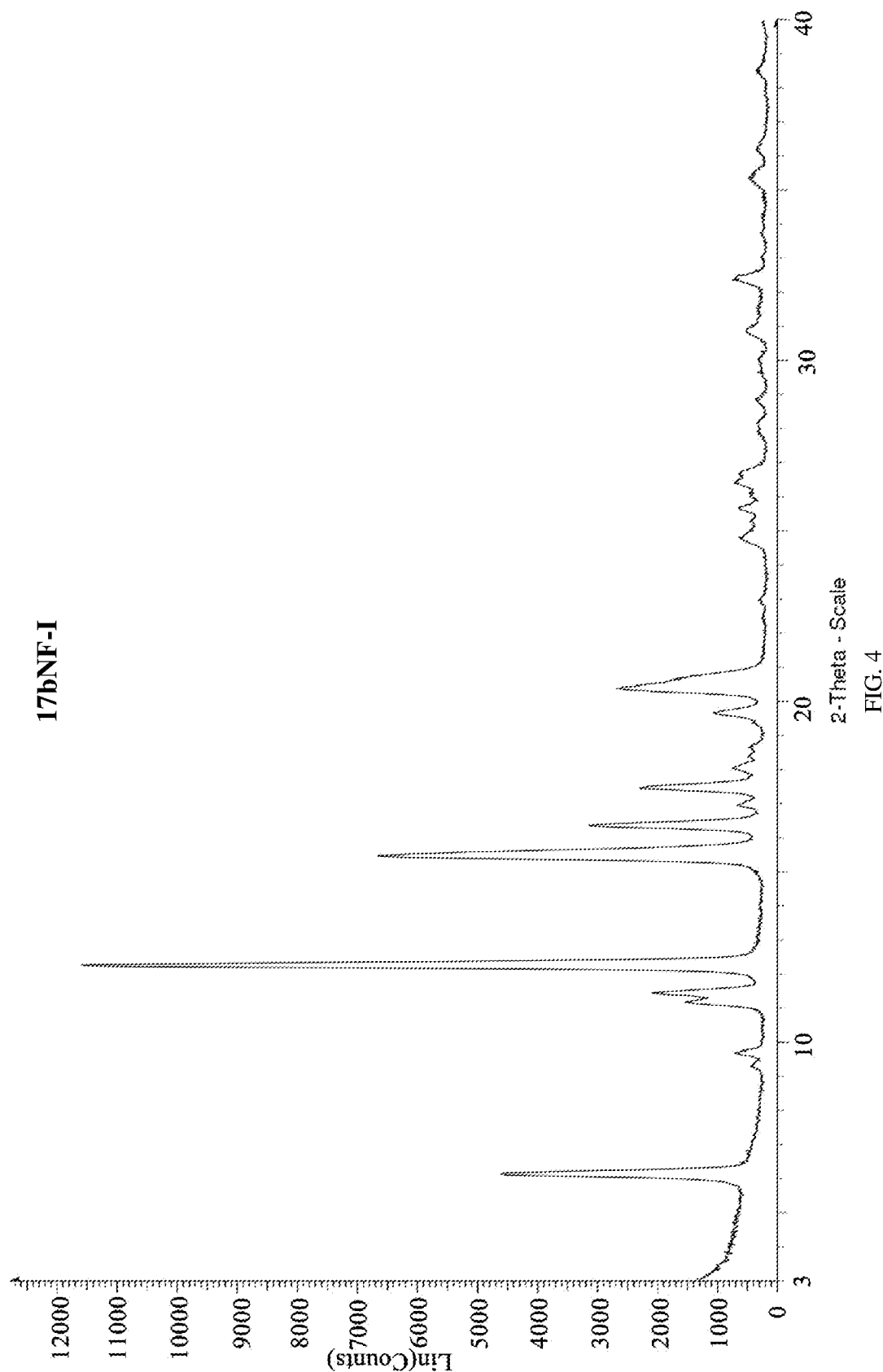
Figure 5:
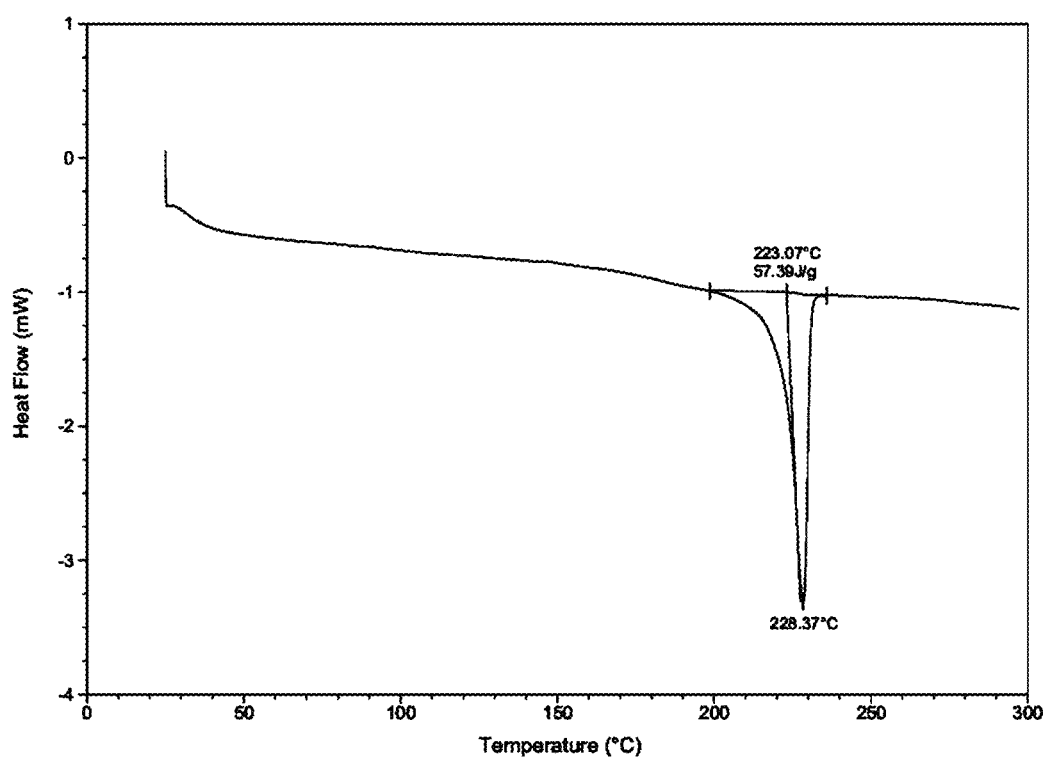
Figure 6:
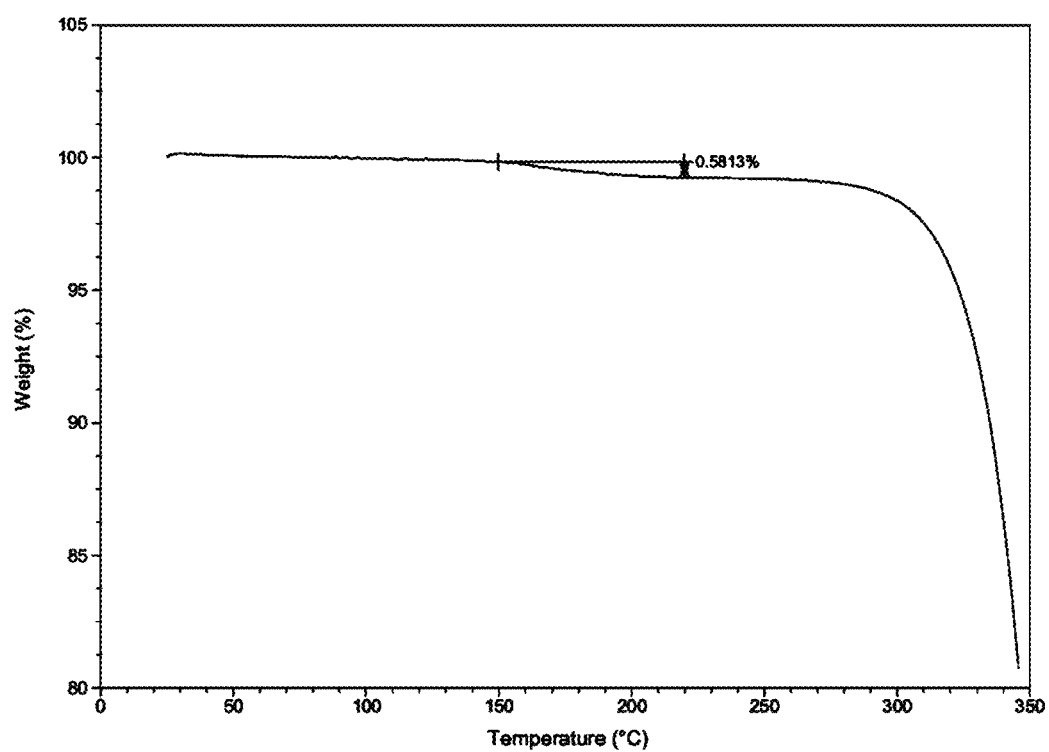

2. The Crystal Form of 17bNF according to claim 1, wherein said Crystal Form 17bNF-I, further has at least one of following characteristics: a differential scanning calorimetry spectrum has an endothermic peak at 218-238° C.; and a thermogravimetric analysis spectrum has a weight loss of ~0.6% before 250° C.; the corresponding characteristic spectra are shown in FIGS. 4-6.

Figure 7:
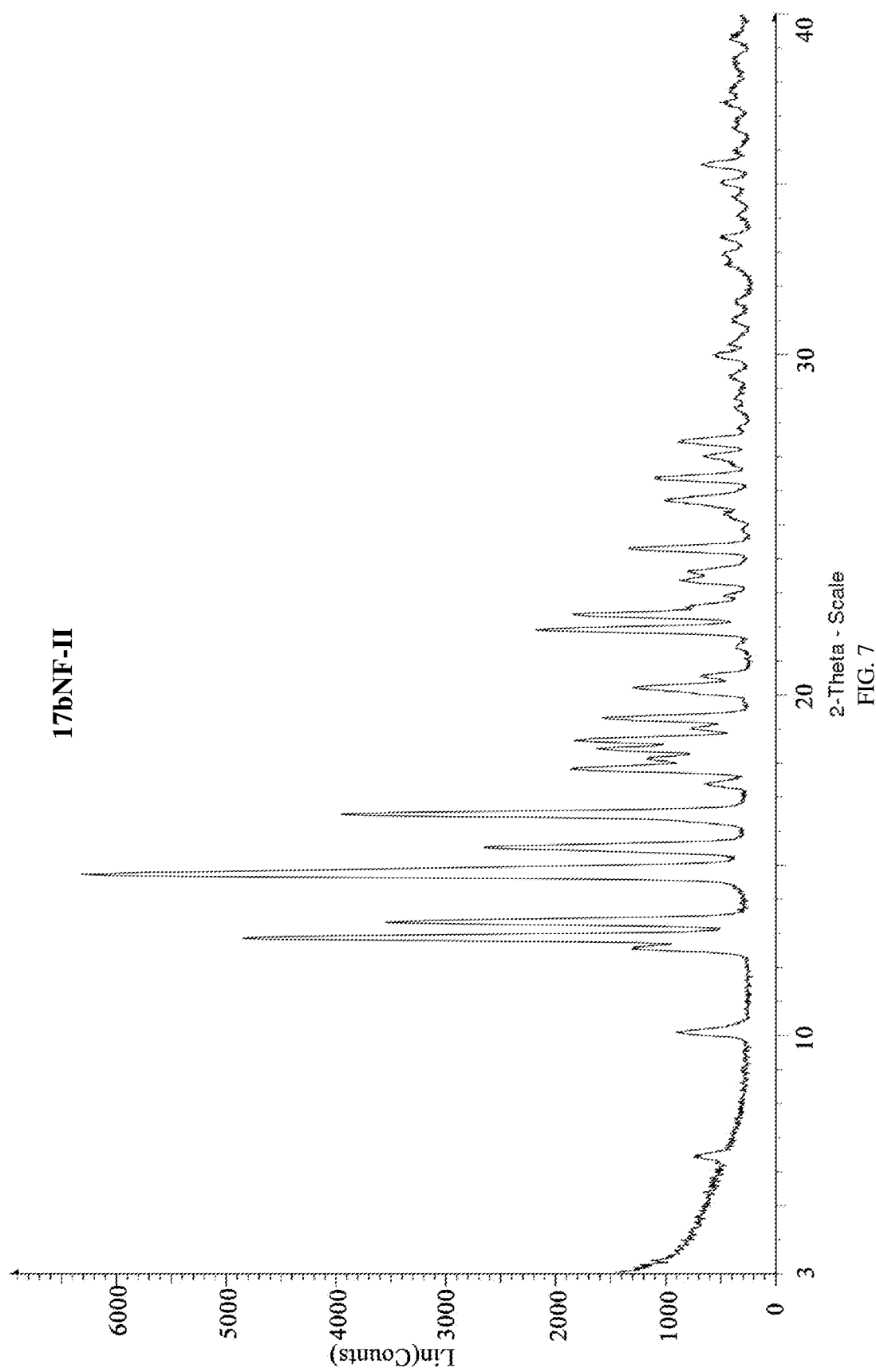
Figure 8:
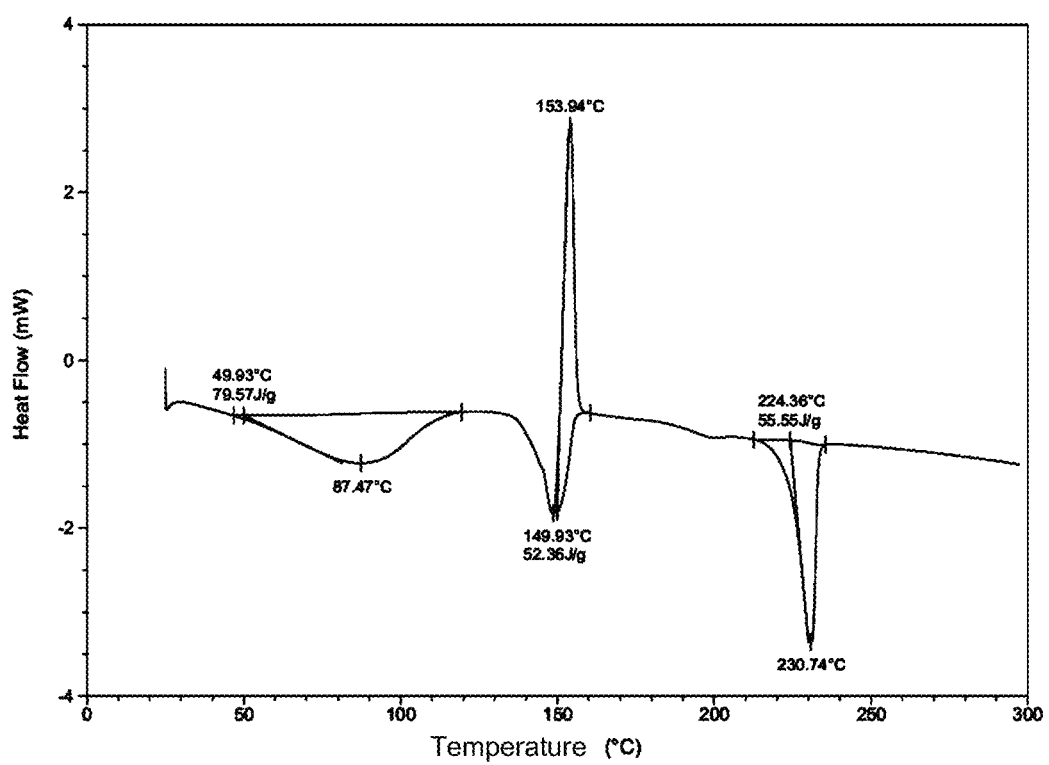
Figure 9:
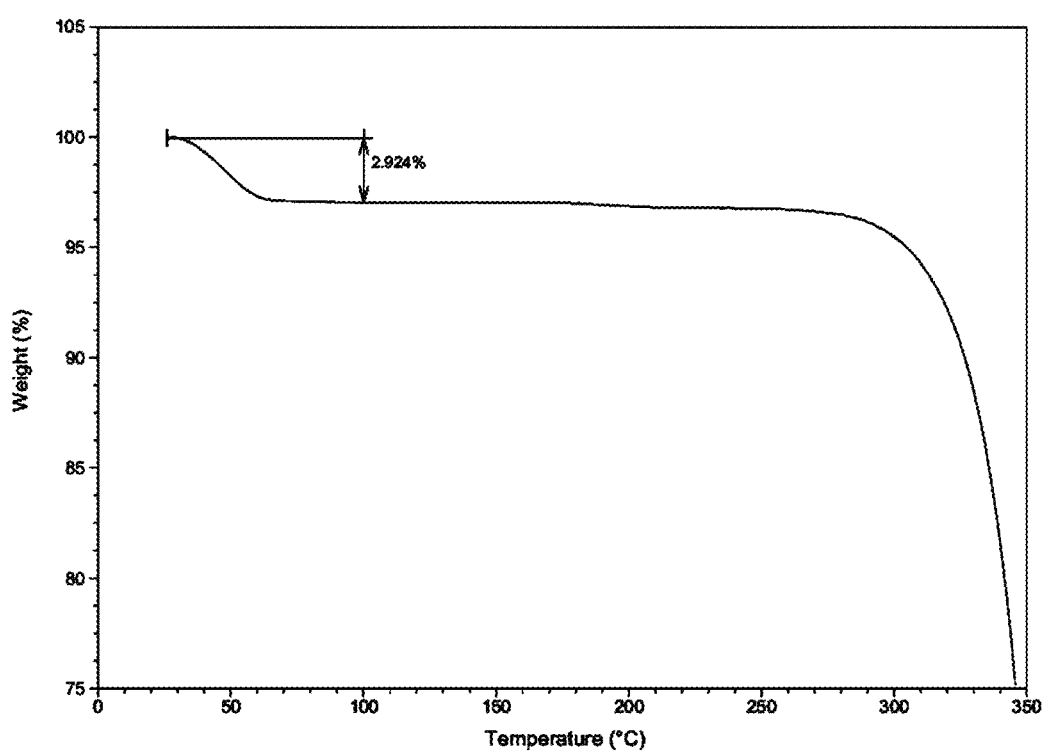
Figure 10:
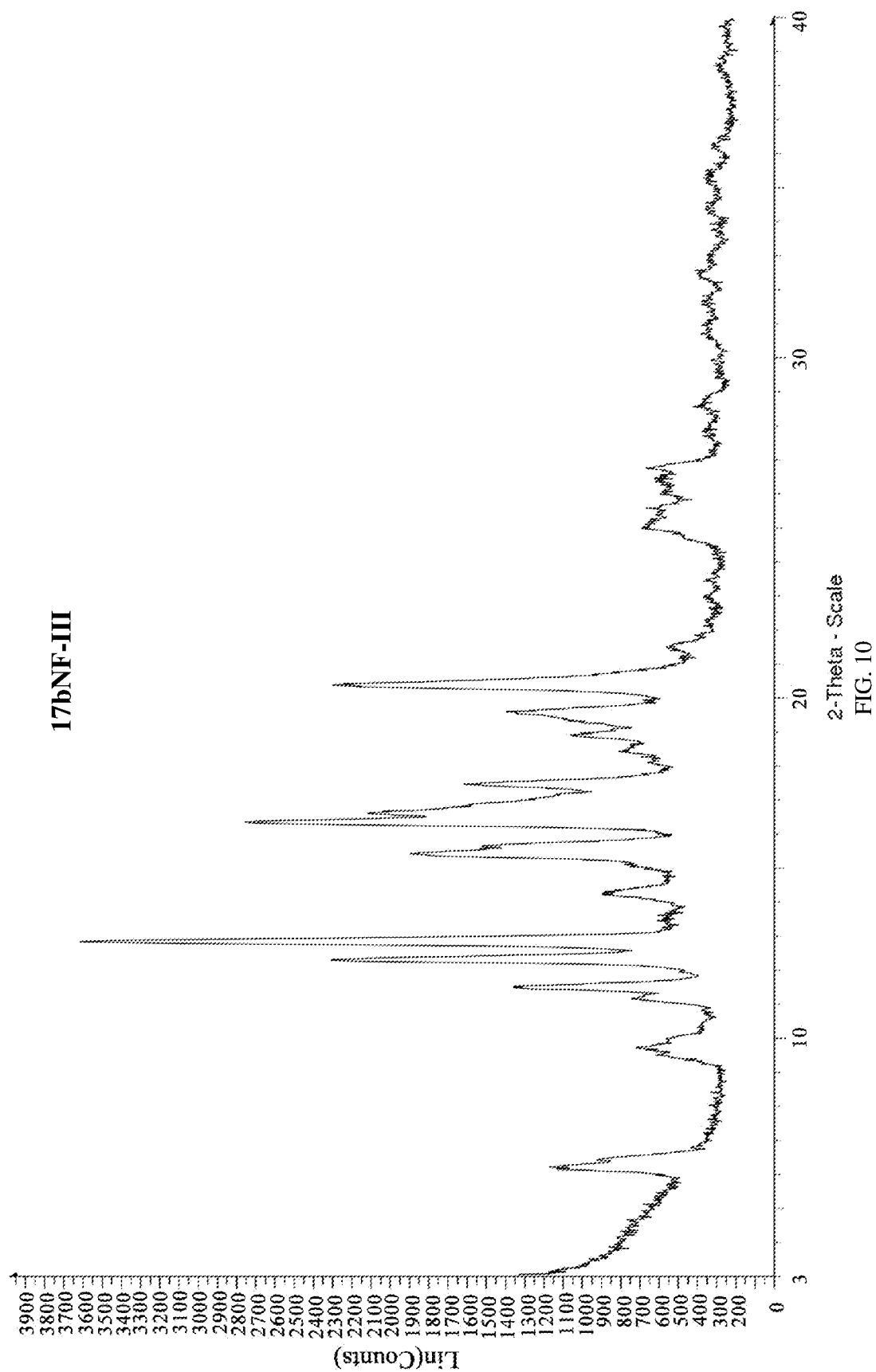
Figure 11:
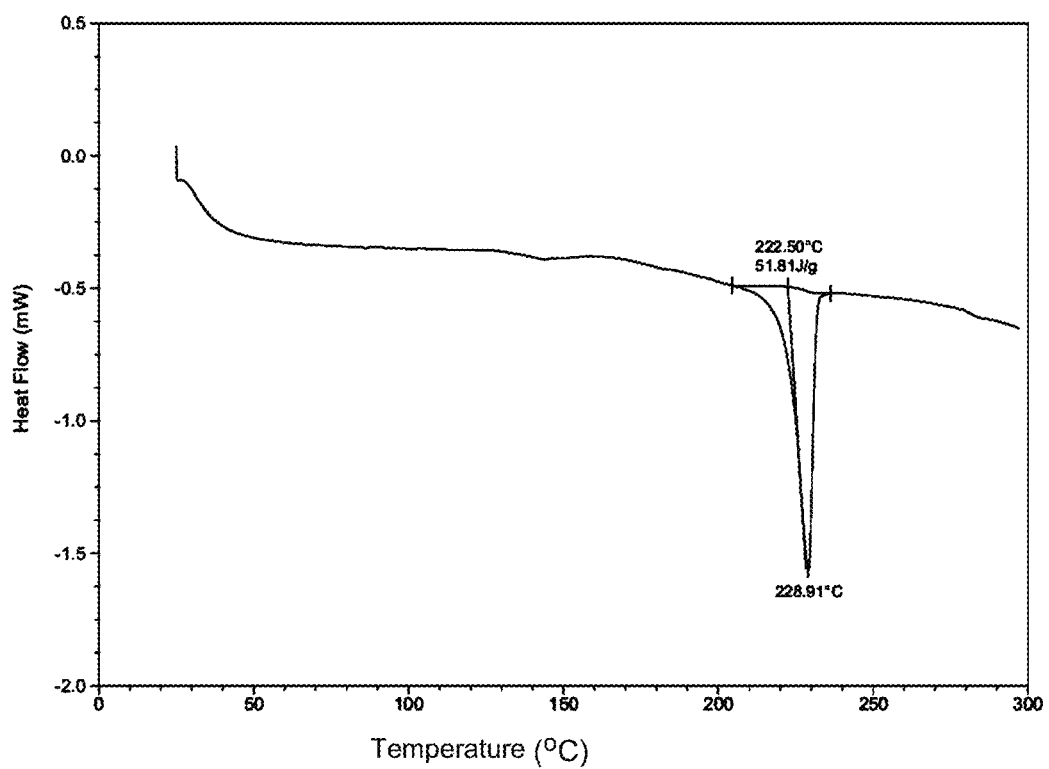
Figure 12:
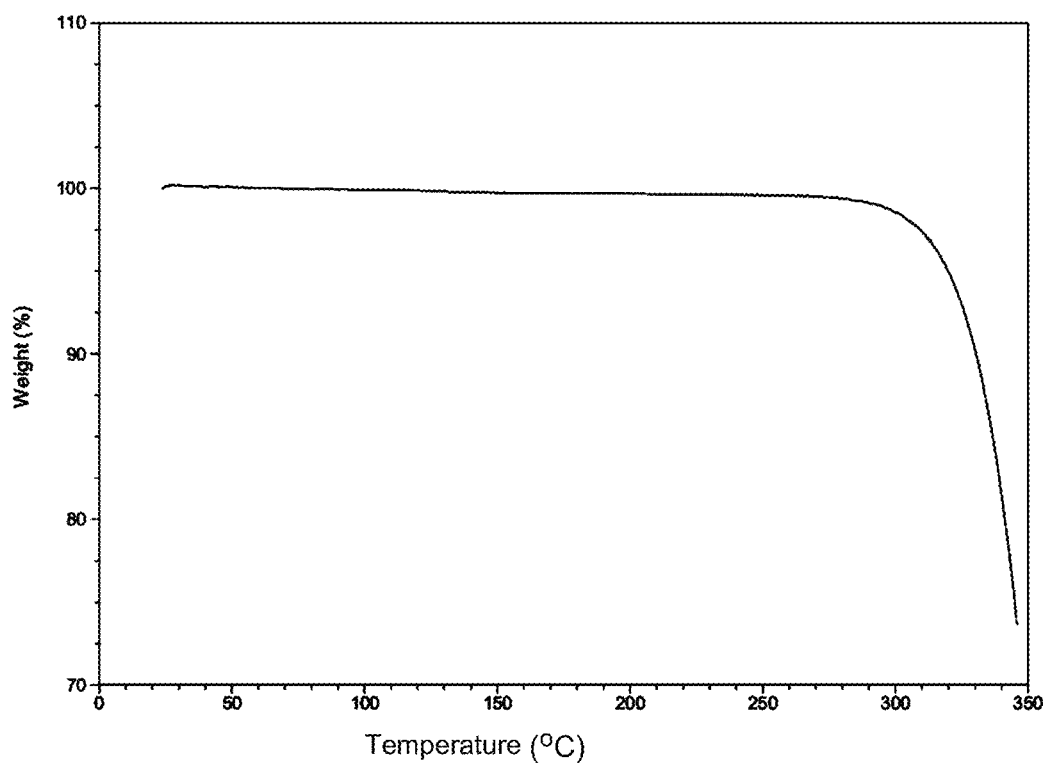

3. The Crystal Form of 17bNF according to claim 1, wherein said Crystal Form 17bNF-II, further has at least one of following characteristics: a differential scanning calorimetry spectrum has endothermic peaks at ~82-92° C., ~145-155° C. and ~225-235° C., and has exothermic peak at ~144-164° C. and a thermogravimetric analysis spectrum has a weight loss of ~2.9% before 100° C., the corresponding characteristic spectra are shown in FIGS. 7-9.

Figure 13:
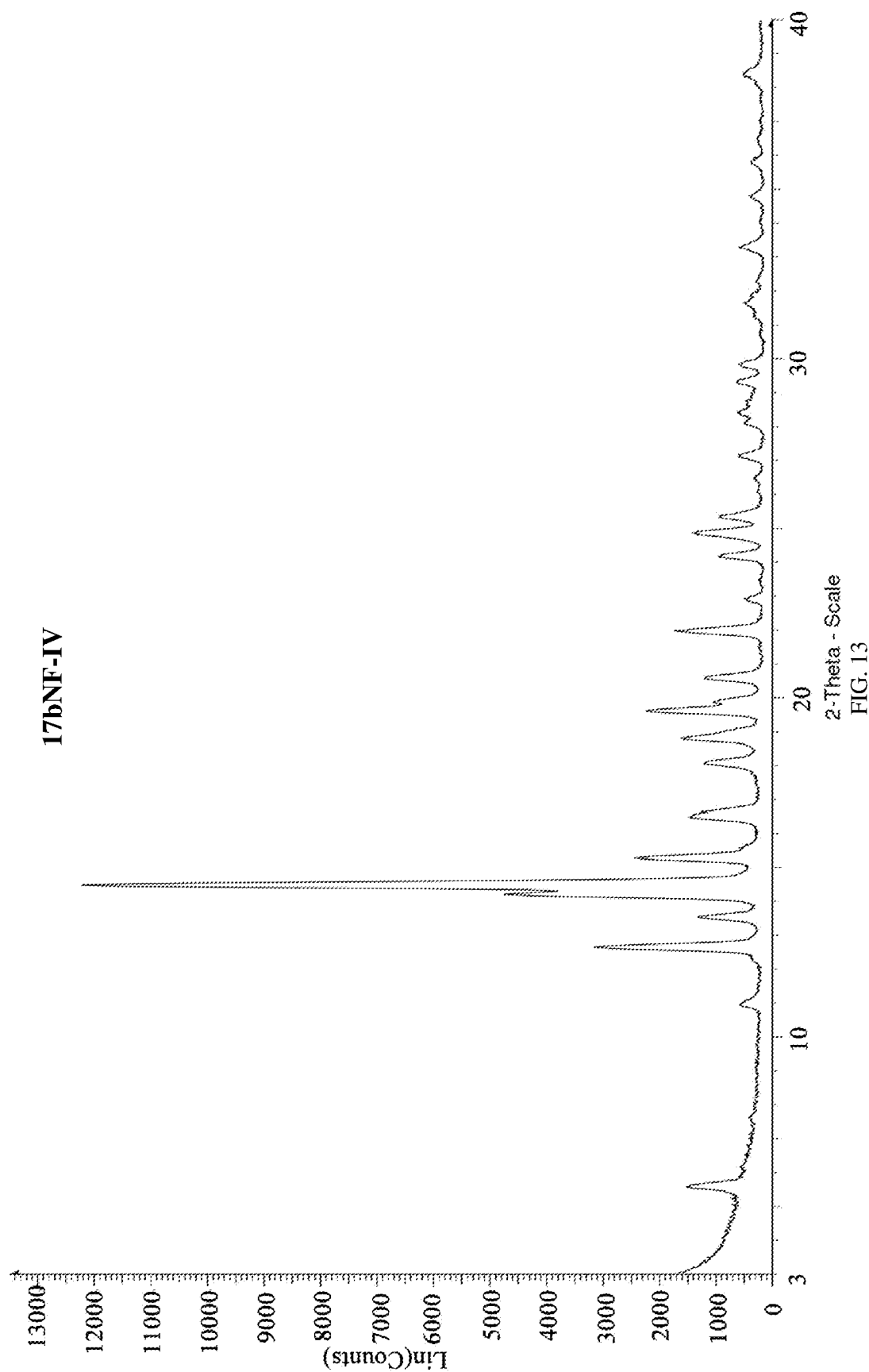
Figure 14:
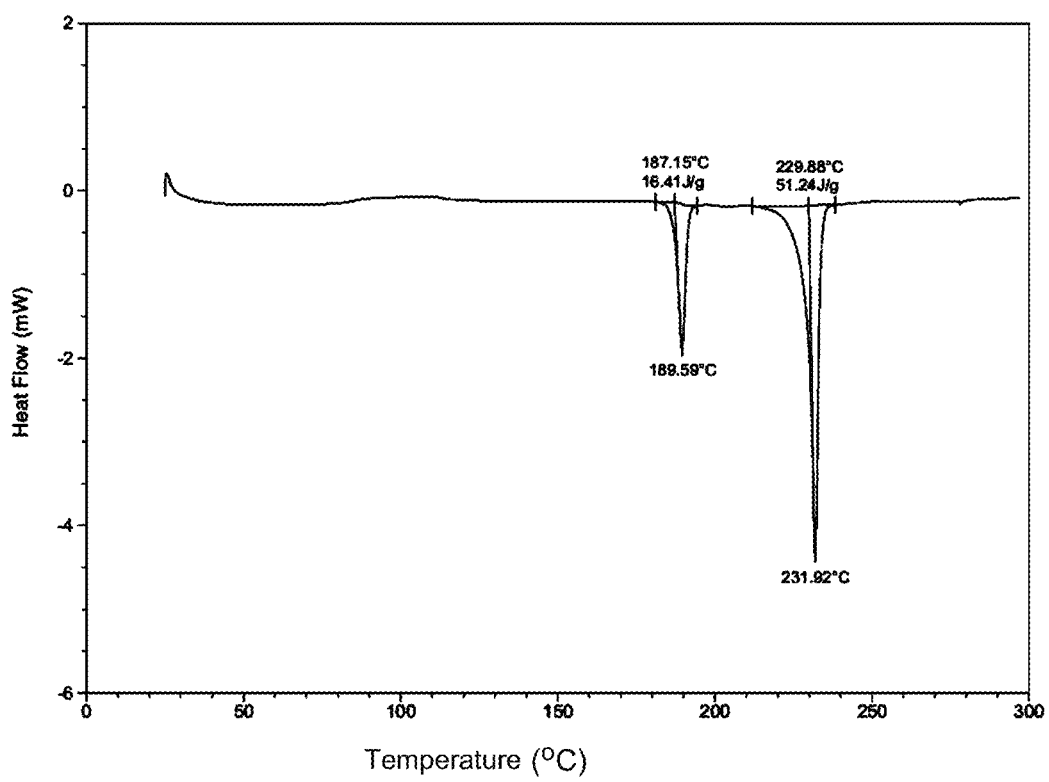
Figure 15:
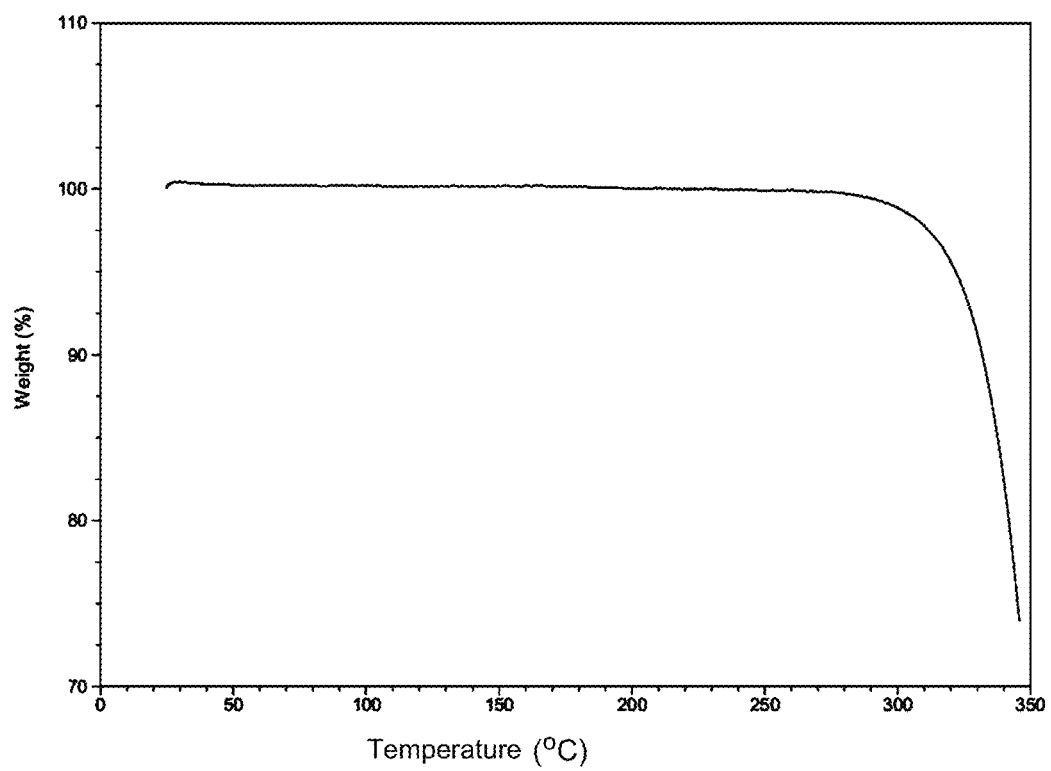
Figure 16:
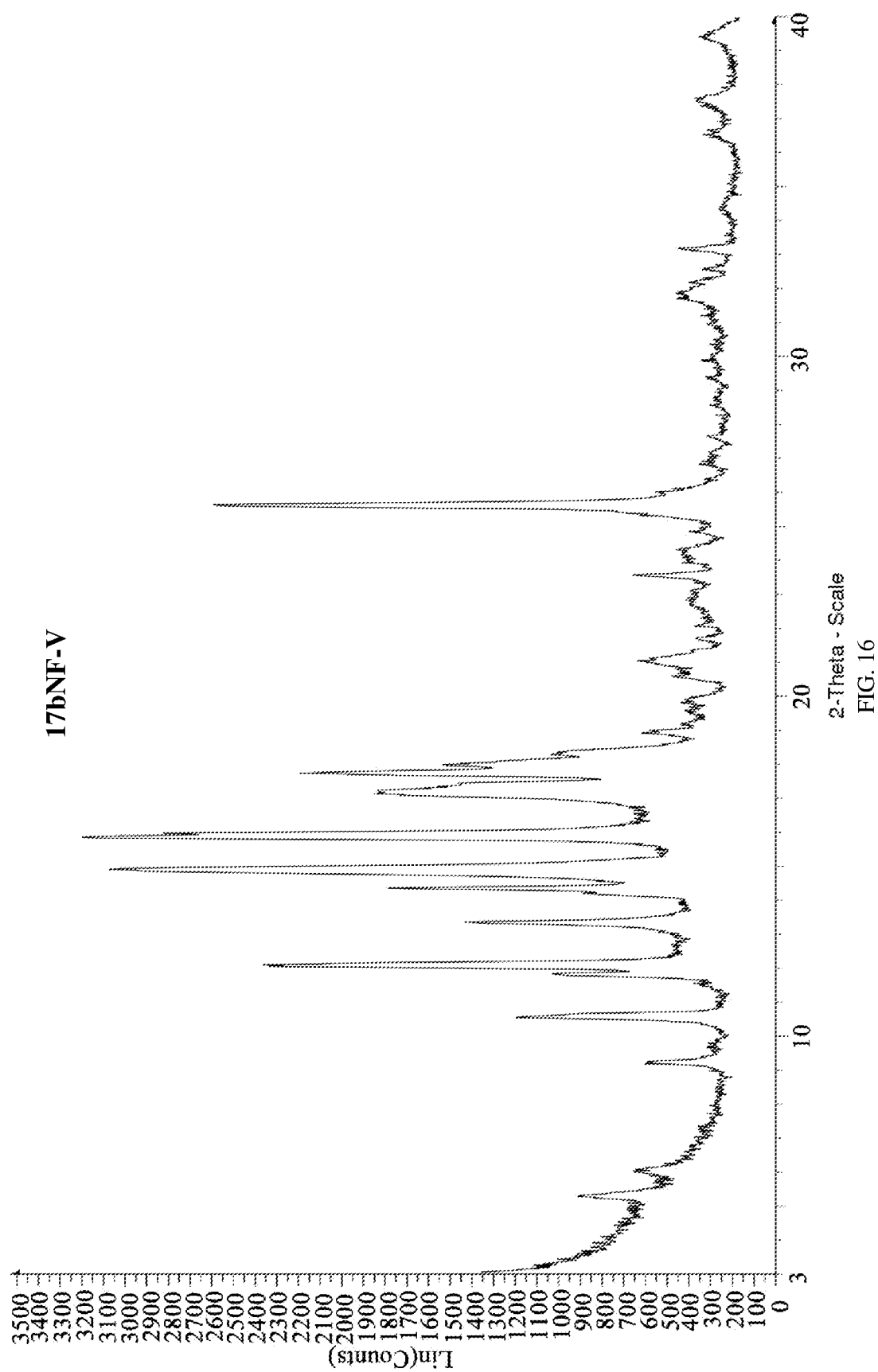
Figure 17:
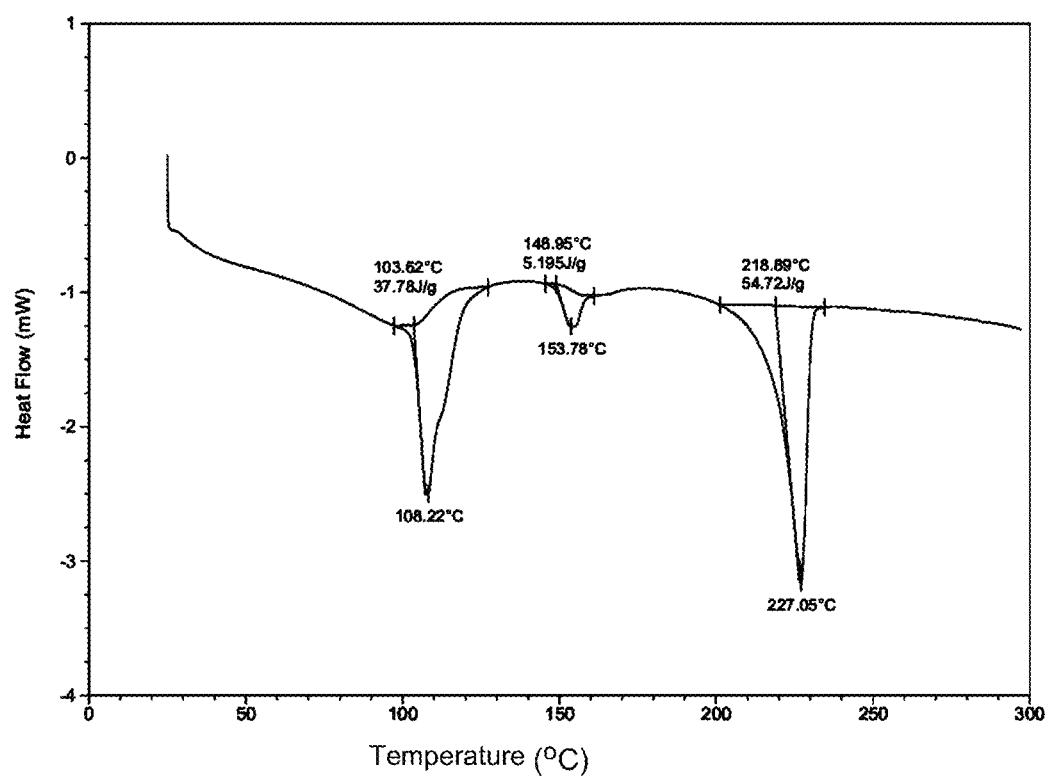
Figure 18:
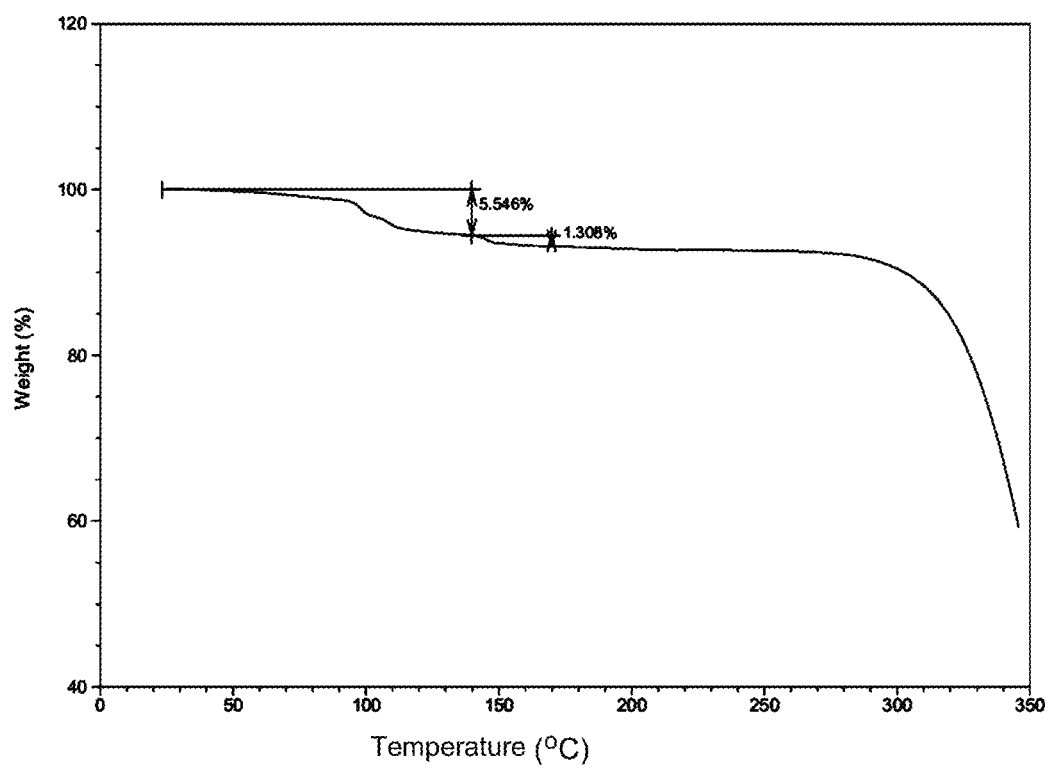
Figure 19:
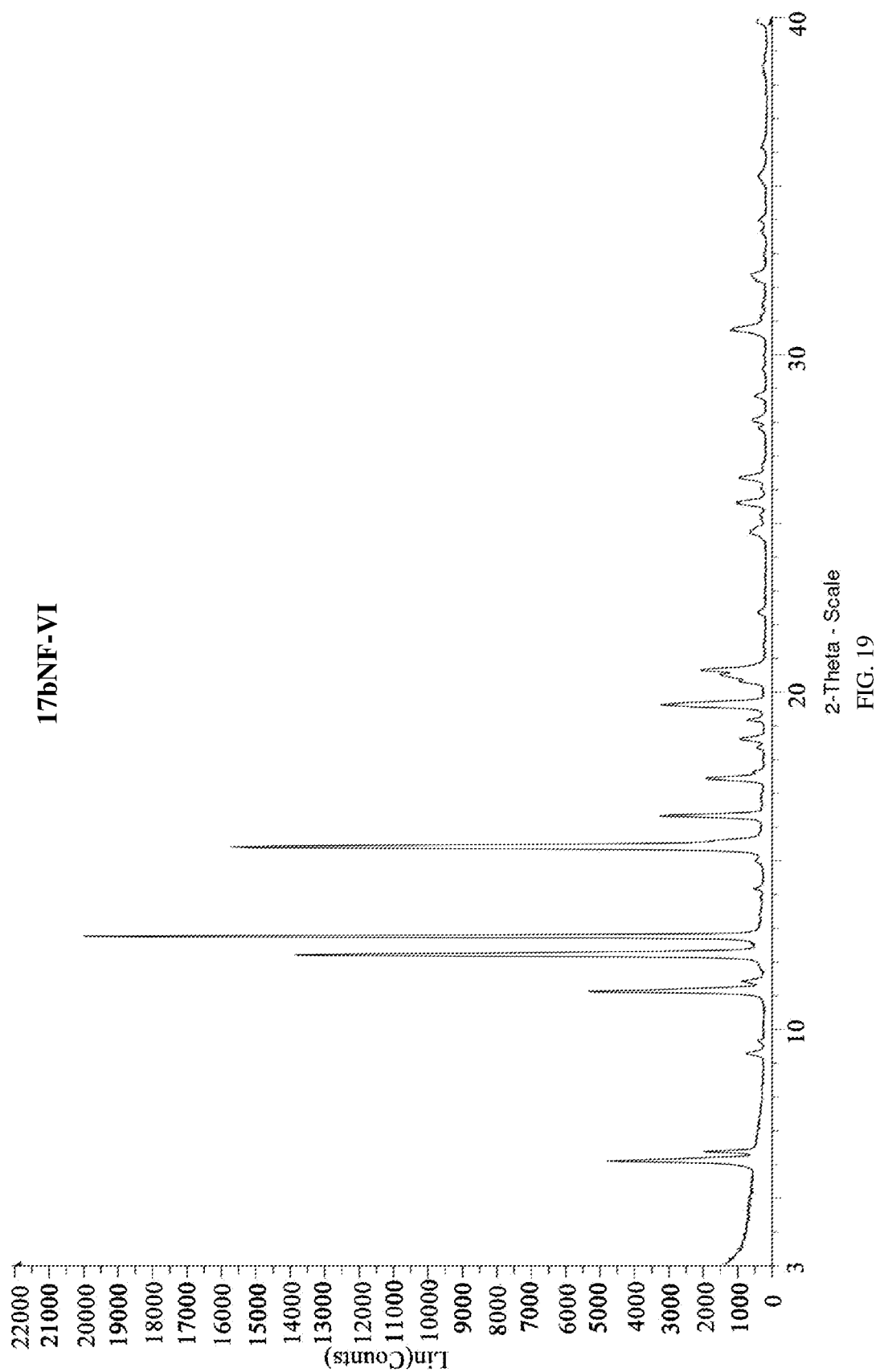
Figure 20:
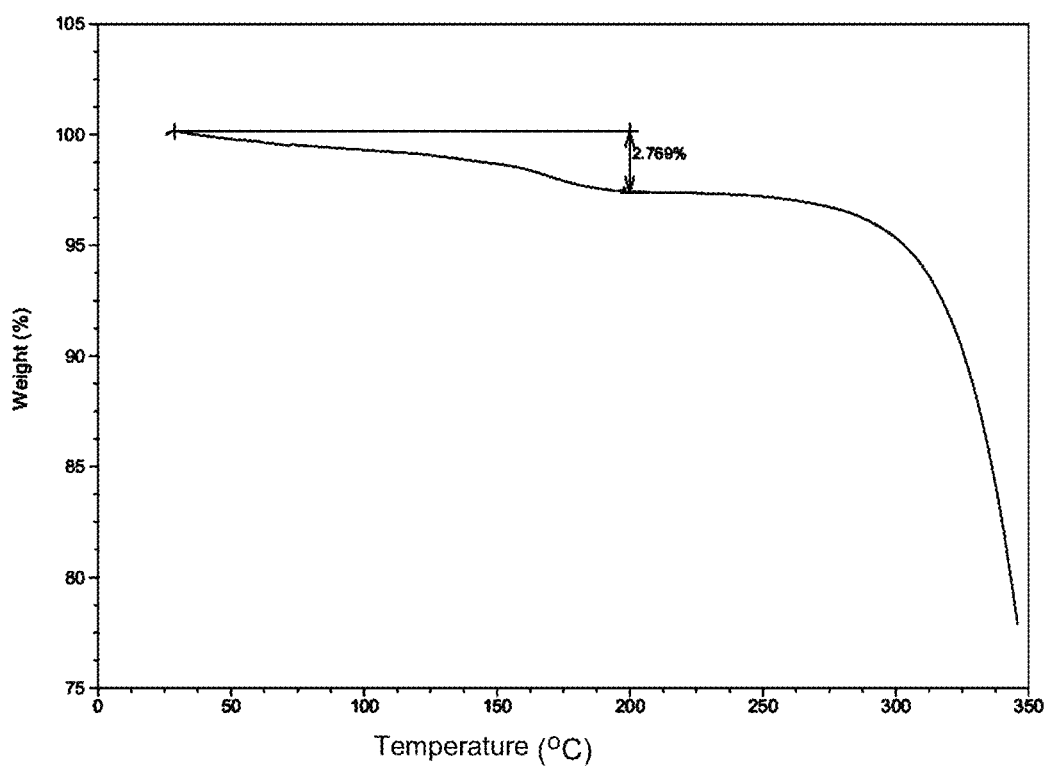
Figure 21:
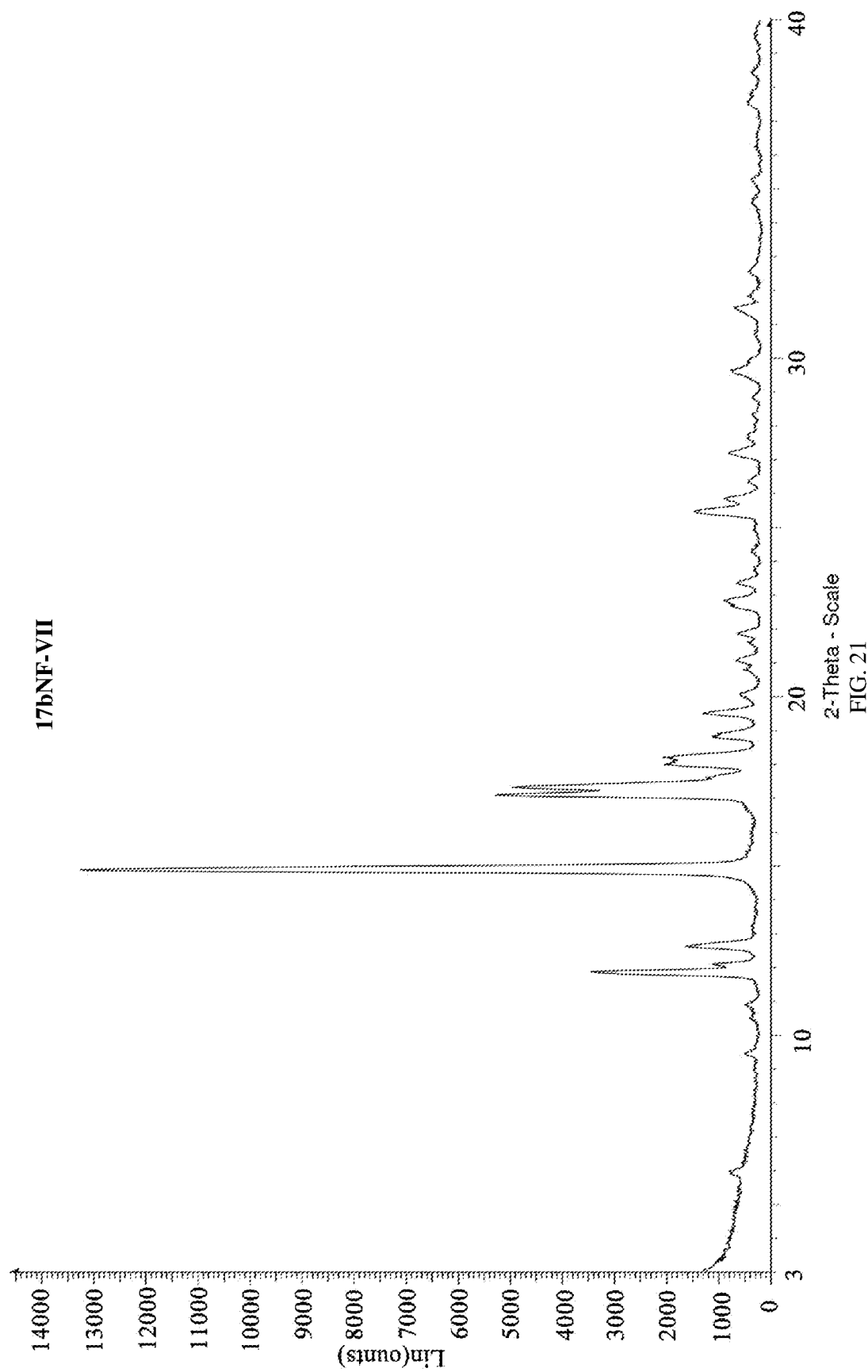
Figure 22:
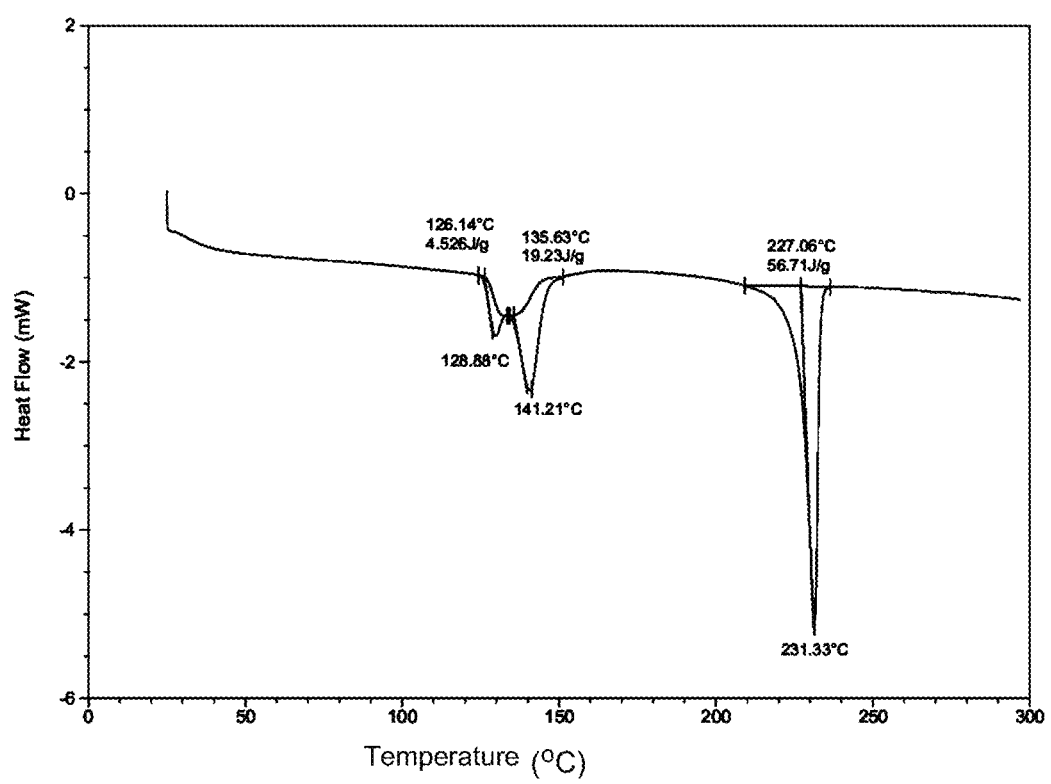
Figure 23:
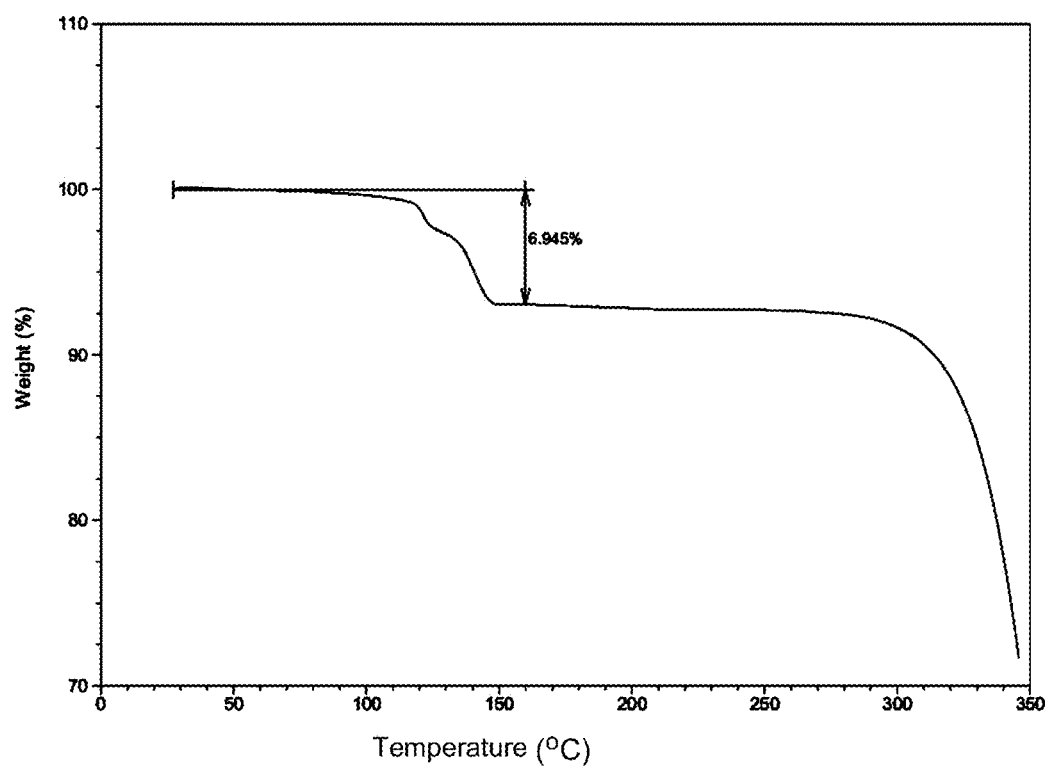
Figure 24:
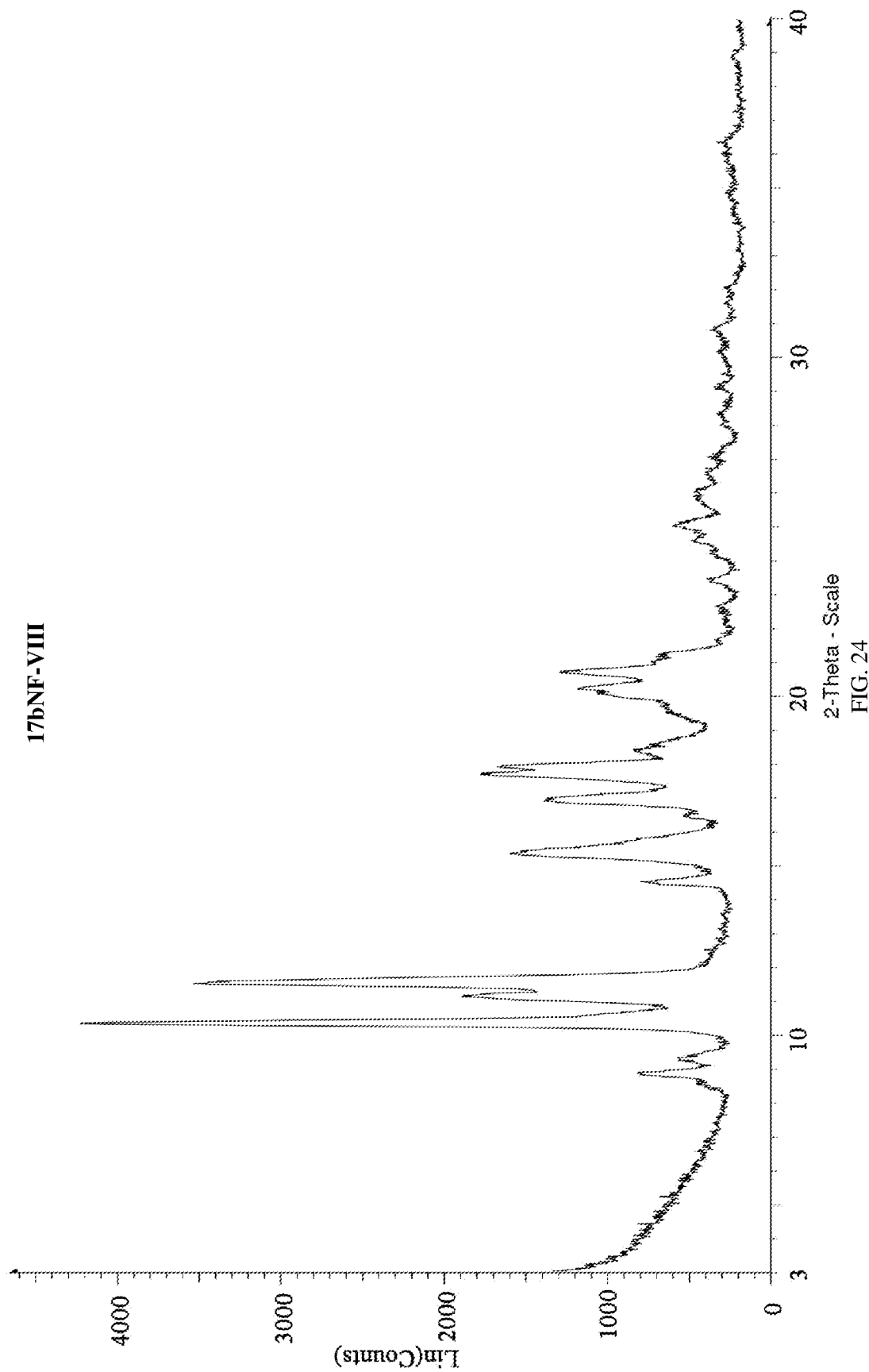
Figure 25:
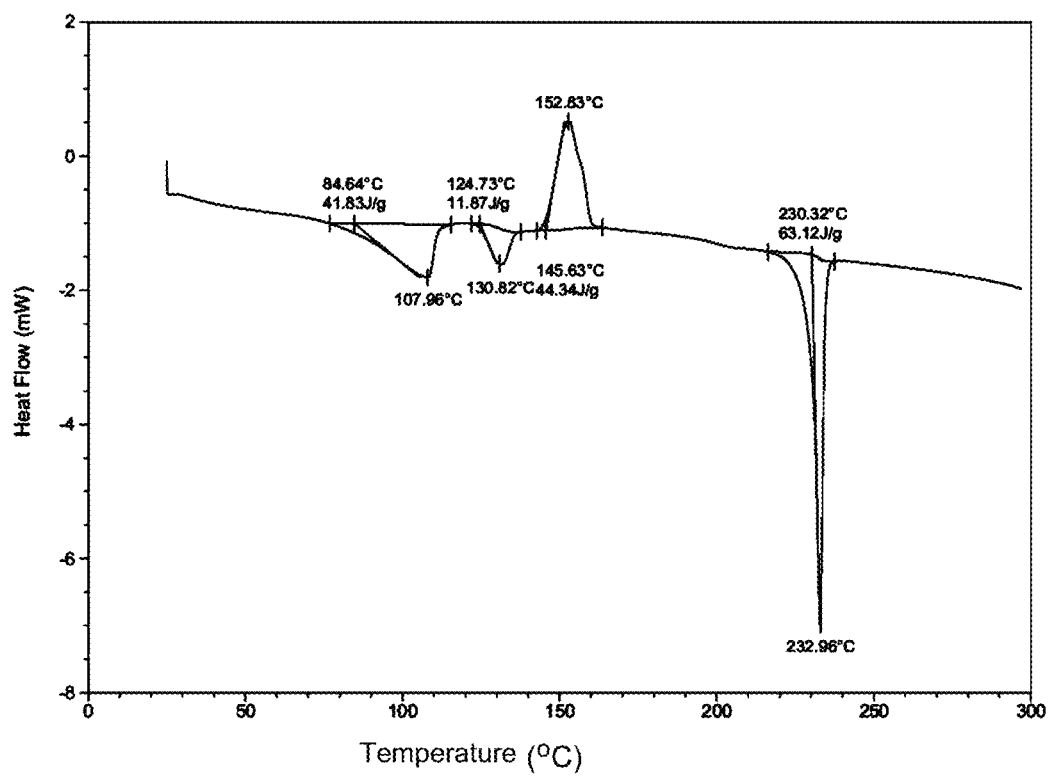
Figure 26:
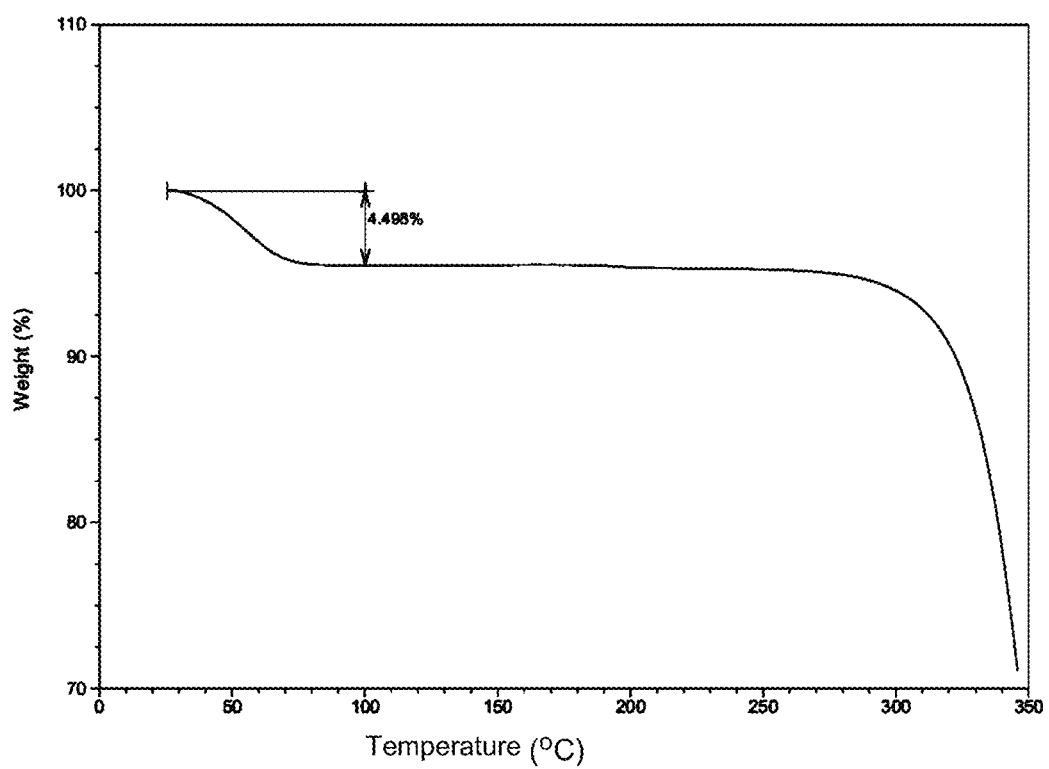
Figure 27:
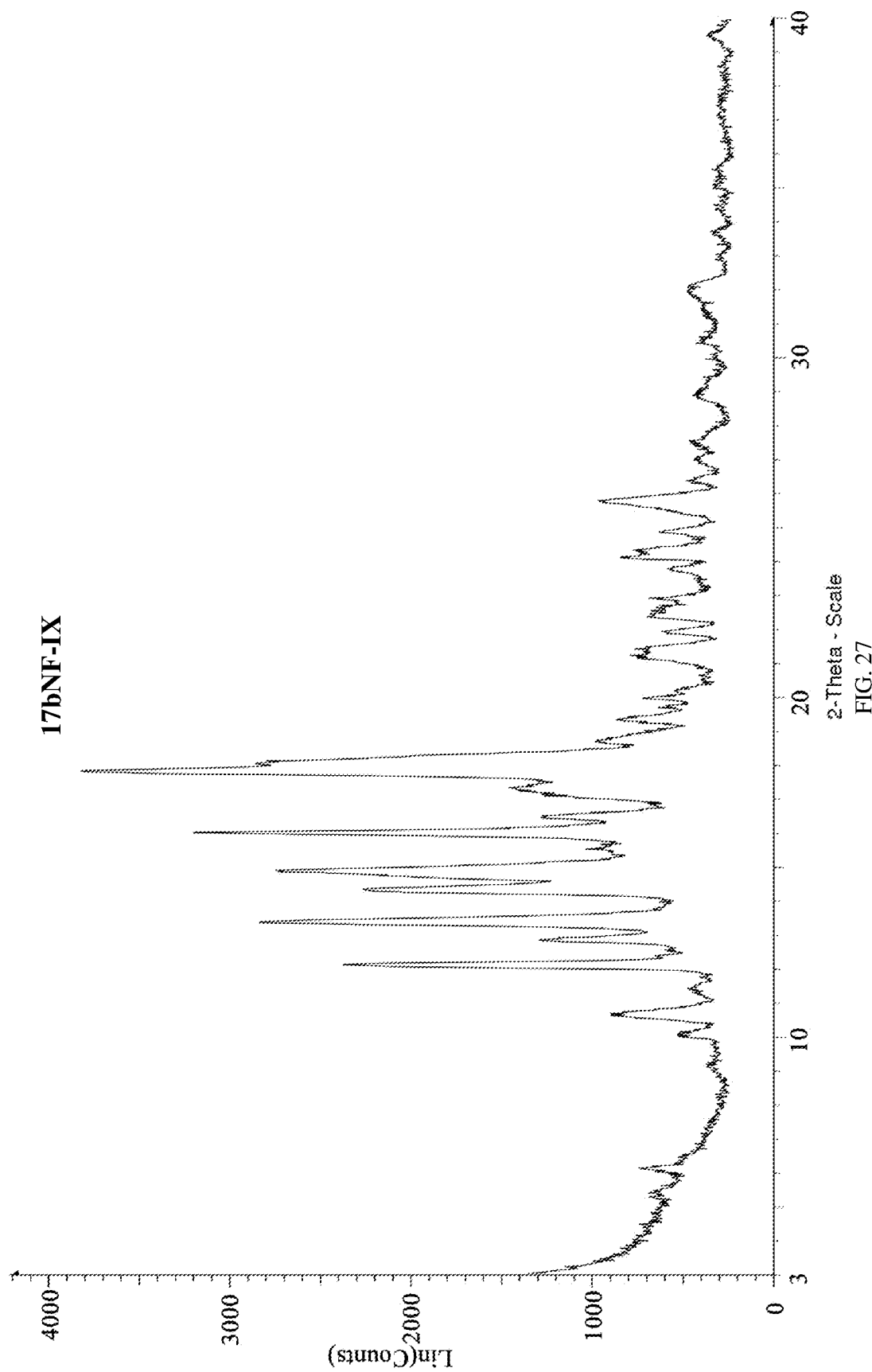
Figure 28:
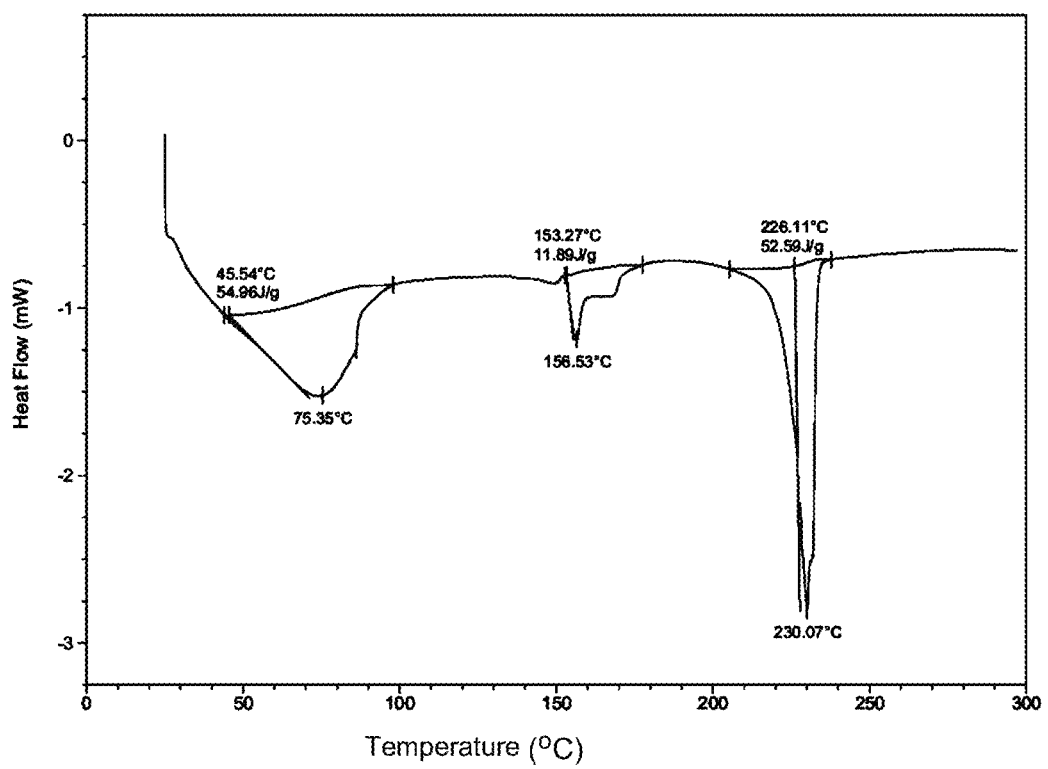
Figure 29:
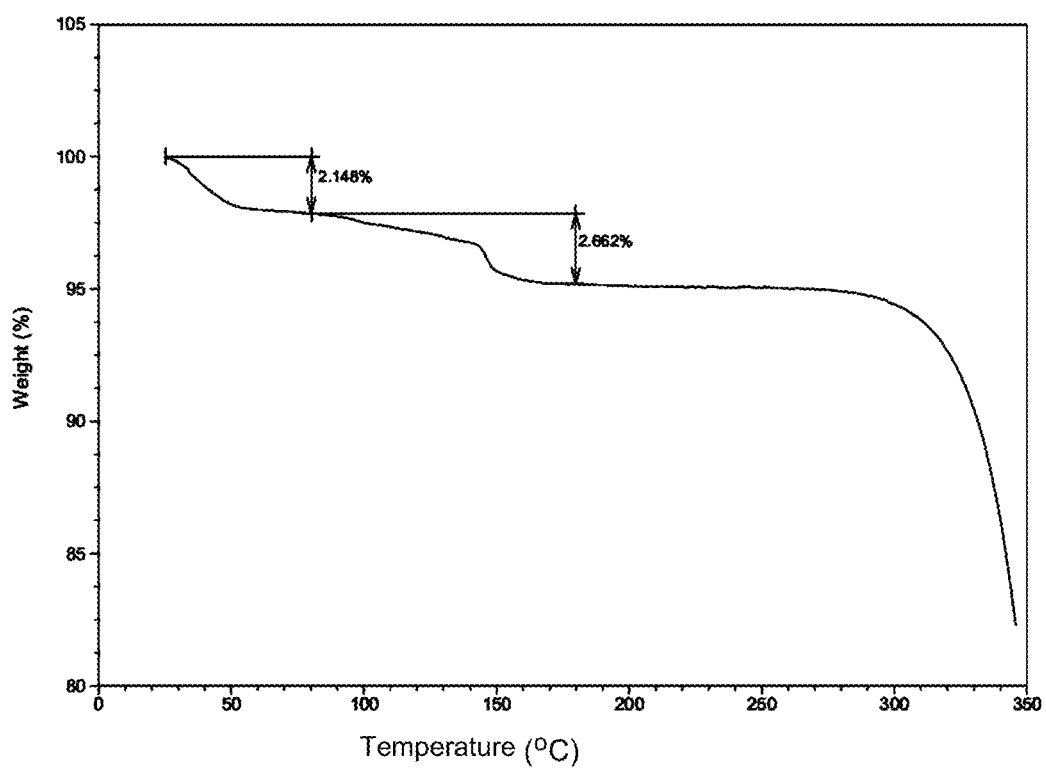
Figure 30:
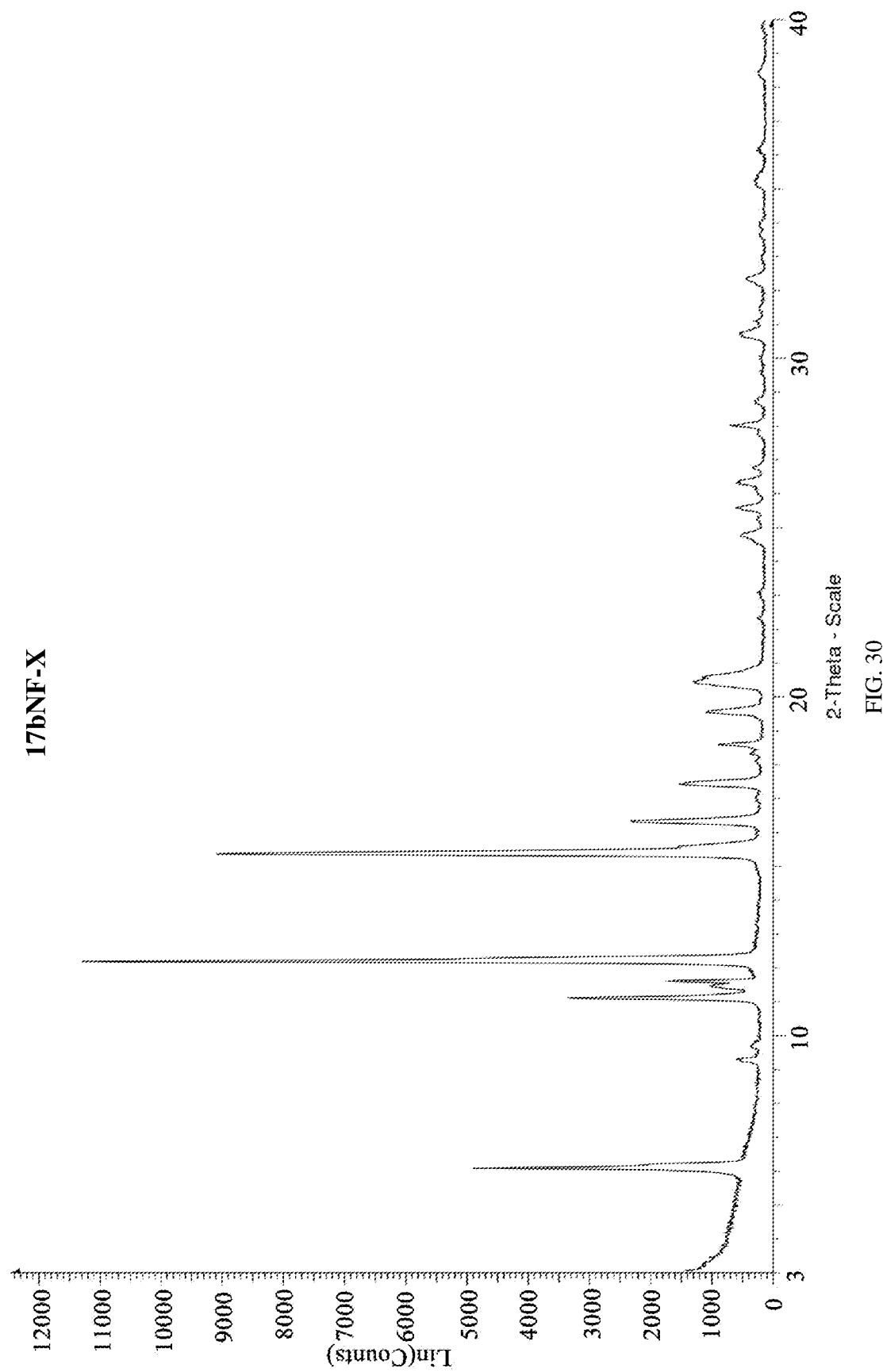
Figure 31:
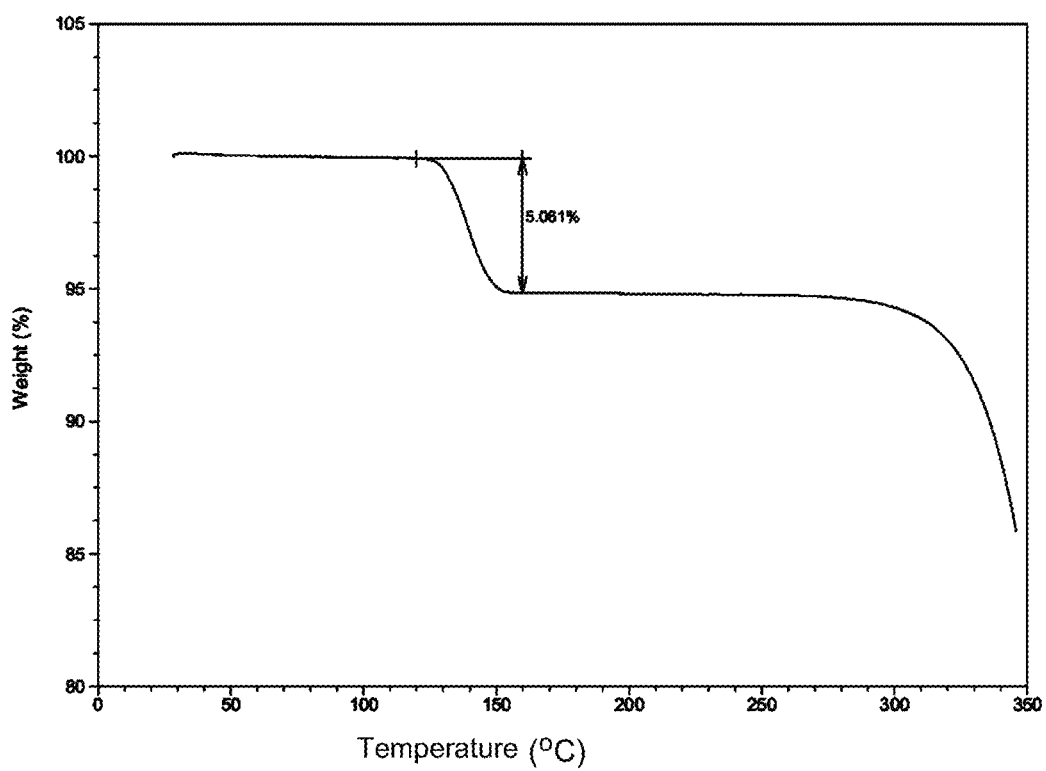
Figure 32:
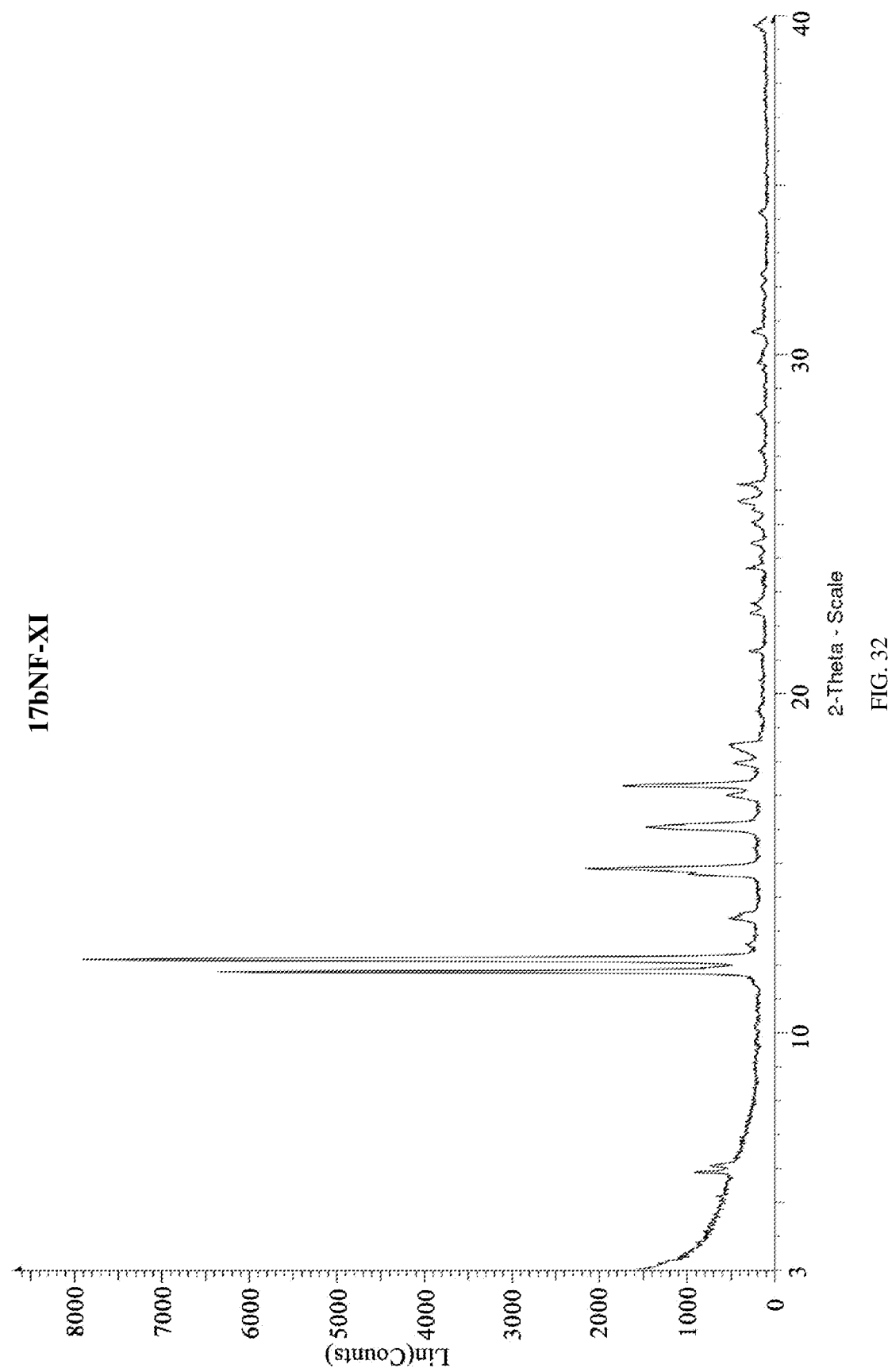
Figure 33:
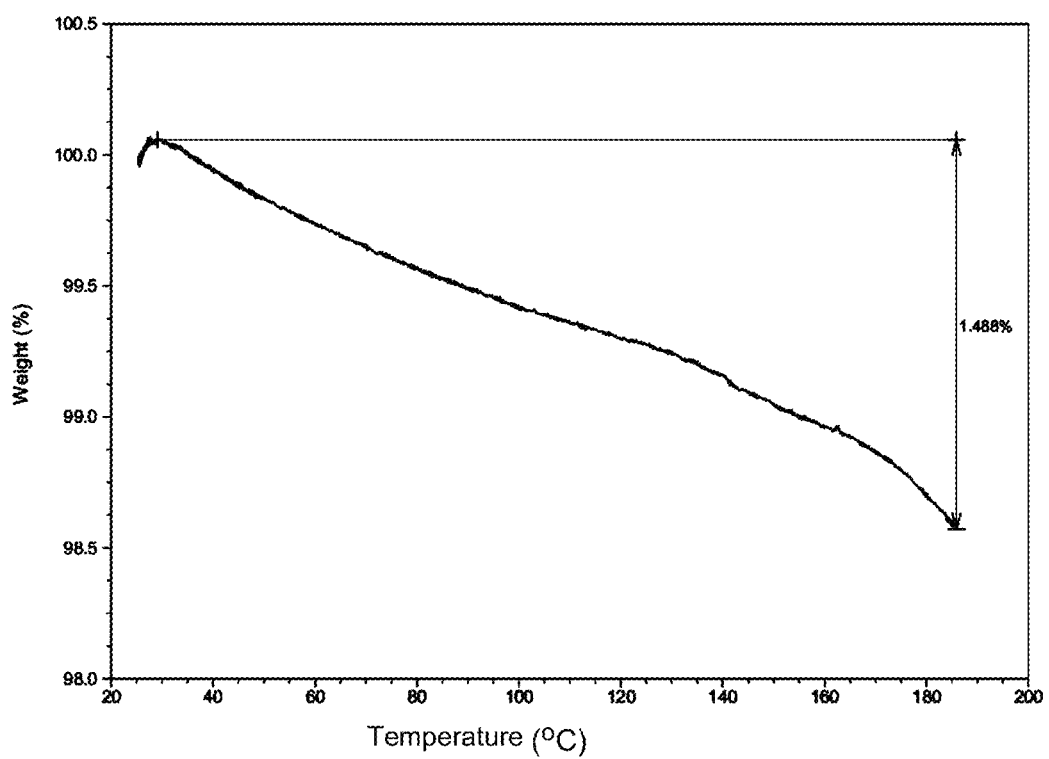
Figure 34:
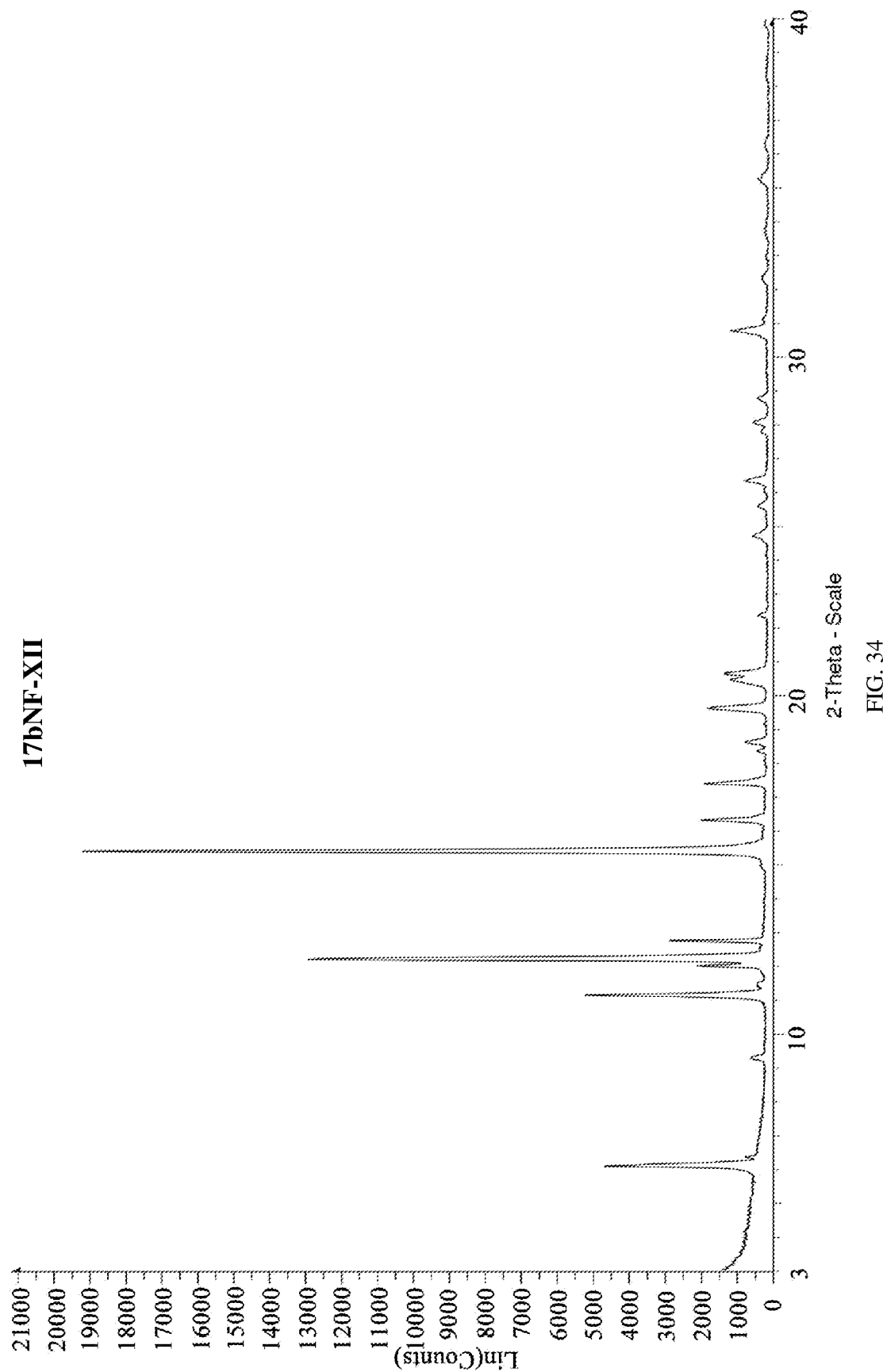
Figure 35:
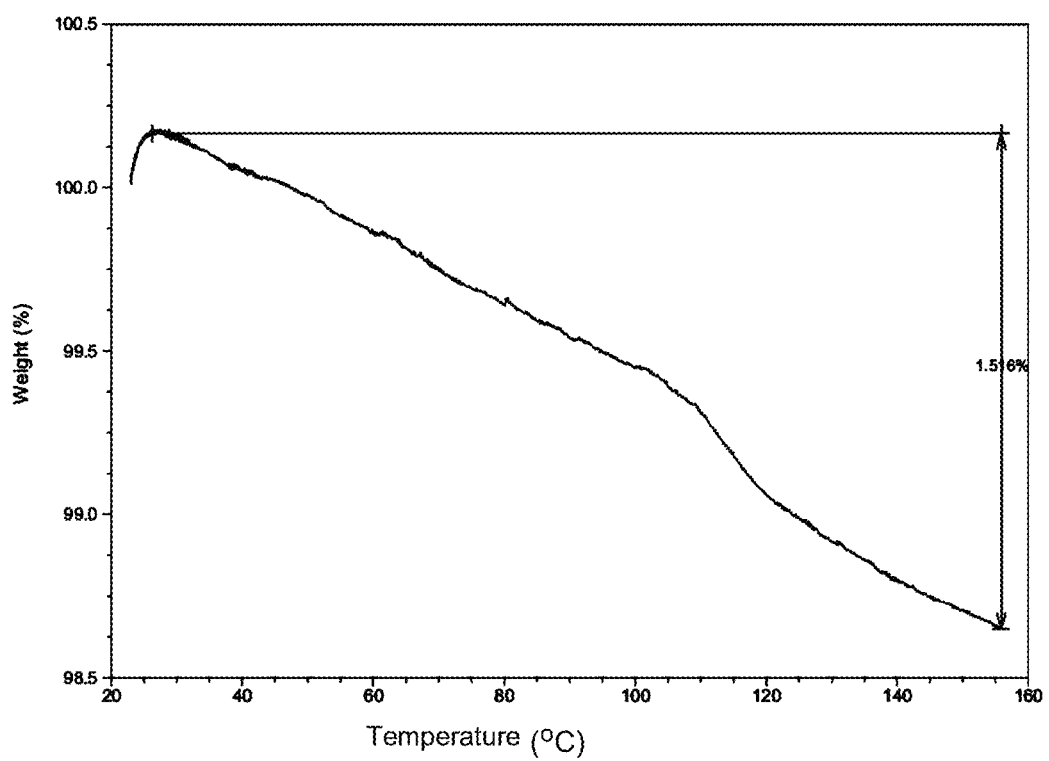
Figure 36:
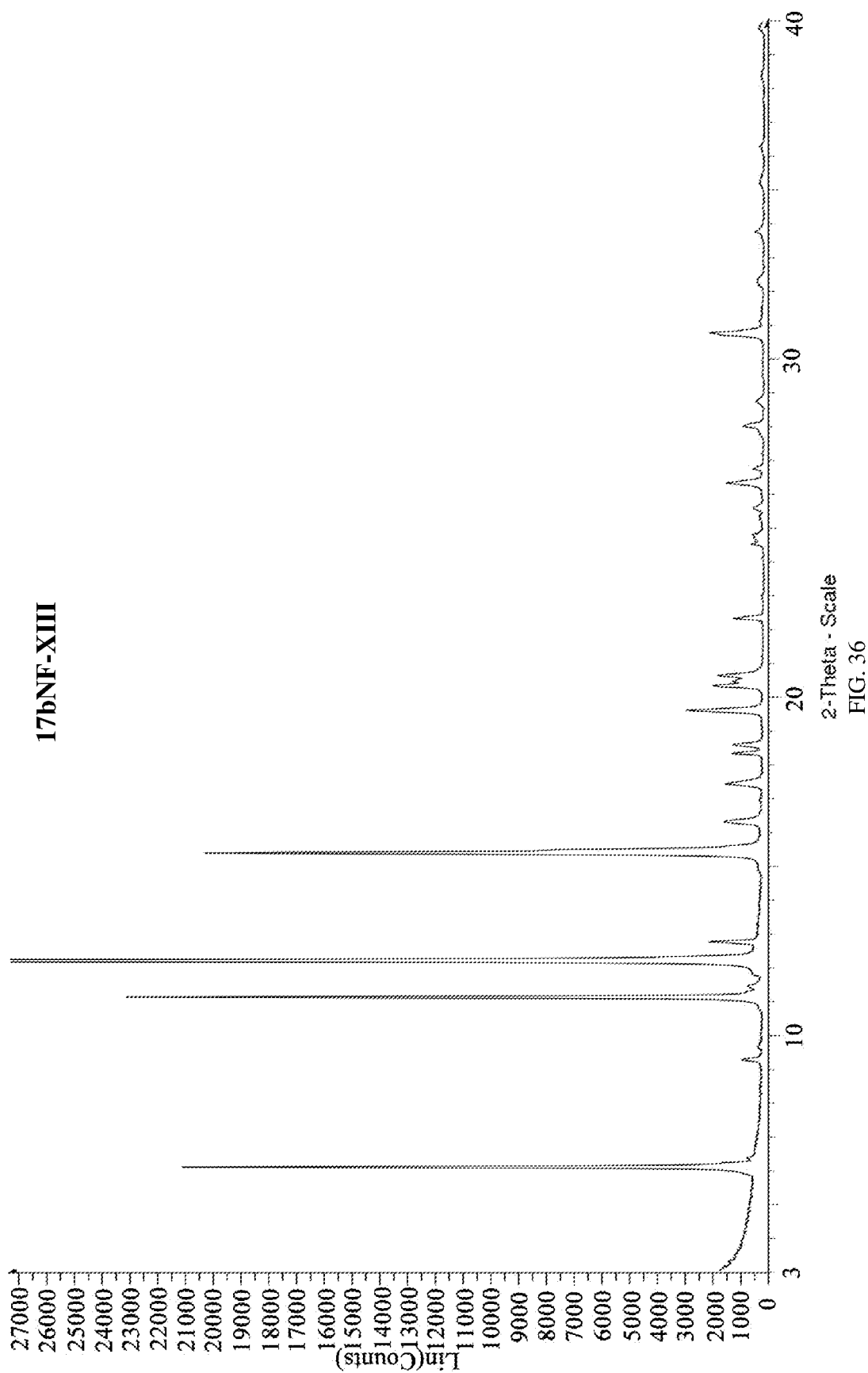
Figure 37:
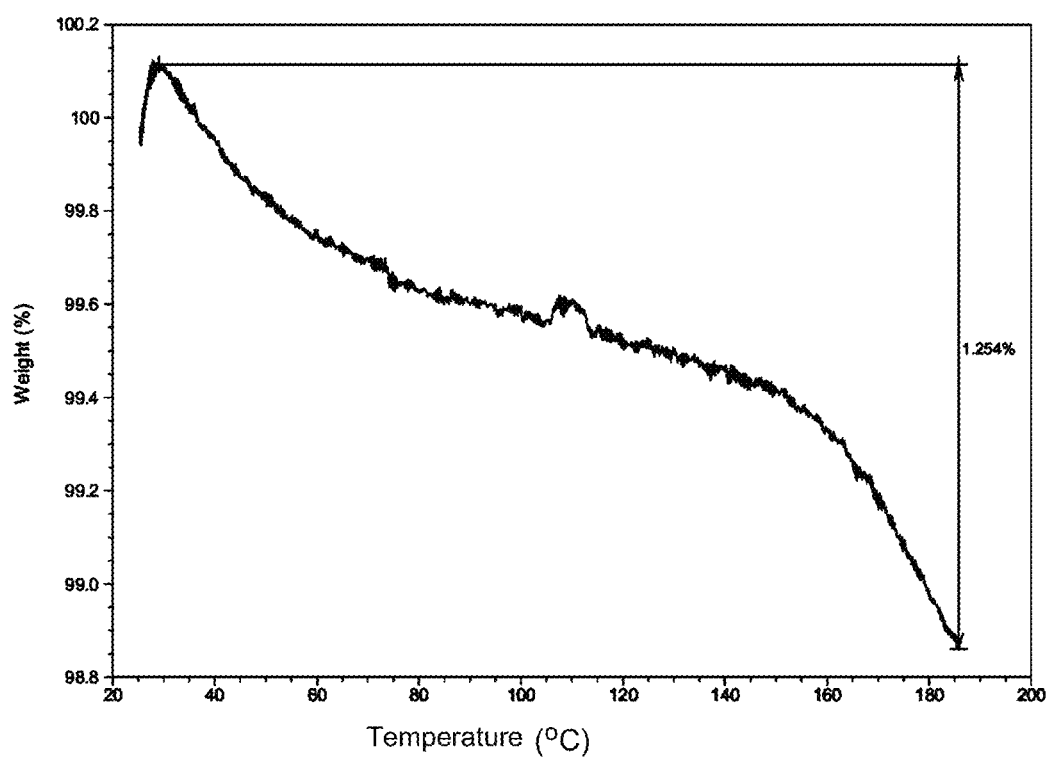
Figure 38:
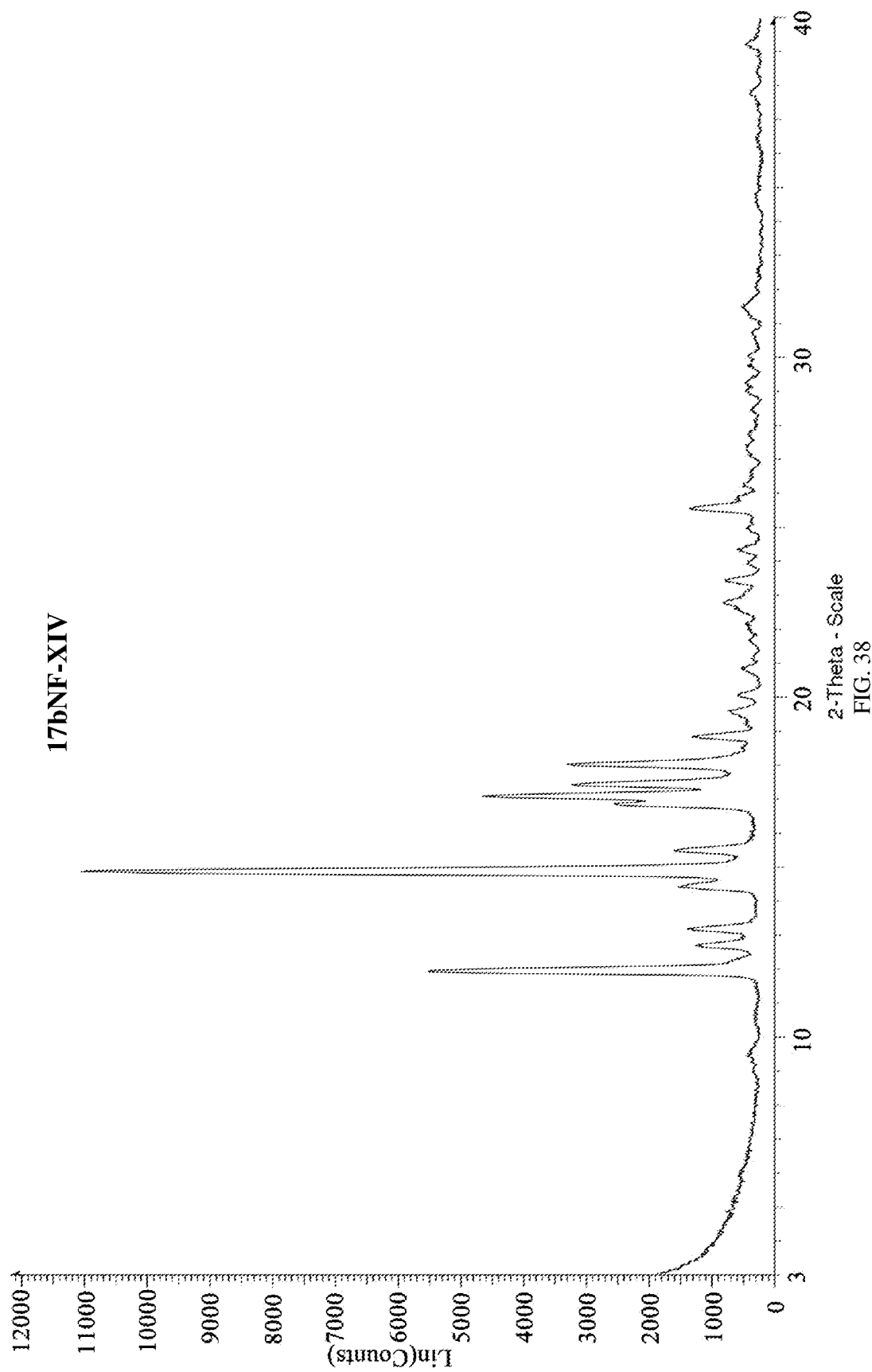
Figure 39:
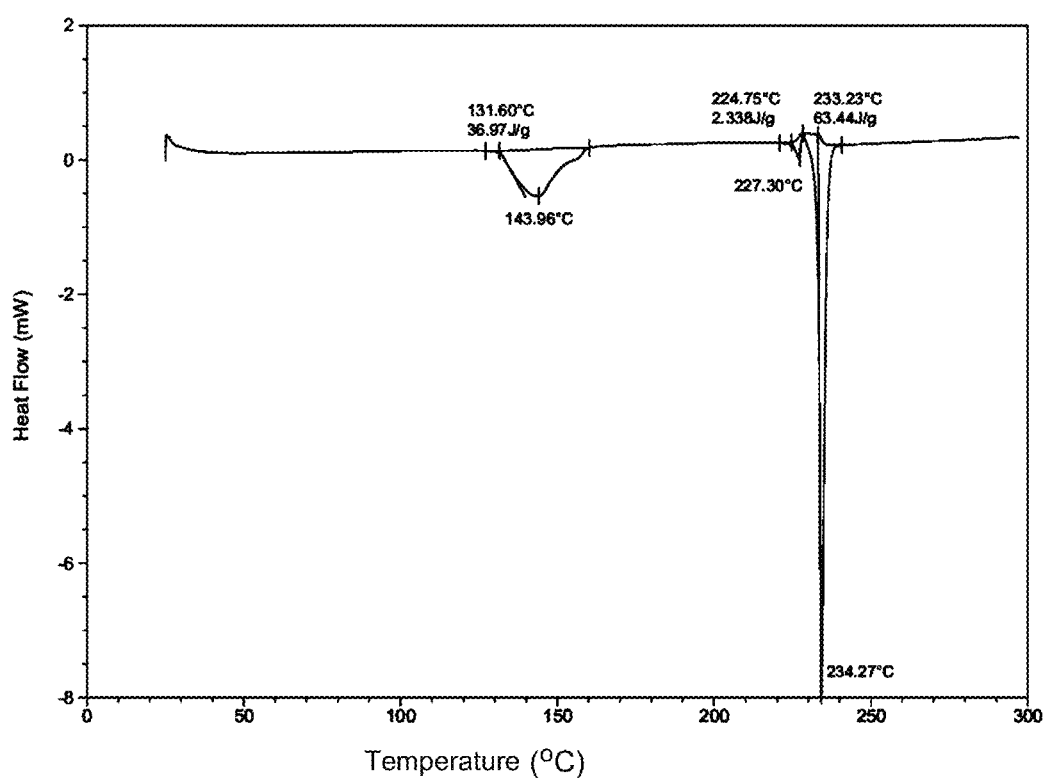
Figure 40:
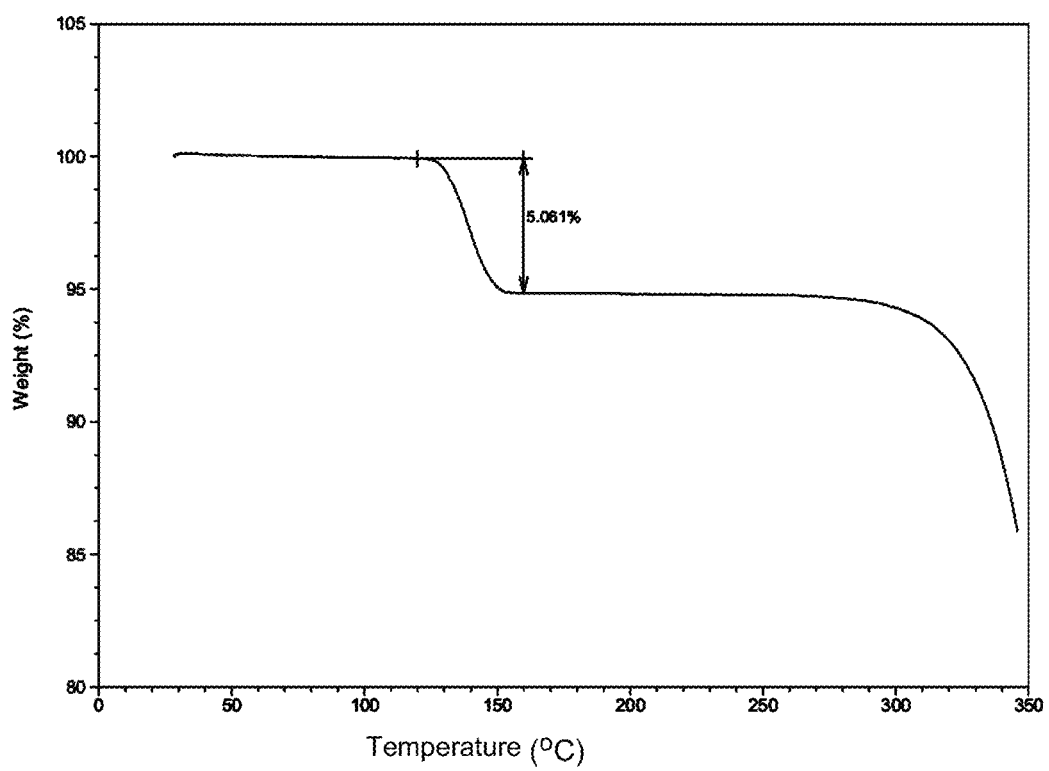
Figure 41:
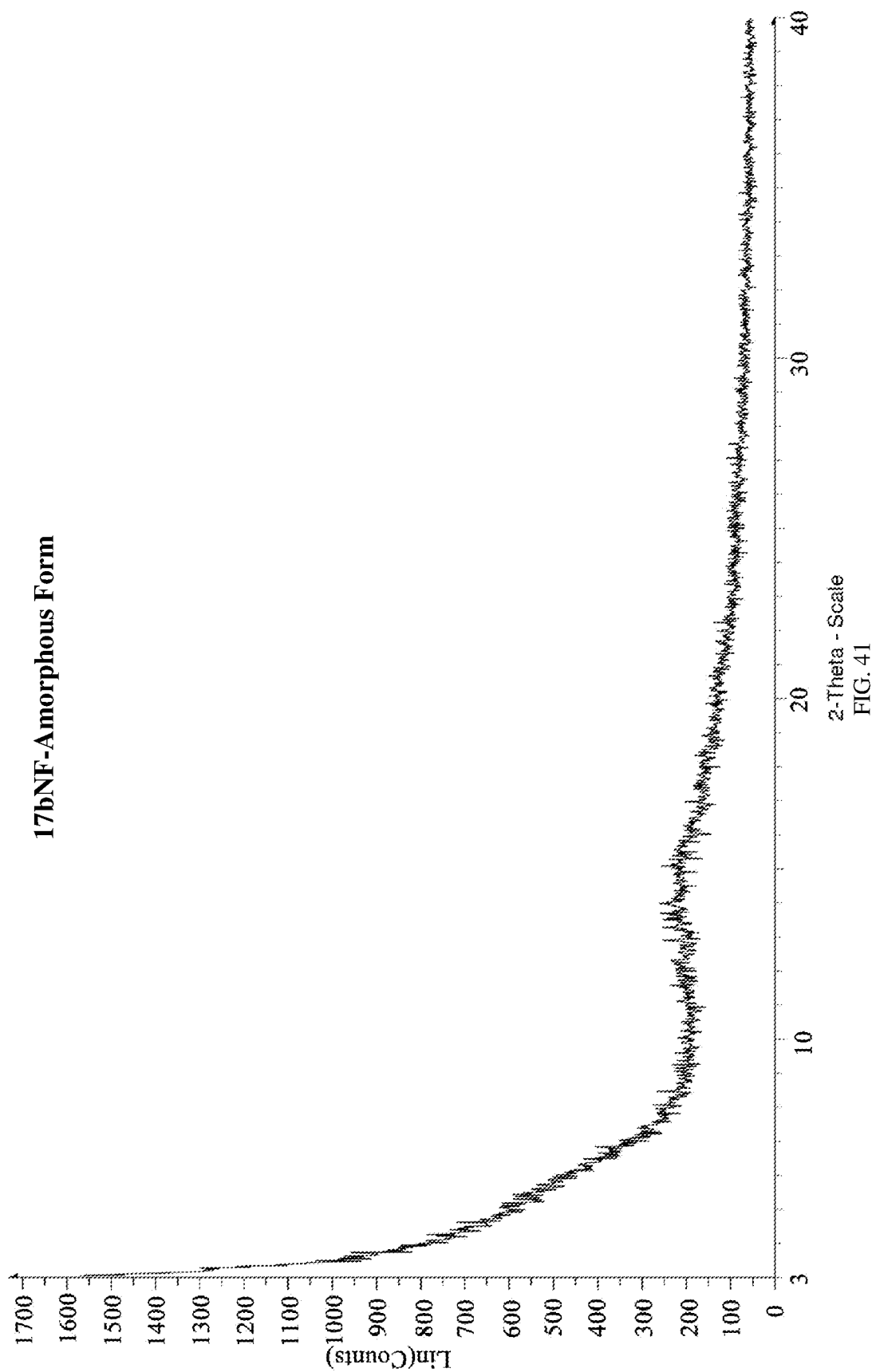

4. The Crystal Form of 17bNF according to claim 1, wherein said Crystal Form 17bNF-IV, further has at least one of following characteristics: a differential scanning calorimetry spectrum has endothermic peaks at 180-200° C. and 222-242° C.; it will be changed into Crystal Form 17bNF-I after being heated at 180-200° C.; the corresponding characteristic spectra are shown in FIGS. 13-15.

5. A preparation process for the Crystal Form of 17bNF according to claim 1, comprising:
    i) the preparation of the non-solvated Crystal Form 17bNF-I, comprising the following steps:
        a. dissolving or suspending 17bNF powder or crystals including 17bNF-0 in methanol, ethanol, tetrahydrofuran, acetone, isobutanol, isopropyl acetate, 2-butanone, isopropyl alcohol, ethyl acetate, acetonitrile, toluene, methyl tert-butyl ether or water, separately;
        b. separately filtering the solutions or suspensions from Step a, and then taking the filtrates;
        c. taking the 17bNF methanol solution, or mixing the 17bNF methanol solution with the filtrate of the 17bNF isopropyl alcohol suspension, 17bNF tetrahydrofuran solution, 17bNF acetone solution, 17bNF isobutyl alcohol solution, 17bNF isopropyl acetate solution, the filtrate of 17bNF ethyl acetate suspension, the filtrate of 17bNF toluene suspension, or the filtrate of the 17bNF methyl tert-butyl ether suspension, at ratios of 30%:70% to 70%:30%; or
        taking the 17bNF ethanol solution, or mixing the 17bNF ethanol solution with the 17bNF tetrahydrofuran solution, 17bNF acetone solution, 17bNF isobutyl alcohol solution, 17bNF isopropyl acetate solution, 17bNF 2-butanone solution, the filtrate of the 17bNF isopropyl alcohol suspension, the filtrate of the 17bNF ethyl acetate suspension, the filtrate of the 17bNF toluene suspension, or the filtrate of the 17bNF methyl tert-butyl ether suspension, at ratios of 30%:70% to 70%:30%; or
        mixing the filtrate of the 17bNF isopropyl alcohol suspension with 17bNF tetrahydrofuran solution, 17bNF acetone solution, 17bNF isobutyl alcohol solution, 17bNF isopropyl acetate solution, 17bNF 2-butanone solution, the filtrate of the 17bNF isopropyl alcohol suspension, the filtrate of the 17bNF ethyl acetate suspension, the filtrate of the 17bNF acetonitrile suspension, or the filtrate of the 17bNF toluene suspension, at ratios of 30%:70% to 70%:30%; or taking the 17bNF tetrahydrofuran solution, or mixing the 17bNF tetrahydrofuran solution with the 17bNF acetone solution, 17bNF isobutyl alcohol solution, 17bNF isopropyl acetate solution, 17bNF 2-butanone solution, the filtrate of the 17bNF ethyl acetate suspension, the filtrate of the 17bNF acetonitrile suspension, the filtrate of the 17bNF toluene suspension, or the filtrate of the 17bNF methyl tert-butyl ether suspension, at ratios of 30%:70% to 70%:30%; or taking filtrate of the 17bNF ethyl acetate suspension, or mixing the filtrate of the 17bNF ethyl acetate suspension with the 17bNF acetone solution, 17bNF 2-butanone solution, or the filtrate of the 17bNF acetonitrile suspension, at ratios of 30%:70% to 70%:3070%:30%; or taking the 17bNF acetone solution, or mixing the 17bNF acetone solution with the 17bNF isobutyl alcohol solution, 17bNF isopropyl acetate solution, 17bNF 2-butanone solution, or the filtrate of the 17bNF toluene suspension, at ratios of 30%:70% to 70%:30%; or taking the 17bNF isobutyl alcohol solution, or mixing the 17bNF isobutyl alcohol solution with the 17bNF isopropyl acetate solution, the filtrate of the 17bNF acetonitrile suspension, 17bNF 2-butanone solution, the filtrate of the 17bNF toluene suspension, the filtrate of the 17bNF water suspension or the filtrate of the 17bNF methyl tert-butyl ether suspension, at ratios of 30%:70% to 70%:30%; or mixing the 17bNF isopropyl acetate solution with the 17bNF 2-butanone solution, at ratios of 30%:70% to 70%:30%; or mixing the filtrate of the 17bNF acetonitrile suspension with the 17bNF 2-butanone solution, or the filtrate of the 17bNF methyl tert-butyl ether suspension, at ratios of 30%:70% to 70%:30%; or taking the 17bNF 2-butanone solution, or mixing the 17bNF 2-butanone solution with the filtrate of the 17bNF toluene suspension, the filtrate of the 17bNF water suspension or the filtrate of the 17bNF methyl tert-butyl ether suspension, at ratio of 30%:70% to 70%:30%;

d. volatilizing any one of the solutions of 17bNF in a single solvent or two mixed solvents obtained from Step c at an environmental condition to obtain the non-solvated Crystal Form 17bNF;

ii) the preparation process of the non-solvated Crystal Form 17bNF-II, comprising the following steps:
   a. suspending the 17bNF-0 solid in water, and keeping stirring;
   b. filtering the suspension, collecting and drying the solid, and obtaining the non-solvated Crystal Form 17bNF-II; or iii) the preparation process of the non-solvated Crystal Form 17bNF-IV, comprising the following steps:
   a. suspending the 17bNF-0 solid in methyl tert-butyl ether to produce a suspension;
   b. stirring and beating the suspension; and adding some seed crystal 17bNF-1V;
   c. filtering the suspension, collecting and drying the solid, and obtaining the non-solvated Crystal Form 17bNF-IV.

6. A preparation process for the non-solvated Crystal Form 17bNF-I according to claim 1, comprising the following steps:
   a. suspending the ethanol-solvated Crystal Form 17bNF-0 solid in ethyl ether, and keeping stirring to obtain a suspension;
   b. filtering the suspension, collecting and drying the solid, and obtaining the non-solvated Crystal Form 17bNF-I.

7. The preparation process for the Crystal Form of 17bNF according to claim 5, wherein two 17bNF solutions are mixed at ratio of 40%:60% to 60%:40% in Step i) c.

8. The preparation process for the Crystal Form of 17bNF according to claim 5, wherein two 17bNF solutions are mixed at ratio of 50%:50% in Step i) c.

* * * * *